US012624112B2

(12) United States Patent
Xiong et al.

(10) Patent No.: US 12,624,112 B2
(45) Date of Patent: May 12, 2026

(54) ANTI-ST2 ANTIBODY, ENCODING NUCLEIC ACID MOLECULES THEREOF AND METHODS OF USE THEREOF

(71) Applicant: MABWELL (SHANGHAI) BIOSCIENCE CO., LTD., Shanghai (CN)

(72) Inventors: Xinhui Xiong, Shanghai (CN); Tao Zhang, Shanghai (CN); Kai Zhong, Shanghai (CN); Wei Wu, Shanghai (CN); Qianhui Huang, Shanghai (CN); Xing Li, Shanghai (CN); Hong Pan, Shanghai (CN)

(73) Assignee: MABWELL (SHANGHAI) BIOSCIENCE CO., LTD., Shanghai (CN)

( * ) Notice: Subject to any disclaimer, the term of this patent is extended or adjusted under 35 U.S.C. 154(b) by 920 days.

(21) Appl. No.: 17/794,582

(22) PCT Filed: Jan. 21, 2021

(86) PCT No.: PCT/CN2021/073009
§ 371 (c)(1),
(2) Date: Jul. 21, 2022

(87) PCT Pub. No.: WO2021/147937
PCT Pub. Date: Jul. 29, 2021

(65) Prior Publication Data
US 2023/0220086 A1 Jul. 13, 2023

(30) Foreign Application Priority Data

Jan. 21, 2020 (CN) ........................ 202010072085.X

(51) Int. Cl.
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
CPC ............ C07K 16/2866; C07K 2317/24; C07K 2317/33; C07K 2317/565; C07K 2317/76; C07K 2317/92; C07K 2317/94; C07K 2317/56; C07K 2319/00; A61K 2039/505; A61P 37/02; A61P 1/00; A61P 1/12; A61P 9/04; A61P 11/00; A61P 11/02; A61P 11/06; A61P 19/02; A61P 25/00; A61P 29/00; A61P 31/00; A61P 37/00; G01N 33/6893

See application file for complete search history.

(56) References Cited

U.S. PATENT DOCUMENTS

2003/0124624 A1 7/2003 Tominaga et al.
2012/0213774 A1 8/2012 Fertig et al.

FOREIGN PATENT DOCUMENTS

| CN | 110045131 A | 7/2019 |
| CN | 110357963 A | 10/2019 |
| JP | 2014-508520 A | 4/2014 |
| JP | 2015-523967 A | 8/2015 |
| WO | WO 2012/113813 A1 | 8/2012 |
| WO | WO 2013/173761 A2 | 11/2013 |
| WO | WO 2014/025767 A1 | 2/2014 |

OTHER PUBLICATIONS

Anonymous. "International Nonproprietary Names for Pharmaceutical Substances (INN): Astegolimab", WHO Drug Information, 34(1), Apr. 9, 2020, pp. 23-24.
Fursov et al. "Monoclonal antibodies targeting ST2L Domain 1 or Domain 3 differentially modulate IL-33-induced cytokine release by human mast cell and basophilic cell lines", Molecular Immunology, 75(22), Jun. 2016, pp. 178-187.
Notification of Reasons for Rejection for Japanese Patent Application No. 2022-544124 dated Mar. 11, 2025, with English translation, 12 pages.
Rudikoff et al: "Single amino acid substitution altering antigen-binding specificity". Proceedings of the National Academy of Sciences USA, 79(6), Mar. 1, 1982; pp. 1979-1983.
Supplementary European Search Report for European Patent Application No. 21745196.2 dated Apr. 23, 2024, 15 pages.
Winkle et al: "Changing the antigen binding specificity by single point mutations of an anti-p24 (HIV-1) antibody", The Journal of Immunology, 165(8), Oct. 15, 2000, pp. 4505-4514.
International Search Report of PCT/CN2021/073009, Apr. 20, 2021, 12 pages.
International Written Opinion of PCT/CN2021/073009, Apr. 20, 2021, 8 pages.
Kelsen, Steven G. MD et al., "Astegolimab (anti-ST2) efficacy and safety in adults with severe asthma: A randomized clinical trial", J Allergy Clin Immunol; 148(3) (2021); https://doi.org/10.1016/j.jaci.2021.03.044 (9 pages).
Nnane, Ivo et al., "The first-in-human study of CNTO 7160, an anti-interleukin-33 receptor monoclonal antibody, in healthy subjects and patients with asthma or atopic dermatitis", Br J Clin Pharmacol (2020) 86:2507-2518; DOI: 10.1111/bcp.14361 (12 pages).

(Continued)

*Primary Examiner* — Robert S Landsman
(74) *Attorney, Agent, or Firm* — Lewis Roca Rothgerber Christie LLP

(57) ABSTRACT

Provided are an anti-ST2 antibody or a fragment thereof. The antibody or the fragment thereof can be specifically bound to human ST2, for inhibiting combination of IL-33 and human ST2, blocking an IL-33/ST2 intracellular signaling pathway, and inhibiting the promoting effect of different forms of IL-33 in cell-derived IL5, IL6 and 118 production. Compared with a known anti-ST2 antibody, this anti-ST2 antibody has higher biological activity, and can be used for preventing, treating or alleviating diseases related to ST2 expression or IL-33/ST2 pathway disorders.

22 Claims, 12 Drawing Sheets

Specification includes a Sequence Listing.

(56) References Cited

OTHER PUBLICATIONS

Yousuf, Ahmed et al., "Astegolimab, an anti-ST2, in chronic obstructive pulmonary disease (COPD-ST2OP): a phase 2a, placebo-controlled trial", Lancet Respir Med (2022) 10: 469-77; https://doi.org/10.1016/S2213-2600(21)00556-7 (9 pages).
English translation of Examples 13 and 14 and related Figures in CN2021108246423 (7 pages).

4-1

4-2

4-3

4-4

5-1

5-2

6-1

6-2

6-3

6-4

6-5

7-1

7-2

8-1

8-2

9-1

9-2

9-3

9-4

9-5

9-6

9-7

10-1

10-2

10-3

10-4

10-5

10-6

15-1

15-2

15-3

15-4

1

ANTI-ST2 ANTIBODY, ENCODING NUCLEIC ACID MOLECULES THEREOF AND METHODS OF USE THEREOF

CROSS-REFERENCE TO RELATED APPLICATIONS

The present application is a U.S. National Phase Patent Application of International Application Number PCT/CN2021/073009, filed on Jan. 21, 2021, which claims the priority benefit of Chinese Patent Application No. CN202010072085.X filed on 21 Jan. 2020, the entire content of each of which is hereby incorporated by reference.

SEQUENCE LISTING

The instant application contains a Sequence Listing submitted in ASCII format via EFS-web, and the entire content of the electronic submission of the sequence listing is incorporated by reference in its entirety for all purposes. The ASCII file is named "224785_seq_list_rev_ST25," was last modified on Jan. 23, 2023, and is 77,419 bytes in size.

TECHNICAL FIELD

The present invention relates to the field of antibody drugs, in particular to an antibody against human ST2 and use thereof in preparing a medicament.

BACKGROUND OF THE INVENTION

Interleukin 33 (IL-33) is a cytokine associated with IL-1 and IL-18, also known as NF-HEV or IL-1F11. ST2 (ST2L, IL-1RL1, T1, Fit-1, DER-4, IL-1R4 or ST2 alpha) is a binding receptor for IL-33, and is a member of Toll/IL-1 receptor family, expressed on the cell surface of a variety of immune cells, including lymphocytes, especially helper T cells, natural killer (NK) cells and natural killer-T (NKT) cells expressing IL-5 and IL-13, as well as many so-called innate immune cells, such as mast cells, basophils, eosinophils, macrophages and innate helper cells (also known as new immune cells (nuocytes) (Neill, Wong et al, 2010)).

ST2 can down-regulate the responsiveness of Toll-like receptors TLR2, TLR4 and TLR9, and can induce the release of Type 2 cytokines via activation by its ligand IL-33 and association with accessory protein IL-1RAcP. Relevant literatures have proposed models of the interaction between ST2, IL-33 and IL-1RAcP, and the interaction between IL-1R1 and IL-1RAcP(Lingel et al, Cell 17: 1398-1410, 2009; Wang et al, Nat Immunol, 11: 905-11, 2010).

IL-33 has been described as an "Alarmin" because it is present in the nuclei of epithelial and endothelial cells in its full-length form during homeostasis, but can be cleaved and released during cellular necrosis. Examples of IL-33-induced cellular responses include the production of inflammatory cytokines such as IL-5, IL-6, IL-13, TNF, IFN-7, and GM-CSF, and the production of chemokines such as CXCL8, CCL17, and CCL24. IL-33 has also been shown to enhance acute allergic reactions by potentiating mast cell and basophil activation triggered by IgE receptor signaling or other mast cell and basophil activators. IL-33 also enhances the recruitment, survival and adhesion properties of ST2-expressing immune cells and is therefore of great importance in the excitation and maintenance of cellular inflammation in local tissues.

Dysregulation of IL-33/ST2 pathway has been shown to be associated with a variety of immune-mediated diseases, including asthma, rheumatoid arthritis, inflammatory bowel disease, atopic dermatitis, allergic rhinitis, nasal polyps, and systemic sclerosis. Thus, therapeutic blockade of the IL-33/ST2 pathway may help to overcome hyperimmune responses. Inhibitors of this pathway mainly include IL33 antibodies (e.g., MEDI3506, ANB020, REGN3500, MT-2990, LY-3375880, PF-06817024) and ST2 antibodies (e.g., CNTO7160, AMG-282), being developed at clinical stages 1 and 2 for indications including allergic rhinitis, atopic dermatitis, chronic obstructive pulmonary disease, asthma, etc.

Presently, incidence rates of allergic inflammation and respiratory disease are gradually increasing, and medicines available on the market still are mainly glucocorticoids and β2 receptor agonists. Antibodies reported to date, although all are able to block the interaction of ST2 with its ligand, differ in biological activities produced. Differences in biological activity may lead to differences in clinical efficacy and dosage of the antibodies, and therefore there is still a need in the art for ST2 antibodies that provide high affinity, high stability, and high biological activity.

SUMMARY OF THE INVENTION

The technical problem to be solved by the present invention is to obtain a new high affinity antibody which binds ST2 and is suitable for the treatment of diseases or any indications related to the IL-33/ST2 pathway, by immunizing mice with human ST2 as immunogen, obtaining murine antibodies through B cell panning, and further antibody engineering and humanization techniques.

For the above technical problem, an object of the present invention is to provide an antibody or functional fragment thereof that specifically binds to ST2, and to provide uses thereof.

Technical solutions of the present invention are as follows.

As described herein, a "fragment" of an antibody as described in the present invention encompasses various functional or active fragments of the antibody, e.g., an antigen-binding portion thereof, such as Fab, F (ab') 2, or scFv.

In one aspect, the present invention provides an antibody or fragment thereof comprising a heavy chain variable region (VH) and a light chain variable region (VL), wherein the heavy chain variable region and light chain variable region comprise heavy chain CDR1 (H-CDR1), CDR2 (H-CDR2), CDR3 (H-CDR3) and light chain CDR1 (L-CDR1), CDR2 (L-CDR2), CDR3 (L-CDR3) from a heavy chain variable region and a light chain variable region shown in any one selected from the following combinations:

(I-1): the heavy chain variable region as shown in SEQ ID NO. 1 and the light chain variable region as shown in SEQ ID NO. 29;

(I-2): the heavy chain variable region as shown in SEQ ID NO. 2 and the light chain variable region as shown in SEQ ID NO. 30;

(I-3): the heavy chain variable region as shown in SEQ ID NO. 2 and the light chain variable region as shown in SEQ ID NO. 31;

(I-4): the heavy chain variable region as shown in SEQ ID NO. 3 and the light chain variable region as shown in SEQ ID NO. 30;

(I-5): the heavy chain variable region as shown in SEQ ID NO. 3 and the light chain variable region as shown in SEQ ID NO. 31;

(II-1): the heavy chain variable region as shown in SEQ ID NO. 4 and the light chain variable region as shown in SEQ ID NO. 32;

(II-2): the heavy chain variable region as shown in SEQ ID NO. 5 and the light chain variable region as shown in SEQ ID NO. 33;

(II-3): the heavy chain variable region as shown in SEQ ID NO. 5 and the light chain variable region as shown in SEQ ID NO. 34;

(II-4): the heavy chain variable region as shown in SEQ ID NO. 5 and the light chain variable region as shown in SEQ ID NO. 35;

(II-5): the heavy chain variable region as shown in SEQ ID NO. 6 and the light chain variable region as shown in SEQ ID NO. 33;

(II-6): the heavy chain variable region as shown in SEQ ID NO. 6 and the light chain variable region as shown in SEQ ID NO. 34;

(II-7): the heavy chain variable region as shown in SEQ ID NO. 6 and the light chain variable region as shown in SEQ ID NO. 35;

(III-1): the heavy chain variable region as shown in SEQ ID NO. 7 and the light chain variable region as shown in SEQ ID NO. 36;

(III-2): the heavy chain variable region as shown in SEQ ID NO. 8 and the light chain variable region as shown in SEQ ID NO. 37;

(III-3): the heavy chain variable region as shown in SEQ ID NO. 8 and the light chain variable region as shown in SEQ ID NO. 38;

(III-4): the heavy chain variable region as shown in SEQ ID NO. 9 and the light chain variable region as shown in SEQ ID NO. 37;

(III-5): the heavy chain variable region as shown in SEQ ID NO. 9 and the light chain variable region as shown in SEQ ID NO. 38;

(IV-1): the heavy chain variable region as shown in SEQ ID NO. 10 and the light chain variable region as shown in SEQ ID NO. 39;

(IV-2): the heavy chain variable region as shown in SEQ ID NO. 11 and the light chain variable region as shown in SEQ ID NO. 40;

(IV-3): the heavy chain variable region as shown in SEQ ID NO. 11 and the light chain variable region as shown in SEQ ID NO. 41;

(IV-4): the heavy chain variable region as shown in SEQ ID NO. 12 and the light chain variable region as shown in SEQ ID NO. 40;

(IV-5): the heavy chain variable region as shown in SEQ ID NO. 12 and the light chain variable region as shown in SEQ ID NO. 41;

(IV-6): the heavy chain variable region as shown in SEQ ID NO. 13 and the light chain variable region as shown in SEQ ID NO. 40;

(IV-7): the heavy chain variable region as shown in SEQ ID NO. 13 and the light chain variable region as shown in SEQ ID NO. 41;

(IV-8): the heavy chain variable region as shown in SEQ ID NO. 14 and the light chain variable region as shown in SEQ ID NO. 40;

(IV-9): the heavy chain variable region as shown in SEQ ID NO. 14 and the light chain variable region as shown in SEQ ID NO. 41;

(V-1): the heavy chain variable region as shown in SEQ ID NO. 15 and the light chain variable region as shown in SEQ ID NO. 42;

(V-2): the heavy chain variable region as shown in SEQ ID NO. 16 and the light chain variable region as shown in SEQ ID NO. 43;

(V-3): the heavy chain variable region as shown in SEQ ID NO. 16 and the light chain variable region as shown in SEQ ID NO. 44;

(V-4): the heavy chain variable region as shown in SEQ ID NO. 16 and the light chain variable region as shown in SEQ ID NO. 45;

(V-5): the heavy chain variable region as shown in SEQ ID NO. 17 and the light chain variable region as shown in SEQ ID NO. 43;

(V-6): the heavy chain variable region as shown in SEQ ID NO. 17 and the light chain variable region as shown in SEQ ID NO. 44;

(V-7): the heavy chain variable region as shown in SEQ ID NO. 17 and the light chain variable region as shown in SEQ ID NO. 45;

(V-8): the heavy chain variable region as shown in SEQ ID NO. 18 and the light chain variable region as shown in SEQ ID NO. 43;

(V-9): the heavy chain variable region as shown in SEQ ID NO. 18 and the light chain variable region as shown in SEQ ID NO. 44;

(V-10): the heavy chain variable region as shown in SEQ ID NO. 18 and the light chain variable region as shown in SEQ ID NO. 45;

(V-11): the heavy chain variable region as shown in SEQ ID NO. 19 and the light chain variable region as shown in SEQ ID NO. 43;

(V-12): the heavy chain variable region as shown in SEQ ID NO. 19 and the light chain variable region as shown in SEQ ID NO. 44;

(V-13): the heavy chain variable region as shown in SEQ ID NO. 19 and the light chain variable region as shown in SEQ ID NO. 45;

(VI-1): the heavy chain variable region as shown in SEQ ID NO. 20 and the light chain variable region as shown in SEQ ID NO. 46;

(VI-2): the heavy chain variable region shown as SEQ ID NO. 21 and the light chain variable region shown as SEQ ID NO. 47;

(VI-3): the heavy chain variable region as shown in SEQ ID NO. 21 and the light chain variable region as shown in SEQ ID NO. 48;

(VI-4): the heavy chain variable region as shown in SEQ ID NO. 22 and the light chain variable region as shown in SEQ ID NO. 47;

(VI-5): the heavy chain variable region as shown in SEQ ID NO. 22 and the light chain variable region as shown in SEQ ID NO. 48;

(VI-6): the heavy chain variable region as shown in SEQ ID NO. 23 and the light chain variable region as shown in SEQ ID NO. 47;

(VI-7): the heavy chain variable region as shown in SEQ ID NO. 23 and the light chain variable region as shown in SEQ ID NO. 48;

(VI-8): the heavy chain variable region as shown in SEQ ID NO. 24 and the light chain variable region as shown in SEQ ID NO. 47;

(VI-9): the heavy chain variable region as shown in SEQ ID NO. 24 and the light chain variable region as shown in SEQ ID NO. 48;

(VII-1): the heavy chain variable region as shown in SEQ ID NO. 25 and the light chain variable region as shown in SEQ ID NO. 49;

(VII-2): the heavy chain variable region as shown in SEQ ID NO. 26 and the light chain variable region as shown in SEQ ID NO. 52;

(VII-3): the heavy chain variable region shown as SEQ ID NO. 26 and the light chain variable region shown as SEQ ID NO. 53;

(VII-4): the heavy chain variable region as shown in SEQ ID NO. 26 and the light chain variable region as shown in SEQ ID NO. 50;

(VII-5): the heavy chain variable region shown as SEQ ID NO. 26 and the light chain variable region shown as SEQ ID NO. 51;

(VII-6): the heavy chain variable region shown as SEQ ID NO. 27 and the light chain variable region shown as SEQ ID NO. 52;

(VII-7): the heavy chain variable region shown as SEQ ID NO. 27 and the light chain variable region shown as SEQ ID NO. 53;

(VII-8): the heavy chain variable region shown as SEQ ID NO. 27 and the light chain variable region shown as SEQ ID NO. 50;

(VII-9): the heavy chain variable region shown as SEQ ID NO. 27 and the light chain variable region shown as SEQ ID NO. 51;

(VII-10): the heavy chain variable region as shown in SEQ ID NO. 28 and the light chain variable region as shown in SEQ ID NO. 52;

(VII-11): the heavy chain variable region as shown in SEQ ID NO. 28 and the light chain variable region as shown in SEQ ID NO. 53;

(VII-12): the heavy chain variable region as shown in SEQ ID NO. 28 and the light chain variable region as shown in SEQ ID NO. 50; and (VII-13): the heavy chain variable region as shown in SEQ ID NO. 28 and the light chain variable region as shown in SEQ ID NO. 51.

Based on the given amino acid sequences of the light and heavy chain variable regions as above, those skilled in the art can routinely determine the amino acid sequences of the heavy and light chain CDRs contained therein. For example, according to particular embodiments of the present invention, CDRs in the variable region amino acid sequences are determined using Kabat, IMGT, ABM and Chotia numbering schemes. Light and heavy chain CDRs and combinations thereof obtained by other methods known in the art are also encompassed within the scope of the present invention.

Preferably, the heavy chain variable region and the light chain variable region comprise heavy chain CDRs and light chain CDRs shown in any one selected from the following combinations: (I) H-CDR1 (GYSITSDYAWN), H-CDR2 (YIDYSGSTTYNPSLKS), H-CDR3 (TVIDSMDY) as shown in SEQ ID NOs. 56, 63, 70 sequentially; and, L-CDR1 (RASKSVSTSGHSYMH), L-CDR2 (LASNLES), L-CDR3 (QHSREFPFT) as shown in SEQ ID NOs. 85, 93, 97 sequentially;

(II-1): H-CDR1 (GYSITSDYAWD), H-CDR2 (YIRYSGDTYYNPSLKS), H-CDR3 (TMMDTMDY) as shown in SEQ ID NOs. 57, 64, 71 sequentially; and, L-CDR1 (RASKSVSTSGNSYMH), L-CDR2 (LASNLES), L-CDR3 (QHSREFPLT) as shown in SEQ ID NOs. 86, 93, 98 sequentially;

(II-2): H-CDR1 (GYSITSDYAWD), H-CDR2 (YIRYSGDTYYNPSLKS), H-CDR3 (TMMDTMDY) as shown in SEQ ID NOs. 57, 64, 71 sequentially; and, L-CDR1 (RASKSVSTSGNTYMH), L-CDR2 (LASNLES), L-CDR3 (QHSREFPLT) as shown in SEQ ID NOs. 87, 93, 98 sequentially;

(III): H-CDR1 (GFSLSTSGMGVG), H-CDR2 (HIWWDDVKQYNPALKS), H-CDR3 (IG-GDYDYFDF) as shown in SEQ ID NOs. 58, 65, 72 sequentially; and, L-CDR1 (RASESVEYSGTSLMQ), L-CDR2 (VASNVES), L-CDR3 (QQSRKVPWT) as shown in SEQ ID NOs. 88, 94, 99 sequentially;

(IV-1): H-CDR1 (GYTFTDSEMY), H-CDR2 (AID-PETGDTAFNQKFKG), H-CDR3 (AF-DNDNDDGFAY) as shown in SEQ ID NOs. 59, 66, 73 sequentially; and, L-CDR1 (SASSSVNYMH), L-CDR2 (DTSKLAS), L-CDR3 (QQWSSNPLT) as shown in SEQ ID NOs. 89, 95, 100 sequentially;

(IV-2): H-CDR1 (GYTFTDSEMY), H-CDR2 (AID-PETGDTAFNQKFKG), H-CDR3 (AFDNDNDE-GFAY) as shown in SEQ ID NOs. 59, 66, 74 sequentially; and, L-CDR1 (SASSSVNYMH), L-CDR2 (DTSKLAS), L-CDR3 (QQWSSNPLT) as shown in SEQ ID NOs. 89, 95, 100 sequentially;

(IV-3): H-CDR1 (GYTFTDSEMY), H-CDR2 (AID-PETGDTAFNQKFKG), H-CDR3 (AFDNDNDDA-FAY) as shown in SEQ ID NOs. 59, 66, 75 sequentially; and, L-CDR1 (SASSSVNYMH), L-CDR2 (DTSKLAS), L-CDR3 (QQWSSNPLT) as shown in SEQ ID NOs. 89, 95, 100 sequentially;

(V-1): H-CDR1 (GYTFTDYELH), H-CDR2 (TID-PETGDTVYNQKFKA), H-CDR3 (AFYNDYDD-GFAY) as shown in SEQ ID NOs. 60, 67, 76 sequentially; and, L-CDR1 (SVSSSVSYMH), L-CDR2 (DTSKLAS), L-CDR3 (QQWNSSPLT) as shown in SEQ ID NOs. 90, 95, 101 sequentially;

(V-2): H-CDR1 (GYTFTDYELH), H-CDR2 (TID-PETGDTVYNQKFKA), H-CDR3 (AFYNDYDD-GFAY) as shown in SEQ ID NOs. 60, 67, 76 sequentially; and, L-CDR1 (SVSSSVSYMH), L-CDR2 (DTSKLAS), L-CDR3 (QQWNTSPLT) as shown in SEQ ID NOs. 90, 95, 102 sequentially;

(V-3): H-CDR1 (GYTFTDYELH), H-CDR2 (TID-PETGDTVYNQKFKA), H-CDR3 (AFYNDYDE-GFAY) as shown in SEQ ID NOs. 60, 67, 77 sequentially; and, L-CDR1 (SVSSSVSYMH), L-CDR2 (DTSKLAS), L-CDR3 (QQWNSSPLT) as shown in SEQ ID NOs. 90, 95, 101 sequentially;

(V-4): H-CDR1 (GYTFTDYELH), H-CDR2 (TID-PETGDTVYNQKFKA), H-CDR3 (AFYNDYDE-GFAY) as shown in SEQ ID NOs. 60, 67, 77 sequentially; and, L-CDR1 (SVSSSVSYMH), L-CDR2 (DTSKLAS), L-CDR3 (QQWNTSPLT) as shown in SEQ ID NOs. 90, 95, 102 sequentially;

(V-5): H-CDR1 (GYTFTDYELH), H-CDR2 (TID-PETGDTVYNQKFKA), H-CDR3 (AFYNDYDDA-FAY) as shown in SEQ ID NOs. 60, 67, 78 sequentially; and, L-CDR1 (SVSSSVSYMH), L-CDR2 (DTSKLAS), L-CDR3 (QQWNSSPLT) as shown in SEQ ID NOs. 90, 95, 101 sequentially;

(V-6): H-CDR1 (GYTFTDYELH), H-CDR2 (TID-PETGDTVYNQKFKA), H-CDR3 (AFYNDYDDA-FAY) as shown in SEQ ID NOs. 60, 67, 78 sequentially; and, L-CDR1 (SVSSSVSYMH), L-CDR2 (DTSKLAS), L-CDR3 (QQWNTSPLT) as shown in SEQ ID NOs. 90, 95, 102 sequentially;

(VI-1): H-CDR1 (GYRFTDSEMH), H-CDR2 (TID-PETGGTVYNQKFKG), H-CDR3 (AFYND-FDDGFAY) as shown in SEQ ID NOs. 61, 68, 79 sequentially; and, L-CDR1 (SASTSVSYMH), L-CDR2 (DTSKLAS), L-CDR3 (QQWSSNPLT) as shown in SEQ ID NOs. 91, 95, 100 sequentially;

(VI-2): H-CDR1 (GYRFTDSEMH), H-CDR2 (TID-PETGGTVYNQKFKG), H-CDR3 (AFYNDFDE-GFAY) as shown in SEQ ID NOs. 61, 68, 80 sequentially; and, L-CDR1 (SASTSVSYMH), L-CDR2 (DTSKLAS), L-CDR3 (QQWSSNPLT) as shown in SEQ ID NOs. 91, 95, 100 sequentially;

(VI-3): H-CDR1 (GYRFTDSEMH), H-CDR2 (TID-PETGGTVYNQKFKG), H-CDR3 (AFYNDFDDA-FAY) as shown in SEQ ID NOs. 61, 68, 81 sequentially; and, L-CDR1 (SASTSVSYMH), L-CDR2 (DTSKLAS), L-CDR3 (QQWSSNPLT) as shown in SEQ ID NOs. 91, 95, 100 sequentially;

(VII-1): H-CDR1 (GYTFINYGMN), H-CDR2 (WIN-TYIGEPTYGDNFKG), H-CDR3 (EGDGFAY) as shown in SEQ ID NOs. 62, 69, 82 sequentially; and, L-CDR1 (KSSQSLLYSGNQNNYLA), L-CDR2 (GASTRES), L-CDR3 (QNDHSYPYT) as shown in SEQ ID NOs. 92, 96, 103 sequentially;

(VII-2): H-CDR1 (GYTFINYGMN), H-CDR2 (WIN-TYIGEPTYGDNFKG), H-CDR3 (EGEGFAY) as shown in SEQ ID NOs. 62, 69, 83 sequentially; and, L-CDR1 (KSSQSLLYSGNQNNYLA), L-CDR2 (GASTRES), L-CDR3 (QNDHSYPYT) as shown in SEQ ID NOs. 92, 96, 103 sequentially; and (VII-3): H-CDR1 (GYTFINYGMN), H-CDR2 (WINTYIGEP-TYGDNFKG), H-CDR3 (EGDAFAY) as shown in SEQ ID NOs. 62, 69, 84 sequentially; and, L-CDR1 (KSSQSLLYSGNQNNYLA), L-CDR2 (GASTRES), L-CDR3 (QNDHSYPYT) as shown in SEQ ID NOs. 92, 96, 103 sequentially.

In particular, the antibody or fragment thereof of the present invention comprises at least a heavy chain variable region and a light chain variable region, which both comprise the above CDRs and framework regions (FRs) therebetween, and in which domains in the heavy chain variable region and light chain variable region are arranged as follows: FR1-CDR1-FR2-CDR2-FR3-CDR3-FR4. Further optionally, the up to 25% difference with respect to amino acid sequence due to the "at least 75% identity" may be present in any framework region in the heavy chain variable region or the light chain variable region, or in any domain or sequence in the antibody or fragment thereof of the present invention other than the heavy chain variable region and the light chain variable region. The difference may be resulted from amino acid deletion, addition or substitution at any position, and the substitution may be conservative substitution or non-conservative substitution.

Preferably, the heavy chain variable region comprises an amino acid sequence as shown in any one of SEQ ID NO. 1 to SEQ ID NO. 28 or an amino acid sequence having at least 75% identity to the amino acid sequence as shown; and/or, the light chain variable region comprises an amino acid sequence as shown in any one of SEQ ID NO. 29 to SEQ ID NO. 53 or an amino acid sequence having at least 75% identity to the amino acid sequence as shown.

According to a particular embodiment of the present invention, the antibody or fragment thereof of the present invention comprises a heavy chain variable region and a light chain variable region as shown in any one selected from the following combinations:

(I-1): the heavy chain variable region as shown in SEQ ID NO. 1 and the light chain variable region as shown in SEQ ID NO. 29;

(I-2): the heavy chain variable region as shown in SEQ ID NO. 2 and the light chain variable region as shown in SEQ ID NO. 30;

(I-3): the heavy chain variable region as shown in SEQ ID NO. 2 and the light chain variable region as shown in SEQ ID NO. 31;

(I-4): the heavy chain variable region as shown in SEQ ID NO. 3 and the light chain variable region as shown in SEQ ID NO. 30;

(I-5): the heavy chain variable region as shown in SEQ ID NO. 3 and the light chain variable region as shown in SEQ ID NO. 31;

(II-1): the heavy chain variable region as shown in SEQ ID NO. 4 and the light chain variable region as shown in SEQ ID NO. 32;

(II-2): the heavy chain variable region as shown in SEQ ID NO. 5 and the light chain variable region as shown in SEQ ID NO. 33;

(II-3): the heavy chain variable region as shown in SEQ ID NO. 5 and the light chain variable region as shown in SEQ ID NO. 34;

(II-4): the heavy chain variable region as shown in SEQ ID NO. 5 and the light chain variable region as shown in SEQ ID NO. 35;

(II-5): the heavy chain variable region as shown in SEQ ID NO. 6 and the light chain variable region as shown in SEQ ID NO. 33;

(II-6): the heavy chain variable region as shown in SEQ ID NO. 6 and the light chain variable region as shown in SEQ ID NO. 34;

(II-7): the heavy chain variable region as shown in SEQ ID NO. 6 and the light chain variable region as shown in SEQ ID NO. 35;

(III-1): the heavy chain variable region as shown in SEQ ID NO. 7 and the light chain variable region as shown in SEQ ID NO. 36;

(III-2): the heavy chain variable region as shown in SEQ ID NO. 8 and the light chain variable region as shown in SEQ ID NO. 37;

(III-3): the heavy chain variable region as shown in SEQ ID NO. 8 and the light chain variable region as shown in SEQ ID NO. 38;

(III-4): the heavy chain variable region as shown in SEQ ID NO. 9 and the light chain variable region as shown in SEQ ID NO. 37;

(III-5): the heavy chain variable region as shown in SEQ ID NO. 9 and the light chain variable region as shown in SEQ ID NO. 38;

(IV-1): the heavy chain variable region as shown in SEQ ID NO. 10 and the light chain variable region as shown in SEQ ID NO. 39;

(IV-2): the heavy chain variable region as shown in SEQ ID NO. 11 and the light chain variable region as shown in SEQ ID NO. 40;

(IV-3): the heavy chain variable region as shown in SEQ ID NO. 11 and the light chain variable region as shown in SEQ ID NO. 41;

(IV-4): the heavy chain variable region as shown in SEQ ID NO. 12 and the light chain variable region as shown in SEQ ID NO. 40;

(IV-5): the heavy chain variable region as shown in SEQ ID NO. 12 and the light chain variable region as shown in SEQ ID NO. 41;

(IV-6): the heavy chain variable region as shown in SEQ ID NO. 13 and the light chain variable region as shown in SEQ ID NO. 40;

(IV-7): the heavy chain variable region as shown in SEQ ID NO. 13 and the light chain variable region as shown in SEQ ID NO. 41;

(IV-8): the heavy chain variable region as shown in SEQ ID NO. 14 and the light chain variable region as shown in SEQ ID NO. 40;

(IV-9): the heavy chain variable region as shown in SEQ ID NO. 14 and the light chain variable region as shown in SEQ ID NO. 41;

(V-1): the heavy chain variable region as shown in SEQ ID NO. 15 and the light chain variable region as shown in SEQ ID NO. 42;

(V-2): the heavy chain variable region as shown in SEQ ID NO. 16 and the light chain variable region as shown in SEQ ID NO. 43;

(V-3): the heavy chain variable region as shown in SEQ ID NO. 16 and the light chain variable region as shown in SEQ ID NO. 44;

(V-4): the heavy chain variable region as shown in SEQ ID NO. 16 and the light chain variable region as shown in SEQ ID NO. 45;

(V-5): the heavy chain variable region as shown in SEQ ID NO. 17 and the light chain variable region as shown in SEQ ID NO. 43;

(V-6): the heavy chain variable region as shown in SEQ ID NO. 17 and the light chain variable region as shown in SEQ ID NO. 44;

(V-7): the heavy chain variable region as shown in SEQ ID NO. 17 and the light chain variable region as shown in SEQ ID NO. 45;

(V-8): the heavy chain variable region as shown in SEQ ID NO. 18 and the light chain variable region as shown in SEQ ID NO. 43;

(V-9): the heavy chain variable region as shown in SEQ ID NO. 18 and the light chain variable region as shown in SEQ ID NO. 44;

(V-10): the heavy chain variable region as shown in SEQ ID NO. 18 and the light chain variable region as shown in SEQ ID NO. 45;

(V-11): the heavy chain variable region as shown in SEQ ID NO. 19 and the light chain variable region as shown in SEQ ID NO. 43;

(V-12): the heavy chain variable region as shown in SEQ ID NO. 19 and the light chain variable region as shown in SEQ ID NO. 44;

(V-13): the heavy chain variable region as shown in SEQ ID NO. 19 and the light chain variable region as shown in SEQ ID NO. 45;

(VI-1): the heavy chain variable region as shown in SEQ ID NO. 20 and the light chain variable region as shown in SEQ ID NO. 46;

(VI-2): the heavy chain variable region shown as SEQ ID NO. 21 and the light chain variable region shown as SEQ ID NO. 47;

(VI-3): the heavy chain variable region as shown in SEQ ID NO. 21 and the light chain variable region as shown in SEQ ID NO. 48;

(VI-4): the heavy chain variable region as shown in SEQ ID NO. 22 and the light chain variable region as shown in SEQ ID NO. 47;

(VI-5): the heavy chain variable region as shown in SEQ ID NO. 22 and the light chain variable region as shown in SEQ ID NO. 48;

(VI-6): the heavy chain variable region as shown in SEQ ID NO. 23 and the light chain variable region as shown in SEQ ID NO. 47;

(VI-7): the heavy chain variable region as shown in SEQ ID NO. 23 and the light chain variable region as shown in SEQ ID NO. 48;

(VI-8): the heavy chain variable region as shown in SEQ ID NO. 24 and the light chain variable region as shown in SEQ ID NO. 47;

(VI-9): the heavy chain variable region as shown in SEQ ID NO. 24 and the light chain variable region as shown in SEQ ID NO. 48;

(VII-1): the heavy chain variable region as shown in SEQ ID NO. 25 and the light chain variable region as shown in SEQ ID NO. 49;

(VII-2): the heavy chain variable region as shown in SEQ ID NO. 26 and the light chain variable region as shown in SEQ ID NO. 52;

(VII-3): the heavy chain variable region shown as SEQ ID NO. 26 and the light chain variable region shown as SEQ ID NO. 53;

(VII-4): the heavy chain variable region as shown in SEQ ID NO. 26 and the light chain variable region as shown in SEQ ID NO. 50;

(VII-5): the heavy chain variable region shown as SEQ ID NO. 26 and the light chain variable region shown as SEQ ID NO. 51;

(VII-6): the heavy chain variable region shown as SEQ ID NO. 27 and the light chain variable region shown as SEQ ID NO. 52;

(VII-7): the heavy chain variable region shown as SEQ ID NO. 27 and the light chain variable region shown as SEQ ID NO. 53;

(VII-8): the heavy chain variable region shown as SEQ ID NO. 27 and the light chain variable region shown as SEQ ID NO. 50;

(VII-9): the heavy chain variable region shown as SEQ ID NO. 27 and the light chain variable region shown as SEQ ID NO. 51;

(VII-10): the heavy chain variable region as shown in SEQ ID NO. 28 and the light chain variable region as shown in SEQ ID NO. 52;

(VII-11): the heavy chain variable region as shown in SEQ ID NO. 28 and the light chain variable region as shown in SEQ ID NO. 53;

(VII-12): the heavy chain variable region as shown in SEQ ID NO. 28 and the light chain variable region as shown in SEQ ID NO. 50; and (VII-13): the heavy chain variable region as shown in SEQ ID NO. 28 and the light chain variable region as shown in SEQ ID NO. 51.

The antibody or fragment thereof provided by the present invention binds to ST2, preferably mammalian ST2, more preferably primate ST2, further preferably human or cynomolgus ST2, in particular human ST2. Experiments proved that the antibody provided by the present invention has following activities:

(1) specifically binding to human ST2;

(2) inhibiting binding of IL-33 to human ST2;

(3) blocking intracellular signaling pathway of IL-33/ST2;

(4) inhibiting promoting effect of different forms of IL-33 on cellular production of IL5;

(5) inhibiting promoting effect of IL-33 on cellular production of IL5, IL6 and IL8; and (6) having a long half-life in vivo.

Generally, the antibody or fragment thereof provided by the present invention is in any form, e.g., a monoclonal antibody, a single chain antibody, a diabody, a single domain antibody, a nanobody, a fully or partially humanized antibody, or a chimeric antibody and the like, or a fragment thereof. Preferably, the antibody is an IgA, IgD, IgE, IgG or IgM, more preferably IgG1, IgG2 or IgG4 antibody.

Preferably, the fragment is a functionally active fragment of the antibody which is capable of specifically binding to ST2 or any portion thereof. More preferably, the fragment is single-chain variable fragment (scFv), bivalent single-chain variable fragment (BsFv), disulfide-stabilized Fv fragment (dsFv), (disulfide-stabilized Fv fragment)$_2$ (dsFv)$_2$, antigen-binding fragment (Fab), Fab' fragment, F(ab')$_2$ fragment, or variable fragment (Fv) of the antibody.

Further preferably, the antibody or fragment thereof further comprises a human or murine constant region, preferably a human or murine heavy chain constant region (CH) and/or light chain constant region (CL). Preferably, the antibody or fragment thereof comprises a heavy chain and a light chain; more preferably, the antibody comprises two heavy chains and two light chains.

Preferably, the antibody or fragment thereof comprises a heavy chain constant region selected from the group consisting of constant regions of IgG, IgA, IgM, IgD and IgE and/or a kappa or lambda type light chain constant region. According to a particular embodiment of the present invention, the antibody comprises a heavy chain constant region which is of IgG1, IgG2, or IgG4 subtype; or, the antibody comprises a light chain constant region which is of kappa subtype. Further preferably, the heavy chain constant region comprises an amino acid sequence as shown in SEQ ID NO: 54 or an amino acid sequence having at least 75% identity to the amino acid sequence as shown; and the light chain constant region comprises an amino acid sequence as shown in SEQ ID NO: 55 or an amino acid sequence having at least 75% identity to the amino acid sequence as shown.

The at least 75% identity described in the context of the present invention may be any percent identity greater than or equal to 75%, such as at least 75%, at least 80%, preferably at least 85%, more preferably at least 90%, further preferably at least 91%, 92%, 93%, 94%, 95%, 96%, 97%, 98%, or even 99% identity.

According to a particular embodiment of the present invention, the present invention particularly preferably provides antibodies as follows:

antibody named as "5888-116-H0L1", having a heavy chain variable region as shown in SEQ ID NO. 11 and a light chain variable region as shown in SEQ ID NO. 41;

antibody named as "5888-153-H0L1", having a heavy chain variable region as shown in SEQ ID NO. 16 and a light chain variable region as shown in SEQ ID NO. 44; and antibody named as "5886-156-H1L0", having a heavy chain variable region as shown in SEQ ID NO. 3 and a light chain variable region as shown in SEQ ID NO. 30;

and each antibody above has a heavy chain constant region as shown in SEQ ID NO. 54 and a light chain constant region as shown in SEQ ID NO. 55. The antibodies are monoclonal antibodies, each comprising two heavy chains and two light chains.

Based on the antibody or fragment thereof provided by the present invention, the present invention also provides a conjugate or fusion protein comprising the antibody or fragment thereof of the present invention. The conjugate or fusion protein may comprise other moieties, such as a cell surface receptor, a small molecule compound such as an amino acids and a carbohydrate, a small molecule polymer or any other moiety that modifies the antibody of the present invention, or even an active protein or polypeptide, that are chemically or physically bound to the antibody or fragment thereof of the present invention.

In another aspect, the present invention provides a nucleic acid molecule comprising a nucleotide sequence encoding a heavy chain CDR, a light chain CDR, a heavy chain variable region, a light chain variable region, a heavy chain or a light chain comprised in any antibody or fragment thereof according to the present invention.

In yet another aspect, the present invention provides a vector comprising the nucleic acid molecule of the present invention. The vector can be a eukaryotic expression vector, a prokaryotic expression vector, an artificial chromosome, a phage vector and the like.

The vector or nucleic acid molecule of the present invention may be used to transform or transfect a host cell or in any way enter a host cell for antibody preservation or expression, etc. Thus, in a further aspect, the present invention provides a host cell comprising the nucleic acid molecule and/or the vector according to the present invention, or transformed or transfected with the nucleic acid molecule and/or the vector according to the present invention. The host cell may be any prokaryotic or eukaryotic cell, such as a bacterial or insect, fungus, plant or animal cell.

According to the disclosure of the present invention, the antibody or fragment thereof as well as accordingly the conjugate or fusion protein, the nucleic acid molecule, the vector, and/or the host cell provided by the present invention can be obtained using any conventional techniques known in the art. The antibody or fragment thereof, the conjugate or fusion protein, the nucleic acid molecule, the vector, and/or the host cell may be contained in a composition, more particularly in a pharmaceutical composition, e.g., a pharmaceutical preparation, to be used for various purposes as actually needed.

Thus, in still a further aspect, the present invention also provides a composition comprising an antibody or fragment thereof, a conjugate or fusion protein, a nucleic acid molecule, a vector, and/or a host cell according to the present invention. Preferably, the composition is a pharmaceutical composition which optionally comprises a pharmaceutically acceptable excipient.

The present invention also provides following related uses of the subject matters described above based on the antibody or fragment thereof which is capable of specifically binding to ST2 or any portion thereof.

In a further aspect, the present invention provides the use of the antibody or fragment thereof, the conjugate or fusion protein, the nucleic acid molecule, the vector, the host cell and/or the composition in the manufacture of a medicament for preventing, treating or ameliorating a disease; preferably, the disease is associated with expression of ST2 or dysregulation of IL-33/ST2 pathway. Preferably, the disease is an inflammatory disease or an autoimmune disease; more preferably, the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea.

In addition, the present invention provides a method for preventing, treating or ameliorating a disease, including administering to a subject in need thereof the antibody or fragment thereof, the conjugate or fusion protein, the nucleic acid molecule, the vector, the host cell and/or the composition of the present invention, and optionally an additional drug or means. Preferably, the disease is associated with expression of ST2 or dysregulation of IL-33/ST2 pathway. Preferably, the disease is an inflammatory disease or an autoimmune disease; more preferably, the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea. The optional additional drug or means refers to any other hormonal or immunomodulatory drugs or means that can be administered in combination with the antibody or fragment thereof, the conjugate or fusion protein, the nucleic acid molecule, the vector, the host cell and/or the composition of the present invention, such as glucocorticoid, Mepolizumab, Dupilumab, Tezepelumab and the like. The co-administration of the two may be in any way, including simultaneously, sequentially or at intervals. The subject is a mammal, preferably a primate, further preferably a human or a cynomolgus monkey; preferably, the subject is a human.

Accordingly, the present invention also provides a pharmaceutical combination comprising the antibody or fragment thereof, the conjugate or fusion protein, the nucleic acid molecule, the vector, the host cell and/or the composition of the present invention, and optionally an additional drug. The optional additional drug refers to any other hormonal or immunomodulatory drugs or means that can be administered in combination with the antibody or fragment thereof, the conjugate or fusion protein, the nucleic acid molecule, the vector, the host cell and/or the composition of the present invention, such as glucocorticoid, Mepolizumab, Dupilumab, Tezepelumab and the like.

The present invention also provides a method for detecting or diagnosing a disease including contacting the antibody or fragment thereof, the conjugate or fusion protein, the nucleic acid molecule, the vector, the host cell and/or the composition with a sample from a subject. Preferably, the disease is associated with expression of ST2 or dysregulation of IL-33/ST2 pathway. Preferably, the disease is an inflammatory disease or an autoimmune disease; more preferably, the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea. The subject is a mammal, preferably a primate, further preferably a human or a cynomolgus monkey; preferably, the subject is a human.

In yet another aspect, the present invention provides a kit comprising the antibody or fragment thereof, the conjugate or fusion protein, the nucleic acid molecule, the vector, the host cell and/or the composition of the present invention. The kit may be used for detection or diagnosis, e.g. in the method for detecting or diagnosing a disease as described above.

In the present invention, mice were immunized with human ST2, culture supernatants were obtained through B cell panning, and positive clones were obtained via ELISA and further functional assay screening; further, humanized antibodies were obtained by humanizing murine antibodies through antibody engineering. Through activity screening experiments on in vitro ligand binding by the antibodies, inhibiting ligand from activating effector cells in vitro by the antibodies, and inhibiting ligand from promoting effector cells to produce 1L5, 1L6, 1L8 and the like by the antibodies, affinity determination of the antibodies, as well as drug metabolism experiments in animals and the like, the antibodies of the present invention are proved to have higher biological activities compared with currently available anti-ST2 antibodies.

BRIEF DESCRIPTION OF THE DRAWINGS

Embodiments of the present invention are described in detail below with reference to the attached figures, in which:

FIG. 1 to FIG. 5 show inhibition rates in KU812-NF-κB reporter gene assay of the B cell clones from mice differently numbered, in which FIG. 1: mouse numbered 5883; FIG. 2: mouse numbered 5884; FIG. 3: mouse numbered 5886; FIG. 4: mouse numbered 5887; and FIG. 5: mouse numbered 5888.

DETAILED DESCRIPTION OF PREFERRED EMBODIMENTS

Figure 1:
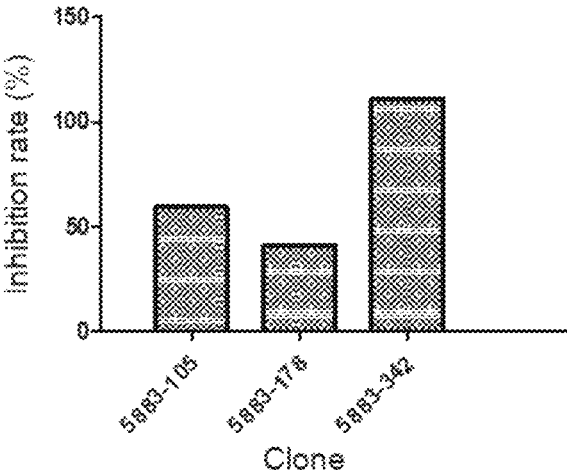
Figure 2:
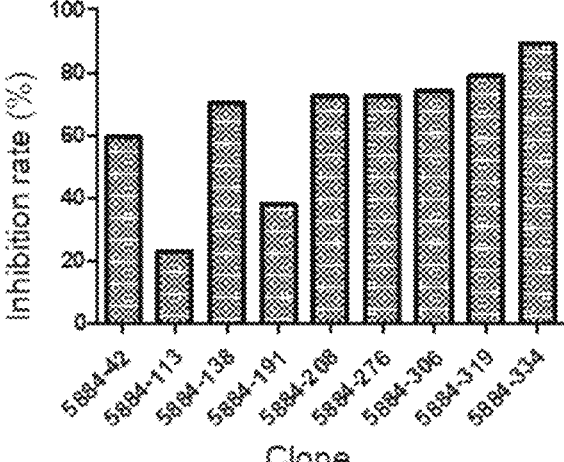
Figure 3:
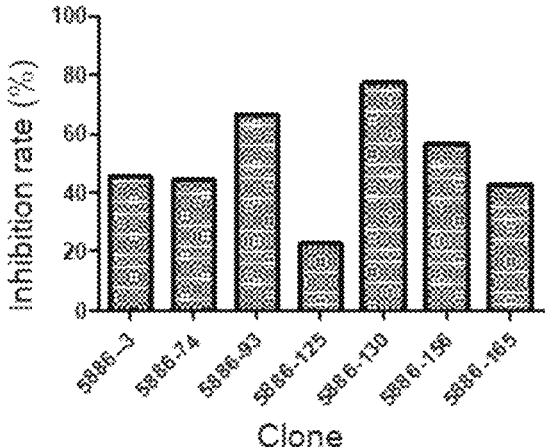
Figure 4:
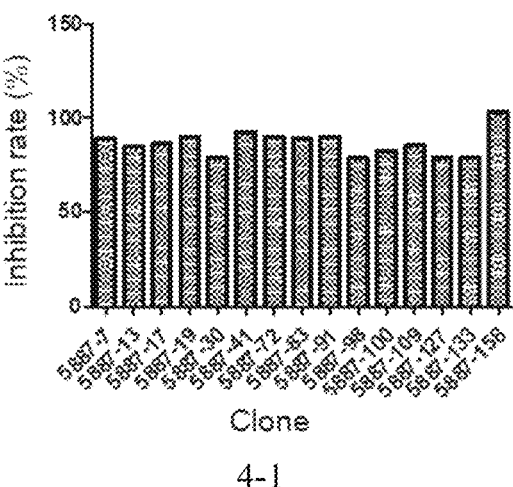
Figure 4:
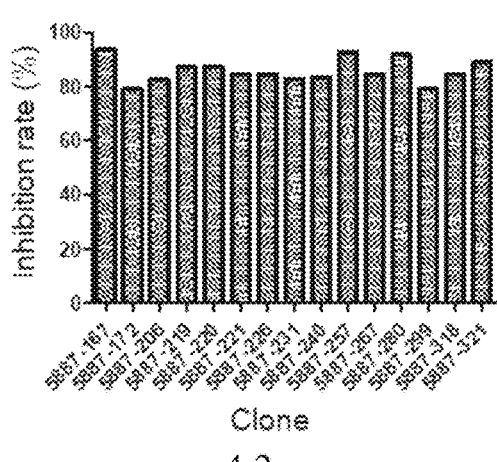
Figure 4:
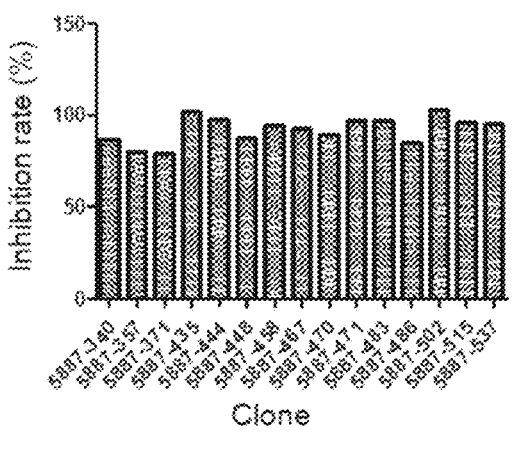
Figure 4:
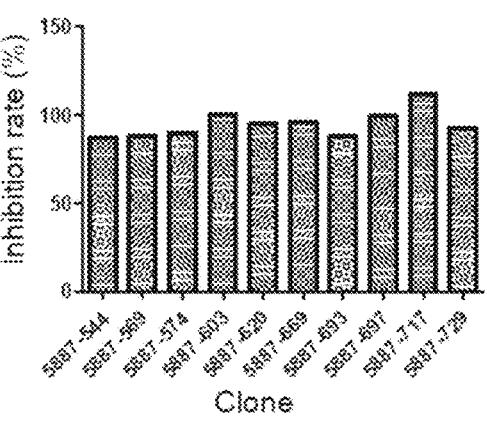
Figure 5:
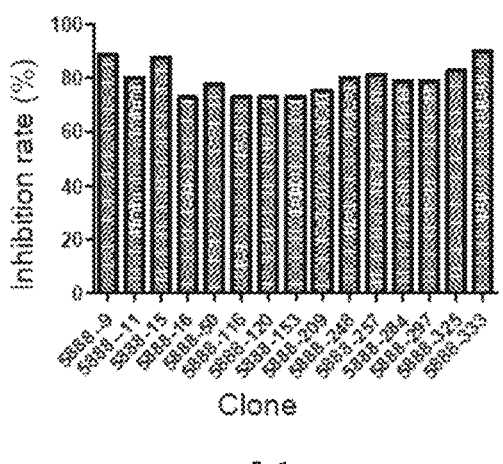
Figure 5:
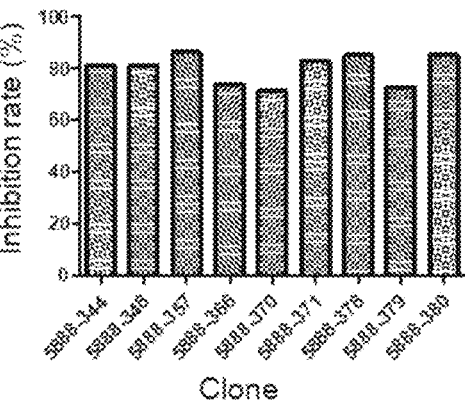

The present invention is illustrated below with reference to specific examples. It will be understood by those skilled in the art that these examples are merely illustrative of the present invention and do not limit the scope of the present invention in any way.

Experimental procedures in the following examples are all conventional ones, unless otherwise specified. Raw materials and reagents used in the following examples are all commercially available products, unless otherwise specified.

Human ST2: NP_003847.2 (Met1-Phe328)

Human ST2-his: human ST2 fused with a 6-histidine tag at the C-termius

Human ST2-fc: human ST2 fused with a human IgG1 Fc tag at the C-termius

Human 1L33: NP_254274.1 (Ser112-Thr270)

Human IL33-his: human IL33 fused with a 6-histidine tag at the C-termius Oxidized human IL33-his: human IL-33-his was diluted to 300 μg/ml with IMDM, incubated at 37° C. for 18 hours, and then purified using S75 16: 600 Superdex column (GE Healthcare)

Reduced human IL33-his: human IL33-his with Cys208Ser and Cys259Ser

Control antibody CNTO7160: having a heavy chain as shown in SEQ ID NO. 104 and a light chain as shown in SEQ ID NO. 105

Cyno ST2: XP_005575214.1 (Met1-Cys331)

Cyno ST2-fc: cyno ST2 fused with a human IgG1 Fc tag at the C-terminus

Mouse ST2: NP_001020773.1 (Met1-Arg332)

Mouse ST2-fc: mouse ST2 fused with a human IgG1 Fc tag at the C-terminus

Example 1: Murine Antibody Screening

1.1 Animal Immunization

CHO-K1 cells were used to express human ST2-his, and then 6 BALB/c mice were immunized according to a conventional immunization program with Freund's adjuvant. The immunization was performed in two batches of mice including 3 mice in each, with two weeks between the batches. Each batch of mice was immunized 4 times, tested by ELISA using the human ST2-his, and terminally immunized if any mouse had a serum titer >1:100,000; and 3-4 days later spleens were collected.

1.2 B Cell Panning and Culture

Feeder cells were plated using culture medium into 4 10-cm dishes (Corning, cat. 430167) 2 days before formal experiment was performed, treated with 25 μg/mL MMC for 6 h 1 day before the formal experiment, and then plated in 96-well plates (Corning, cat. 3599) at 10000 cells/well and 100 μL/well. In addition, the antigen human ST2-his was coated in 6-well plates overnight at 4° C.

The collected spleens of the immunized mice were ground, filtered, and centrifuged, and red blood cell lysate was added therein to remove red blood cells. The treatment with red blood cell lysate was repeated for many times until no obvious red blood cells existed; and DC cells were then removed from the splenocytes. Splenocytes obtained from one spleen were uniformly plated into the 6-well plates coated with the antigen above for panning, and B cells after antigen-panning were collected with trypsin, counted and plated into the 96-well plates coated with feeder cells above. The cells were cultured at 37° C., 5% $CO_2$ for 10-14 days, and B cell culture supernatants in the wells in which obvious clones formed were collected for the following screening.

1.3 Screening of Supernatants Containing Murine Antibodies (1) ELISA Screening of Murine Antibodies Binding to Human ST2-his:

The immunogen human ST2-his as above was diluted with a coating buffer to 1 μg/mL, added into ELISA plates at 50 μL/well and coated overnight at 4° C. Next day, the coated plates were taken, washed with PBST for 3 times, and then incubated using a blocking buffer at room temperature for 1 hr. Subsequently, the plates were washed with PBST for 3 times again; and B cell culture supernatants were added into the ELISA plates and incubated at room temperature for 1 hr. The plates were washed with PBST for 3 times, and then a goat anti-mouse secondary antibody (1:10000) was added at 50 μL/well into the plates which subsequently were incubated at room temperature for 1 hr. The 96-well plates were washed with PBST for 3 times, and TMB was added at 50 μL/well to develop color in dark for 10 min. Afterwards, 2 M sulfuric acid was added to stop reaction; and OD values at 450 nm were read by a microplate reader.

Detection results showed that B cell clones from two mice numbered 5883 and 5884 had a positive rate above 97% in the ELISA for screening murine antibodies binding to human ST2-his, in which a OD value 10 times greater than that of negative control (blank medium) was used as a judgment standard for positivity.

1.4 KU812-NF-κB Reporter Gene Assay Screening $1\times10^6$ KU812 cells in logarithmic growth phase was taken, centrifugally washed once, and resuspended in 20 μL of buffer R from Neon Transfection System 10 μL Kit. 1 μg of pGL4.32[luc2P/NF-κB-RE/Hygro] vector was added into the cells which were then transfected by electric shocking at 1000 V, and 50 ms once. After the transfection, Hygromycin B was used to perform pressure screening, and a cell strain KU812/NF-κB-1 # was finally obtained.

Human IL33-his was diluted to 1 μg/mL with culture medium and mixed with each of the B cell culture supernatants at a 1:1 ratio to obtain test samples. In addition, a negative control sample (diluted human IL33-his mixed with blank medium at a 1:1 ratio) and a positive control sample (diluted human IL33-his mixed with 1 μg/mL CNTO7160 at a 1:1 ratio) were prepared. The samples were added into 384-well plates, each at 20 μL/well. KU812/NF-κB-1 # cells in logarithmic growth phase were taken, added into the 384-well plates at 20000/well and 20 μL/well, and incubated overnight (16-24 hrs) at 37° C., 5% $CO_2$. Subsequently, reagent Bright-glo was added into the 384-well plates at 40 μL/well, and the plates were shaked for 3 min, detected by a microplate reader, and RLU values were read.

Inhibition rate of each clone was calculated with reference to the values of the negative control and the positive control, and results are shown in FIG. 1 to FIG. 5.

Example 2: Antibody Engineering

2.1 Sequencing of the Antibodies in the B Cells mRNAs were extracted from the B cell clones using PureLink™ RNA Mini Kit according to the instructions therein, subpackaged and stored at −80° C. The extracted mRNAs were used as templates and reverse transcribed into cDNAs using PrimeScript™ II 1st Strand cDNA Synthesis Kit according to the instructions therein, which were then subpackaged and stored at −80° C.

VH and VL sequences were amplified using Ex Taq enzyme and using the heavy chain VH and light chain VL amplifying primers shown in Tables 1-1 and 1-2, with the above cDNAs as templates; and then ligated into pMD18T vector for sequencing.

TABLE 1-1

| Primers for amplifying heavy chain VH | | |
|---|---|---|
| VH-F-Mix1 | OVH1 (SEQ ID NO: 106) | SAGGTCCAGCTGCAGCAGYYTGG |
| | OVH2 (SEQ ID NO: 107) | CAGGTRCAGCTGAAGSAGTCAGG |
| | OVH3 (SEQ ID NO: 108) | GAKGTGCAGCTTCAGCAGTCRGG |
| | OVH5 (SEQ ID NO: 109) | GAVGTGAWGCTGGTGGAGTCTGR |
| | OVH11 (SEQ ID NO: 110) | GAAGTGCAGCTGTTGGAGACTGG |
| | OVH14 (SEQ ID NO: 111) | GAGGTTCAGCTGCAGCAGTCTGK |
| | OVH15 (SEQ ID NO: 112) | CAGGTTCACCTACAACAGTCTGG |

TABLE 1-1-continued

| Primers for amplifying heavy chain VH | | | |
|---|---|---|---|
| VH-F-Mix2 | OVH4 | (SEQ ID NO: 113) | GAGGTGAAGCTTCTCGAGTCTGG |
| | OVH7 | (SEQ ID NO: 114) | GAGGTGAAGCTGRTGGARTCTGR |
| | OVH8 | (SEQ ID NO: 115) | CAGGTTACTCTGAAAGAGTCTGG |
| | OVH9 | (SEQ ID NO: 116) | CAGATCCAGTTGGYGCAGTCTGG |
| | OVH10 | (SEQ ID NO: 117) | GAGGTGCAGCTTGTTGAGWCTGG |
| | OVH12 | (SEQ ID NO: 118) | CAGATGCAGCTTCAGGAGTCAGG |
| | OVH13 | (SEQ ID NO: 119) | GAAGTGAAGCTTGAGGAGTCTGG |
| VH-F-Mix3 | OVH6a | (SEQ ID NO: 120) | GAAGTGMAMTTKSWGCAGTCTGG |
| | OVH6b | (SEQ ID NO: 121) | GAGGTGMAMTTKSWGCTGTCTGG |
| | OVH6c | (SEQ ID NO: 122) | GATGTGMAMTTKSWGCAGTCTGG |
| | OVH6d | (SEQ ID NO: 123) | GAAGTGMAMTTKSWGCTGTCTGG |
| | OVH6e | (SEQ ID NO: 124) | GAGGTGMAMTTKSWGCAGTCTGG |
| | OVH6f | (SEQ ID NO: 125) | GATGTGMAMTTKSWGCTGTCTGG |
| | OVH6g | (SEQ ID NO: 126) | GAAGTGMAMTTKSWGGAGTCTGG |
| | OVH6h | (SEQ ID NO: 127) | GAGGTGMAMTTKSWGGTGTCTGG |
| | OVH6i | (SEQ ID NO: 128) | GATGTGMAMTTKSWGGAGTCTGG |
| | OVH6j | (SEQ ID NO: 129) | GAAGTGMAMTTKSWGGTGTCTGG |
| | OVH6K | (SEQ ID NO: 130) | GAGGTGMAMTTKSWGGAGTCTGG |
| | OVH6l | (SEQ ID NO: 131) | GATGTGMAMTTKSWGGTGTCTGG |
| VH-R-Mix | HF-1 | (SEQ ID NO: 132) | GAGGAAACGGTGACCGTGGT |
| | HF-2 | (SEQ ID NO: 133) | GAGGAGACTGTGAGAGTGGT |
| | HF-3 | (SEQ ID NO: 134) | GCAGAGACAGTGACCAGAGT |
| | HF-4 | (SEQ ID NO: 135) | GAGGAGACGGTGACTGAGGT |

TABLE 1-2

| Primers for amplifying light chain VL | | | |
|---|---|---|---|
| VLk-F-Mix1 | OVK1 | (SEQ ID NO: 136) | GATGYTKTKVTGACCCAAACTCC |
| | OVK3 | (SEQ ID NO: 137) | RACATTGTGCTGACMCAATCTCC |
| | OVK4a | (SEQ ID NO: 138) | SAAAWTGTKCTCWCCCAGTCTCC |
| | OVK4b | (SEQ ID NO: 139) | SAAAWTCTKCTCWCCCAGTCTCC |
| | OVK4c | (SEQ ID NO: 140) | SAAAWTTTKCTCWCCCAGTCTCC |
| | OVK6a | (SEQ ID NO: 141) | ARCATTGTGATGACCCAGWCTCA |
| | OVK6b | (SEQ ID NO: 142) | ARCATTGTGATGACCCAGWCTCC |
| | OVK6c | (SEQ ID NO: 143) | GRCATTGTGATGACCCAGWCTCA |
| | OVK6d | (SEQ ID NO: 144) | GRCATTGTGATGACCCAGWCTCC |
| | OVK10 | (SEQ ID NO: 145) | GATATCCAGATGACACAGACTAC |
| | OVK14 | (SEQ ID NO: 146) | GAMATCMWGATGACCCARTCTCC |
| VLk-F-Mix2 | OVK2a | (SEQ ID NO: 147) | GATATTGTGATRACBCAGGYTGA |
| | OVK2b | (SEQ ID NO: 148) | GATATTGTGATRACBCAGGYTGC |

TABLE 1-2-continued

| Primers for amplifying light chain VL | | |
|---|---|---|
| | OVK5a (SEQ ID NO: 149) | GAYATYCTGATRACRCAGTCTCC |
| | OVK5b (SEQ ID NO: 150) | GAYATYGTGATRACRCAGTCTCC |
| | OVK5c (SEQ ID NO: 151) | GAYATYTTGATRACRCAGTCTCC |
| | OVK5d (SEQ ID NO: 152) | GAYATYCTGCTRACRCAGTCTCC |
| | OVK5e (SEQ ID NO: 153) | GAYATYGTGCTRACRCAGTCTCC |
| | OVK5f (SEQ ID NO: 154) | GAYATYTTGCTRACRCAGTCTCC |
| | OVK7 (SEQ ID NO: 155) | GACATTGTGATGACTCAGTCTCC |
| | OVK9 (SEQ ID NO: 156) | GACATCCAGATGAYYCAGTCTCC |
| | OVK11-16 (SEQ ID NO: 157) | GATGTCCAGATRAYYCAGTCTCC |
| | OVK12-13 (SEQ ID NO: 158) | GACATCCAGATGACWCARTCTYC |
| | OVK15-19 (SEQ ID NO: 159) | GACATCCAGATGAMMCAGTCTCC |
| | OVK17 (SEQ ID NO: 160) | GAAACAACTGTGACCCAGTCTCC |
| | OVK18 (SEQ ID NO: 161) | ACTGGAGAAACAACACAGGCTCC |
| VLk-F-Mix3 | OVK8a (SEQ ID NO: 162) | RAMATTATGWTGWCACAGTCTAC |
| | OVK8b (SEQ ID NO: 163) | RAMATTATGWTGWCACAGTCTAT |
| | OVK8c (SEQ ID NO: 164) | RAMATTGTGWTGWCACAGTCTAC |
| | OVK8d (SEQ ID NO: 165) | RAMATTGTGWTGWCACAGTCTAT |
| | OVK8e (SEQ ID NO: 166) | RAMATTTTGWTGWCACAGTCTAC |
| | OVK8f (SEQ ID NO: 167) | RAMATTTTGWTGWCACAGTCTAT |
| | OVK8g (SEQ ID NO: 168) | RAMATTATGWTGWCACAGTCTCC |
| | OVK8h (SEQ ID NO: 169) | RAMATTATGWTGWCACAGTCTCT |
| | OVK8i (SEQ ID NO: 170) | RAMATTGTGWTGWCACAGTCTCC |
| | OVK8j (SEQ ID NO: 171) | RAMATTGTGWTGWCACAGTCTCT |
| | OVK8k (SEQ ID NO: 172) | RAMATTTTGWTGWCACAGTCTCC |
| | OVK8l (SEQ ID NO: 173) | RAMATTTTGWTGWCACAGTCTCT |
| VLk-R-Mix | LF1 (SEQ ID NO: 174) | ACGTTTGATTTCCAGCTTGG |
| | LF2 (SEQ ID NO: 175) | ACGTTTTATTTCCAGCTTGG |
| | LF4 (SEQ ID NO: 176) | ACGTTTTATTTCCAACTTTG |
| | LF5 (SEQ ID NO: 177) | ACGTTTCAGCTCCAGCTTGG |

2.2 Recombinant Expression and Screening of Murine Antibodies (1) Recombinant Expression of Murine Antibodies Light and heavy chains from the same clone (e.g., shown in FIG. 1 to FIG. 5) were co-transfected in pairs into CHO-K1 cells, and 24 h after the transfection, 10 μg/mL MSX was added for pressure screening. The cells, after cell density and viability recovered, were inoculated for Feed-batch expression, and supernatants when the expression was completed were centrifuged and purified by protein A. Antibodies obtained were used for quantitative screening after antibody concentrations were determined by BCA method.

Murine antibodies were named after the cell clone number from which their light and heavy chains (H+L) were derived.

For example, murine antibody "5883-105H+L" represents a murine antibody derived from the cell clone numbered 5883-105, the heavy chain of which is 5883-105H, and the light chain of which is 5883-105L.

(2) Screening of Binding Activity of Murine Antibodies to Human ST2

Human ST2-his was diluted with a coating buffer to 1 μg/mL, added into plates at 50 μL/well, and coated overnight at 4° C. Next day, the coated plates were taken, washed with PBST for 3 times, and then incubated using a blocking buffer at room temperature for 1 hr. Subsequently, the plates were washed with PBST for 3 times again. Starting at 100 ng/mL, each murine antibody was diluted 3-fold to obtain serial dilutions of 8 concentrations in total which were then added into the 96-well plates at 50 μL/well. The plates were incubated at room temperature for 1 hr, washed with PBST for 3 times; and then a goat anti-mouse secondary antibody (1:10000) was added at 50 μL/well into the 96-well plates which subsequently were incubated at room temperature for 1 hr. The 96-well plates were washed with PBST for 3 times, and TMVB was added at 50 μL/well to develop color in dark for 10 min. Afterwards, 2 M sulfuric acid was added to stop reaction; and GD values at 450 nm were read by a micro-plate reader. Results are shown in Table 2.

TABLE 2

Binding activity of murine antibodies to human ST2 and relative activity of the antibodies compared with CNTO7160

| Antibody | $EC_{50}$ (ng/mL) | Relative activity (%) |
|---|---|---|
| 5883-105H + L | 13.52 | 84.99 |
| 5883-178H2 + L1 | 9.64 | 119.19 |
| 5883-178H2 + L2 | 4.93 | 233.02 |
| 5884-113H1 + L2 | 9.61 | 149.71 |
| 5884-113H2 + L1 | 12.56 | 114.57 |
| 5884-138H1 + L1 | 16.33 | 88.12 |
| 5884-42H + L | 9.71 | 136.87 |
| 5884-191H1 + L1 | 9.43 | 140.95 |
| 5884-276H + L | 7.49 | 177.51 |
| 5884-306H1 + L3 | 6.05 | 225.66 |
| 5884-306H3 + L1 | 8.99 | 151.82 |
| 5884-319H1 + L1 | 4.80 | 284.20 |
| 5884-334H1 + L1 | 11.89 | 134.57 |
| 5886-3H + L | 9.79 | 163.40 |
| 5886-93H + L | 10.94 | 146.25 |
| 5886-125H1 + L1 | 7.46 | 171.94 |
| 5886-125H1 + L2 | 68.70 | 18.66 |
| 5886-125H2 + L2 | 6.86 | 186.88 |
| 5886-130H1 + L1 | 25.52 | 66.26 |
| 5886-130H1 + L2 | 22.89 | 73.88 |
| 5886-130H2 + L2 | 11.08 | 152.62 |
| 5886-165H + L | 21.10 | 100.14 |
| 5886-156H + L | 16.12 | 131.08 |
| 5887-7H1 + L2 | 17.16 | 151.57 |
| 5887-30H1 + L1 | 140.30 | 18.54 |
| 5887-30H2 + L2 | 1.73 | 1501.73 |
| 5887-41H + L | 26.57 | 97.89 |
| 5887-83H2 + L1 | 18.86 | 137.91 |
| 5887-91H + L | 28.21 | 56.86 |
| 5887-98H1 + L2 | 26.87 | 59.69 |
| 5887-267H3 + L3 | 11.72 | 136.86 |
| 5887-280H1 + L1 | 23.95 | 66.97 |
| 5887-98H3 + L3 | 20.34 | 78.86 |
| 5887-98H5 + L1 | 16.36 | 98.04 |
| 5887-172H3 + L3 | 24.00 | 57.04 |
| 5887-221H2 + L1 | 26.45 | 51.76 |
| 5887-240H + L | 13.53 | 101.18 |
| 5887-257H2 + L1 | 22.40 | 61.12 |
| 5887-267H1 + L2 | 14.46 | 94.67 |
| 5887-318H2 + L | 5.11 | 211.59 |
| 5887-321H2 + L1 | 5.52 | 195.80 |
| 5887-340H2 + L1 | 8.54 | 126.57 |
| 5887-458H + L | 11.45 | 94.41 |
| 5887-467H2 + L1 | 12.25 | 88.24 |
| 5887-483H3 + L2 | 15.32 | 58.02 |
| 5887-537H3 + L1 | 12.28 | 72.38 |
| 5888-209H + L | 4.45 | 128.75 |
| 5888-284H2 + L | 5.91 | 96.89 |
| 5888-344H3 + L1 | 5.85 | 97.95 |
| 5888-378H + L | 7.21 | 79.41 |
| 5887-127H3 + L2 | 5.74 | 208.20 |
| 5887-167H + L | 12.92 | 92.41 |
| 5887-220H + L | 13.83 | 86.33 |
| 5887-357H1 + L | 10.74 | 111.17 |
| 5887-502H + L | 43.91 | 35.00 |
| 5887-515H + L | 42.68 | 36.01 |
| 5887-537H1 + L2 | 46.62 | 32.97 |
| 5887-603H1 + L | 35.35 | 32.73 |
| 5887-669H1 + L2 | 24.16 | 47.89 |
| 5887-669H2 + L1 | 17.89 | 64.67 |
| 5887-717H3 + L1 | 25.27 | 45.79 |
| 5888-15H2 + L2 | 15.72 | 116.35 |
| 5888-116H1 + L1 | 28.84 | 63.42 |

TABLE 2-continued

Binding activity of murine antibodies to human ST2 and relative activity of the antibodies compared with CNTO7160

| Antibody | $EC_{50}$ (ng/mL) | Relative activity (%) |
|---|---|---|
| 5888-120H2 + L1 | 27.04 | 67.64 |
| 5888-153H1 + L2 | 20.93 | 87.39 |
| 5888-297H1 + L1 | 19.22 | 95.16 |
| 5888-357H + L | 11.30 | 123.54 |
| 5888-366H1 + L2 | 17.23 | 65.82 |
| 5888-379H1 + L2 | 29.49 | 33.90 |
| 5888-380H1 + L2 | 23.29 | 42.93 |
| 5887-219H1 + L1 | 21.26 | 39.78 |
| 5888-380H2 + L1 | 58.62 | 14.43 |
| 5888-248H1 + L1 | 25.54 | 33.11 |
| 5887-544H1 + L1 | 17.65 | 47.92 |

(3) Blocking Assay Screening of Murine Antibodies on the Binding of IL33 to Human ST2

Human ST2-fc was diluted with a coating buffer to 10 μg/mL, added into 96-well plates at 50 μL/well and coated overnight in a refrigerator at 4° C. The coated plates were washed with PB ST for 3 times, and then were incubated at room temperature for 1 h after a blocking buffer was added into the plates at 100 μL/well; and subsequently the plates were washed with PBST for 3 times again. Human IL33-his was diluted to 200 ng/mL in diluting solution; and each murine antibody was diluted in diluting solution to 200 μg/mL, and then starting at 200% g/mL was diluted 3-fold to obtain serial dilutions of 8 concentrations in total. The diluted human HL33-his and each diluted murine antibody were mixed in a 1:1 ratio, and then the mixtures were added into the 96-well plates at 50 μL/well which were subse-quently incubated at room temperature for 1 hr. The plates were washed with PBST for 3 times, and then a His-tagged secondary antibody (1:2500) was added at 50 μL/well and the plates were incubated at room temperature for 1 hr. The 96-well plates were washed with PBST for 3 times again, and TMVB was added at 50 μL/well to develop color in dark for 10 min. Afterwards, 2 M sulfuric acid was added at 100 μL/well to stop reaction; and GD values at 450 nm and 650 nm were read by a microplate reader. Results are shown in Table 3.

TABLE 3

Blocking assay screening of murine antibodies on the binding of IL33 to human ST2 and relative activity of the antibodies compared with CNTO7160

| Antibody | $IC_{50}$ (μg/mL) | Relative activity (%) |
|---|---|---|
| 5883-105H + L | 1.61 | 93.56 |
| 5883-178H2 + L1 | N/A | N/A |
| 5883-178H2 + L2 | N/A | N/A |
| 5884-113H1 + L2 | 2.75 | 30.67 |
| 5884-113H2 + L1 | N/A | N/A |
| 5884-138H1 + L1 | 1.18 | 71.23 |
| 5884-42H + L | 1.48 | 56.99 |
| 5884-191H1 + L1 | 1.97 | 42.73 |
| 5884-276H + L | 1.15 | 66.66 |
| 5884-306H1 + L3 | 0.69 | 110.69 |
| 5884-306H3 + L1 | N/A | N/A |
| 5884-319H1 + L1 | 0.60 | 127.18 |
| 5884-334H1 + L1 | 1.28 | 59.24 |
| 5886-3H + L | 0.90 | 88.75 |
| 5886-93H + L | 0.71 | 113.12 |
| 5886-125H1 + L1 | 0.08 | 977.04 |
| 5886-125H1 + L2 | 0.62 | 129.35 |
| 5886-125H2 + L2 | 0.78 | 102.34 |
| 5886-130H1 + L1 | 0.83 | 104.39 |

23

TABLE 3-continued

Blocking assay screening of murine antibodies on the binding of IL33 to human ST2 and relative activity of the antibodies compared with CNTO7160

| Antibody | $IC_{50}$ (µg/mL) | Relative activity (%) |
|---|---|---|
| 5886-130H1 + L2 | 0.64 | 136.26 |
| 5886-130H2 + L2 | 0.87 | 99.46 |
| 5886-165H + L | 1.39 | 62.77 |
| 5886-156H + L | 1.14 | 76.58 |
| 5887-7H1 + L2 | 1.09 | 97.88 |
| 5887-30H1 + L1 | 1.74 | 61.02 |
| 5887-30H2 + L2 | 0.06 | 1792.88 |
| 5887-41H + L | 1.29 | 82.72 |
| 5887-83H2 + L1 | 1.22 | 86.99 |
| 5887-91H + L | 1.92 | 58.53 |
| 5887-98H1 + L2 | N/A | N/A |
| 5887-267H3 + L3 | N/A | N/A |
| 5887-280H1 + L1 | 1.41 | 79.80 |
| 5887-98H3 + L3 | 0.39 | 290.15 |
| 5887-98H5 + L1 | 1.00 | 112.54 |
| 5887-172H3 + L3 | 0.95 | 117.88 |
| 5887-221H2 + L1 | 1.27 | 88.49 |
| 5887-240H + L | 0.87 | 128.60 |
| 5887-257H2 + L1 | 1.75 | 64.19 |
| 5887-267H1 + L2 | N/A | N/A |
| 5887-318H2 + L | 0.88 | 104.58 |
| 5887-321H2 + L1 | 0.93 | 99.16 |
| 5887-340H2 + L1 | N/A | N/A |
| 5887-458H + L | 1.04 | 89.15 |
| 5887-467H2 + L1 | 1.63 | 56.95 |
| 5887-483H3 + L2 | N/A | N/A |
| 5887-537H3 + L1 | 0.99 | 93.54 |
| 5888-209H + L | 0.95 | 97.63 |
| 5888-284H2 + L | N/A | N/A |
| 5888-344H3 + L1 | 1.42 | 65.08 |
| 5888-378H + L | 1.02 | 90.64 |
| 5887-127H3 + L2 | 0.93 | 78.83 |
| 5887-167H + L | 0.76 | 96.54 |
| 5887-220H + L | 2.53 | 29.07 |
| 5887-357H1 + L | 1.13 | 64.78 |
| 5887-502H + L | 0.91 | 80.81 |
| 5887-515H + L | 0.97 | 75.35 |
| 5887-537H1 + L2 | 0.49 | 149.34 |
| 5887-603H + L | 0.80 | 92.19 |
| 5887-669H1 + L2 | N/A | N/A |
| 5887-669H2 + L1 | 0.82 | 89.58 |
| 5887-717H3 + L1 | N/A | N/A |
| 5888-15H2 + L2 | 0.87 | 67.02 |
| 5888-116H1 + L1 | 0.90 | 65.22 |
| 5888-120H2 + L1 | 1.03 | 56.63 |
| 5888-153H1 + L2 | 0.75 | 78.36 |
| 5888-297H1 + L1 | 0.85 | 68.97 |
| 5888-357H + L | 0.62 | 94.69 |
| 5888-366H1 + L2 | N/A | N/A |
| 5888-379H1 + L2 | 0.83 | 70.09 |
| 5888-380H1 + L2 | 0.92 | 63.67 |
| 5887-219H1 + L1 | 1.39 | 63.87 |
| 5888-380H2 + L1 | N/A | N/A |
| 5888-248H1 + L1 | 1.43 | 62.13 |
| 5887-544H1 + L1 | 0.96 | 92.26 |

(4) Screening of Murine Antibodies on the Activation of KU812-NF-κB Reporter Gene by IL33

Human IL33-his was diluted with culture medium to 1 µg/mL. Each of murine antibodies and control antibody CNTO7160 was diluted with culture medium to 50 µg/mL, and then was diluted 3-fold to obtain serial dilutions of 12 concentrations in total. The antibodies were mixed with the diluted human IL33-his at a 1:1 ratio to obtain test samples. In addition, a negative control sample (diluted human IL33-his mixed with blank medium at a 1:1 ratio) and a positive control sample (blank medium) were prepared. The samples were added into 384-well plates, each at 20 µL/well.

KU812/NF-κB-1 # cells in logarithmic growth phase were centrifuged, transferred to fresh medium, and added into the 384-well plates above at 20000/well and 20 µL/well. The cells were incubated overnight (16-24 hrs) at 37° C., 5% $CO_2$. Subsequently, developer Bright-glo was added into the 384-well plates at 40 µL/well, and the plates were oscillated for 3 min, detected by a microplate reader, and RLU values were read. Results are shown in Table 4.

TABLE 4

Screening of murine antibodies on the activation of KU812-NF-κB reporter gene by IL33 and relative activity of the antibodies compared with CNTO7160

| Antibody | $IC_{50}$ (ng/mL) | Relative activity (%) |
|---|---|---|
| 5883-105H + L | 5.272 | 231.79 |
| 5883-178H2 + L1 | 30.46 | 40.12 |
| 5883-178H2 + L2 | 2.206 | 553.94 |
| 5884-113H1 + L2 | 153.4 | 8.66 |
| 5884-113H2 + L1 | 28111 | 0.05 |
| 5884-138H1 + L1 | 171.1 | 7.76 |
| 5884-42H + L | 219.8 | 6.04 |
| 5884-191H1 + L1 | 1543 | 0.86 |
| 5884-276H + L | 123.7 | 10.74 |
| 5884-306H1 + L3 | NA | NA |
| 5884-306H3 + L1 | NA | NA |
| 5884-319H1 + L1 | NA | NA |
| 5884-334H1 + L1 | 459.5 | 2.89 |
| 5886-3H + L | 83.54 | 15.90 |
| 5886-93H + L | 82.94 | 16.01 |
| 5886-125H1 + L1 | 30.22 | 43.94 |
| 5886-125H1 + L2 | NA | NA |
| 5886-125H2 + L2 | 228.9 | 5.80 |
| 5886-130H1 + L1 | NA | NA |
| 5886-130H1 + L2 | NA | NA |
| 5886-130H2 + L2 | 11.50 | 88.70 |
| 5886-165H + L | 92.00 | 11.09 |
| 5886-156H + L | 8.04 | 126.82 |
| 5887-7H1 + L2 | 29.91 | 4.38 |
| 5887-30H1 + L1 | 1.439 | 91.10 |
| 5887-30H2 + L2 | 3.13 | 45.68 |
| 5887-41H + L | 2.87 | 41.88 |
| 5887-83H2 + L1 | 36.8 | 3.56 |
| 5887-91H + L | N/A | N/A |
| 5887-280H1 + L1 | 6603 | 0.62 |
| 5887-172H3 + L3 | N/A | N/A |
| 5887-221H2 + L1 | 2797 | 1.46 |
| 5887-240H + L | N/A | N/A |
| 5887-257H2 + L1 | 123.2 | 33.07 |
| 5887-318H2 + L | N/A | N/A |
| 5887-321H2 + L1 | 8894 | 0.46 |
| 5887-458H + L | 1009 | 4.04 |
| 5887-467H2 + L1 | N/A | N/A |
| 5887-537H3 + L1 | 101.3 | 40.22 |
| 5888-209H + L | 119.9 | 33.98 |
| 5888-378H + L | 103.3 | 39.44 |
| 5887-127H3 + L2 | 154.70 | 162.12 |
| 5887-357H1 + L | 1296.00 | 19.35 |
| 5887-502H + L | 3693.00 | 6.79 |
| 5887-515H + L | 2584.00 | 9.71 |
| 5887-537H1 + L2 | 2536.00 | 9.89 |
| 5887-603H + L | 1131.00 | 22.18 |
| 5887-669H2 + L1 | 332.40 | 75.45 |
| 5888-15H2 + L2 | 173.20 | 144.80 |
| 5888-116H1 + L1 | 206.40 | 121.51 |
| 5888-120H2 + L1 | 161.90 | 154.91 |
| 5888-153H1 + L2 | 49.52 | 506.46 |
| 5888-297H1 + L1 | 56.56 | 443.42 |
| 5888-357H + L | 55.20 | 454.35 |
| 5888-379H1 + L2 | 390.80 | 64.18 |
| 5888-380H1 + L2 | 124.60 | 201.28 |
| 5887-167H + L | 147.90 | 133.54 |
| 5887-219H1 + L1 | N/A | N/A |
| 5887-544H1 + L1 | 335.40 | 11.43 |

(5) Affinity Screening of Murine Antibodies

On the basis of the results of the quantitative screenings of murine antibodies above together, 19 murine antibodies were selected for affinity determination and in vitro pharmacological study. The experiment on the interaction between the anti-human ST2 antibodies and human ST2-his was performed using Biacore X100, and was carried out at 25° C. in HBS-EP (1×) buffer (pH 7.4).

Each anti-human ST2 antibody was diluted to 10 nM and captured on the surface of a protein A chip (for a capture time of 60 s). Following the antibody capture, a solution of human ST2-his (2-fold gradient dilution from 11.8 nM to 0.7375 nM, 5 concentrations in total) was injected. Association was monitored for 4 min and dissociation for 10 min, and the sensor surface was regenerated by injecting a solution of glycine at pH 2.0. Data generated for kinetics and affinity assay were analyzed using BIAevaluation software. Kinetic data were analyzed using a simple 1:1 binding model and results are shown in Table 5.

TABLE 5

| Affinity of murine antibodies | | | |
| --- | --- | --- | --- |
| Antibody | ka (1/Ms) | kd (1/s) | KD (M) |
| 5883-105H + L | 1.59E+07 | 3.79E−03 | 2.39E−10 |
| 5886-130H2 + L2 | 2.62E+06 | 1.78E−03 | 6.79E−10 |
| 5886-156H + L | 2.37E+06 | 1.09E−03 | 4.61E−10 |
| 5887-30H2 + L2 | 6.95E+06 | 1.10E−02 | 1.58E−09 |
| 5887-41H + L | 1.10E+06 | 6.13E−04 | 5.60E−10 |
| 5887-257H2 + L1 | 1.09E+06 | 7.50E−04 | 6.89E−10 |
| 5887-537H3 + L1 | 5.01E+06 | 8.40E−04 | 1.68E−10 |
| 5888-209H + L | 9.85E+06 | 2.73E−03 | 2.77E−10 |
| 5888-378H + L | 1.07E+07 | 1.42E−03 | 1.34E−10 |
| 5887-127H3 + L2 | 4.23E+06 | 1.05E−03 | 2.47E−10 |
| 5887-167H + L | 1.24E+06 | 6.99E−04 | 5.63E−10 |
| 5888-15H2 + L2 | 5.16E+06 | 1.09E−03 | 2.10E−10 |
| 5888-116H1 + L1 | 9.87E+06 | 1.11E−03 | 1.13E−10 |
| 5888-120H2 + L1 | 1.29E+07 | 1.13E−03 | 8.75E−11 |
| 5888-153H1 + L2 | 9.17E+06 | 8.64E−04 | 9.43E−11 |
| 5888-297H1 + L1 | 1.02E+07 | 1.71E−03 | 1.68E−10 |
| 5888-357H + L | 4.38E+06 | 7.00E−04 | 1.60E−10 |
| 5888-379H1 + L2 | 9.57E+05 | 5.46E−04 | 5.71E−10 |
| 5888-380H1 + L2 | 7.13E+06 | 1.03E−03 | 1.45E−10 |
| CNTO7160 | 8.27E+05 | 5.39E−04 | 6.98E−10 |

(6) In Vitro Pharmacological Study of Murine Antibodies

Human IL33-his was diluted with culture medium to 80 ng/mL. Each murine antibody was diluted with culture medium to 40 μg/mL and then was diluted 4-fold to obtain serial dilutions of 8 concentrations in total. The diluted antibodies were mixed with the diluted human HL33-his at a 1:1 ratio, and the mixtures obtained were added into 96-well plates at 50 μL/well. KU812 cells in logarithmic growth phase were centrifuged, added into the 96-well plates at 100000/well and 50 μL/well, and then were incubated for 48 hrs.

Figure 6:
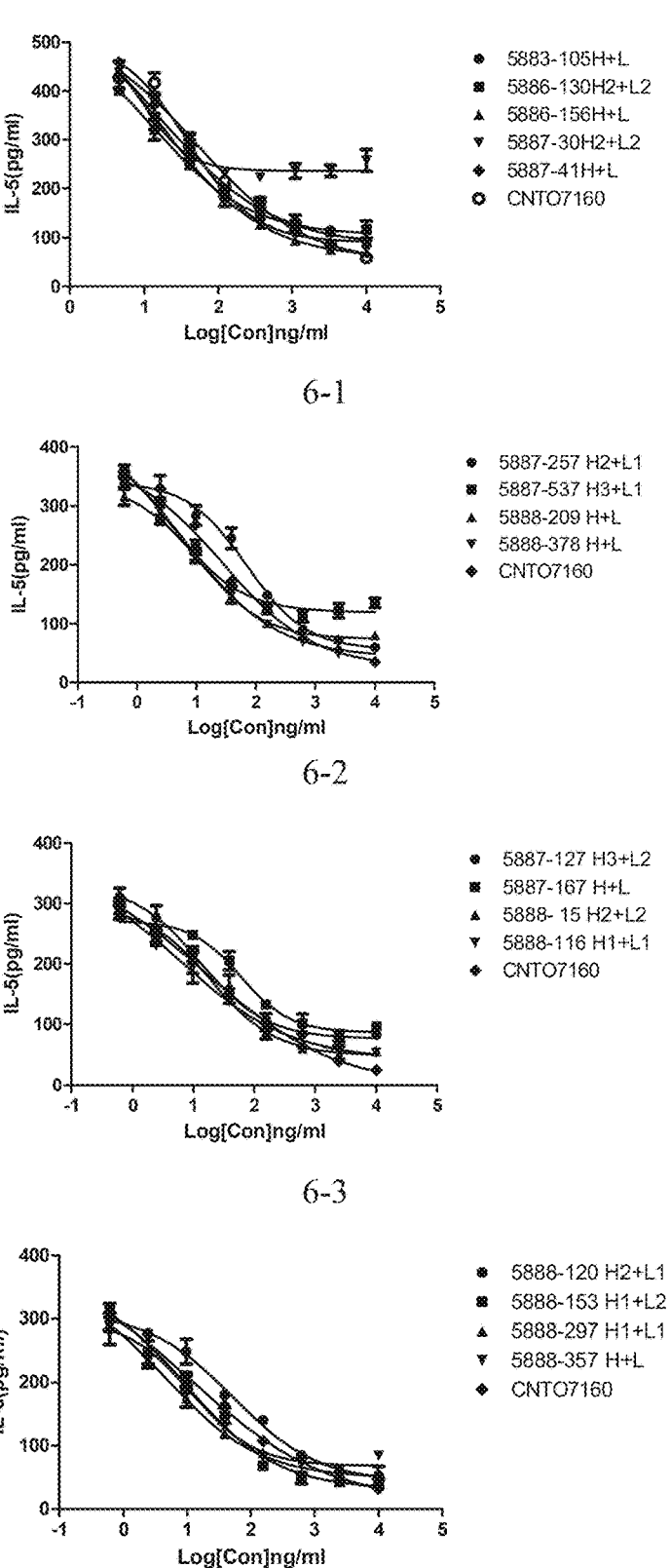
FIG. 6 shows inhibitory activity of murine antibodies on the promotion of KU812-IL5 production by IL-33.
Figure 6:
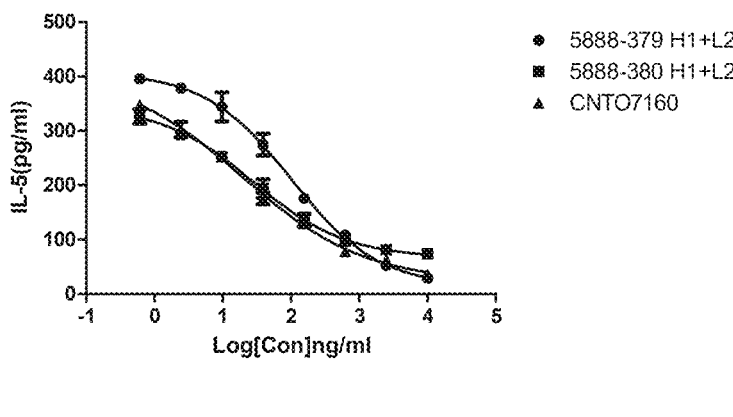

As a 2 μg/mL working solution obtained by 120-fold diluting a stock solution of 240 μg/mL with PB S, the capture antibody contained in Human IL-5 DuoSet ELISA kit was coated at 50 μL/well in ELISA plates at 4° C. overnight, according to the instructions one day in advance. Then the plates were blocked using a blocking buffer for 1 hr, and then washed for 3 times. A 120 ng/mL standard was diluted 400-fold to 300 μg/mL and then diluted 2-fold to obtain serial dilutions of 7 concentrations in total. Culture supernatant of the cells above and one of the diluted standards, 50 μL each, were pipetted into the ELISA plates, and incubated for 2 hrs. The plates were washed for 3 times, and a 125 ng/mL working solution obtained by 60-fold diluting a detection antibody (in a stock solution of 7.5 μg/mL) was added at 50 μL/well into the plates which were then incubated for 2 hrs. The plates were washed for 3 times again, and a 125 ng/mL working solution obtained by 40-fold diluting SA-HRP was added at 50 μL/well into the plates which were then incubated for 20-30 min. Substrate solution was added into the plates at 50 μL/well to develop color in dark for 5-10 min. Afterwards, 2 M sulfuric acid was added at 100 μL/well to stop reaction; and GD values at 450 nm and 650 nm were read by a microplate reader. Results are shown in Table 6 and FIG. 6.

TABLE 6

| Inhibitory activity of murine antibodies on the promotion of KU812-IL-5 production by IL-33 | | |
| --- | --- | --- |
| Antibody | Relative activity (%) | Maximum inhibition rate (%) |
| 5883-105H + L | 342.64 | 80.33 |
| 5886-130H2 + L2 | 344.54 | 71.06 |
| 5886-156H + L | 303.78 | 84.16 |
| 5887-30H2 + L2 | 490.35 | 41.40 |
| 5887-41H + L | 128.40 | 79.25 |
| 5887-257H2 + L1 | 40.03 | 82.17 |
| 5887-537H3 + L1 | 766.96 | 62.25 |
| 5888-209H + L | 254.91 | 74.38 |
| 5888-378H + L | 466.20 | 84.53 |
| 5887-127H3 + L2 | 126.96 | 73.54 |
| 5887-167H + L | 26.14 | 66.68 |
| 5888-15H2 + L2 | 80.56 | 80.22 |
| 5888-116H1 + L1 | 238.00 | 81.40 |
| 5888-120H2 + L1 | 21.72 | 82.02 |
| 5888-153H1 + L2 | 115.09 | 86.00 |
| 5888-297H1 + L1 | 246.30 | 80.38 |
| 5888-357H + L | 98.54 | 71.03 |
| 5888-379H1 + L2 | 19.17 | 92.72 |
| 5888-380H1 + L2 | 69.84 | 77.33 |
| CNTO7160 | | 89.00 |

(7) Experiment on the Cross-Reaction of Murine Antibodies with Mouse ST2 and Cyno ST2

Figure 7:
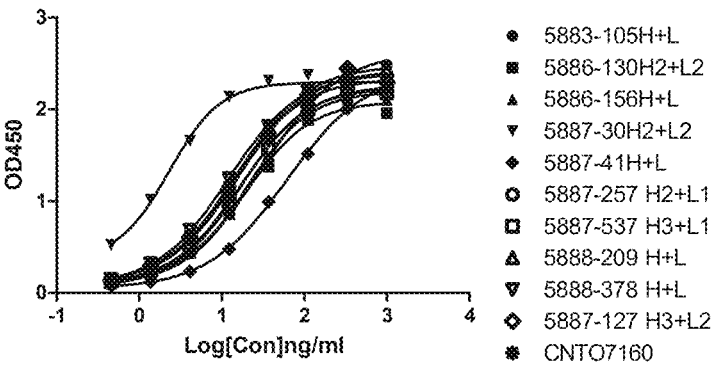
FIG. 7 shows binding of murine antibodies to cyno ST2.
Figure 7:
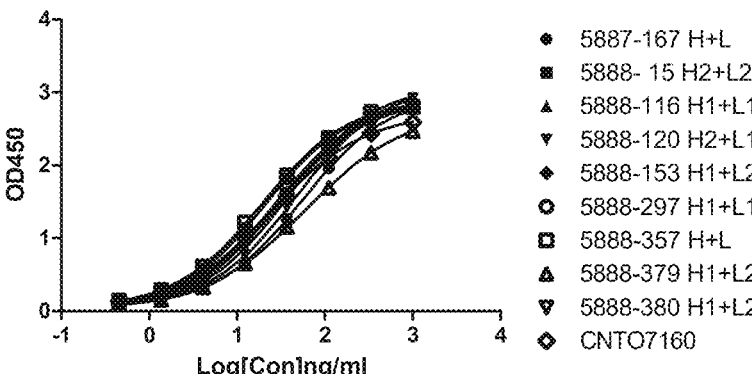

Cyno ST2-fc was diluted with a coating buffer to 1 μg/mL, added into 96-well plates at 50 μL/well and coated overnight at 4° C. Next day, the coated plates were taken, washed with PB ST for 3 times, and then incubated using a blocking buffer at room temperature for 1 hr. Subsequently, the plates were washed with PBST for 3 times again. Starting at 1000 ng/mL, each murine antibody was diluted 3-fold to obtain serial dilutions of 8 concentrations in total which were then added into the 96-well plates at 50 μL/well. The plates were incubated at room temperature for 1 hr, washed with PB ST for 3 times; and then a goat anti-mouse secondary antibody (1:10000) was added at 50 μL/well into the 96-well plates which subsequently were incubated at room temperature for 1 hr. The 96-well plates were washed with PB ST for 3 times, and TMB was added at 50 μL/well to develop color in dark for 10 min. Afterwards, 2 M sulfuric acid was added to stop reaction; and GD values at 450 nm were read by a microplate reader. Results are shown in Table 7 and FIG. 7. It can be seen that the murine antibodies can bind to cyno ST2, with a binding trendency consistent with the binding to human ST2.

TABLE 7

| Experiment results of the binding of murine antibodies to cyno ST2 | | |
| --- | --- | --- |
| Antibody | EC$_{50}$ (ng/mL) | Relative activity (%) |
| 5883-105H + L | 29.45 | 45.67 |
| 5886-130H2 + L2 | 19.30 | 69.69 |
| 5886-156H + L | 20.26 | 66.39 |
| 5887-30H2 + L2 | 2.31 | 582.76 |
| 5887-41H + L | 61.51 | 21.87 |

TABLE 7-continued

Experiment results of the
binding of murine antibodies to cyno ST2

| Antibody | EC$_{50}$ (ng/mL) | Relative activity (%) |
|---|---|---|
| 5887-257H2 + L1 | 17.33 | 77.61 |
| 5887-537H3 + L1 | 17.14 | 78.47 |
| 5888-209H + L | 15.23 | 88.31 |
| 5888-378H + L | 11.91 | 112.93 |
| 5887-127H3 + L2 | 15.78 | 85.23 |
| 5887-167H + L | 54.87 | 44.51 |
| 5888-15H2 + L2 | 20.95 | 116.56 |
| 5888-116H1 + L1 | 38.36 | 63.66 |
| 5888-120H2 + L1 | 47.71 | 51.18 |
| 5888-153H1 + L2 | 30.26 | 80.70 |
| 5888-297H1 + L1 | 28.17 | 86.69 |
| 5888-357H + L | 19.25 | 126.86 |
| 5888-379H1 + L2 | 60.18 | 40.58 |
| 5888-380H1 + L2 | 30.59 | 79.83 |

The experiment on the interactions between the anti-human ST2 antibodies and cyno ST2-fc was performed using Biacore X100, and was carried out at 25° C. in HBS-EP (1×) buffer (pH 7.4). Each antibody was immobilized on the surface of CM5 chip using an amino coupling kit. Following the antibody immobilization, a solution of cyno ST2-fc (2-fold gradient dilution from a starting concentration of 8 nM, to obtain 6 concentrations in total; the starting concentration might be increased if the signal of some sample was too low) was injected. Association was monitored for 2 min and dissociation for 10 min, and the sensor surface was regenerated by injecting a solution of glycine at pH 1.5. Kinetic data were analyzed using a simple 1:1 binding model and results are shown in Table 8.

TABLE 8

Detection results of affinity
of murine antibodies for cyno ST2

| Antibody | ka (1/Ms) | kd (1/s) | KD (M) |
|---|---|---|---|
| CNTO7160 | 1.63E+06 | 2.21E−04 | 1.36E−10 |
| 5886-156H + L | 3.62E+06 | 7.47E−04 | 2.06E−10 |
| 5887-41H + L | 7.98E+06 | 7.21E−04 | 9.03E−11 |
| 5887-537H3 + L1 | 6.33E+06 | 5.11E−04 | 8.07E−11 |
| 5888-116H1 + L1 | 8.14E+06 | 3.82E−04 | 4.69E−11 |
| 5888-153H1 + L2 | 9.68E+06 | 1.39E−03 | 1.43E−10 |
| 5888-357H + L | 6.41E+06 | 8.26E−04 | 1.29E−10 |
| 5888-379H1 + L2 | 4.78E+06 | 1.52E−04 | 3.17E−11 |

Figure 8:
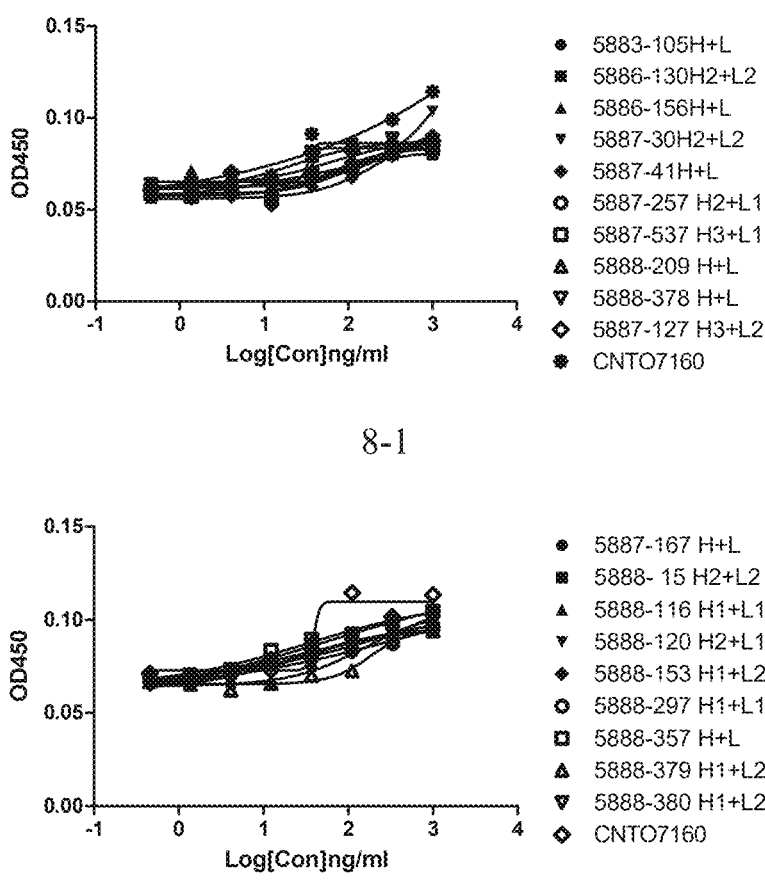
FIG. 8 shows binding of murine antibodies to mouse ST2.

Mouse ST2-fc was diluted with a coating buffer to 1 µg/mL, added into 96-well plates at 50 µL/well and coated overnight at 4° C. Next day, the coated plates were taken, washed with PBST for 3 times, and then incubated using a blocking buffer at room temperature for 1 hr. Subsequently, the plates were washed with PBST for 3 times again. Starting at 1000 ng/mL, each murine antibody was diluted 3-fold to obtain serial dilutions of 8 concentrations in total which were then added into the 96-well plates at 50 µL/well. The plates were incubated at room temperature for 1 hr, washed with PBST for 3 times; and then a goat anti-mouse secondary antibody (1:10000) was added at 50 µL/well into the 96-well plates which subsequently were incubated at room temperature for 1 hr. The 96-well plates were washed with PBST for 3 times, and TMB was added at 50 µL/well to develop color in dark for 10 min. Afterwards, 2 M sulfuric acid was added to stop reaction; and OD values at 450 nm were read by a microplate reader. Results are shown in FIG. 8. It can be seen that the murine antibodies can bind weakly to mouse ST2, similar to control antibody CNTO7160.

2.3 Humanization 7 mouse antibodies 5886-156H+L, 5887-41H+L, 5887-537H3H+L1, 5888-116H1+L1, 5888-153H1+L2, 5888-357H+L, 5888-379H1+L2 were selected for humanization design.

Heavy and light chain variable region sequences of the 7 murine antibodies were compared to human germline sequences by blast searches in IMGT database. Redundant genes as well as those with unpaired cysteines were removed from the human germline genes. The human germline gene in the remaining ones having the most matched framework and CDR regions was selected and framework regions therein were used as human acceptor frameworks. FR-4 was selected based on sequence similarity of IGHJ/IGJK germline genes. Tables 9 to 15 show the humanized sequences of the 7 murine antibodies 5886-156H+L, 5887-41H+L, 5887-537H3H+L1, 5888-116H1+L1, 5888-153H1+L2, 5888-357H+L, 5888-379H1+L2, respectively, in which the HZ0 versions represent only CDR-grafted ones, the HZ1 versions have back mutation(s) introduced, and the HZ2 and further versions have mutation(s) which are attempted at PTM sites present in the sequences. Specific sequences after humanization are shown in Tables 9 to 15, with corresponding CDRs (defined by enhanced Chothia/AbM) underlined.

TABLE 9

Humanized sequences of heavy and
light variable regions numbered 5886-156

| VH | Sequence | VL | Sequence |
|---|---|---|---|
| 5886-156H-VH (SEQ ID NO. 1) | DVQLQQSGPGLVKPSQSLSL TCTVTGYSITSDYAWNWIR QFPGNKLEWMGYIDYSGST TYNPSLKSRFSITRDTSKNQ FFLQLNSVTTEDTATYYCAS TVIDSMDYWGQGTSVTVSS | 5886-156L-VL (SEQ ID NO. 29) | DIVLTQSPASLAVSLGQRAT ISCRASKSVSTSGHSYMH WYQQKPGQPPKLLIYLAS NLESGVPARFSGSGSGTDF TLNINPMEEEDAATYYCQ HSREFPFTFGSGTKLEIK |
| IGHV4-30-4*01| IGHJ4*01 | QVQLQESGPGLVKPSQTLSL TCTVSGGSISSGDYYWSWI RQPPGKGLEWIGYIYYSGST YYNPSLKSRVTISVDTSKNQ FSLKLSSVTAADTAVYYCA RYFDYWGQGTLVTVSS | IGKV7-3*01| IGKJ1*01 | DIVLTQSPASLAVSPGQRAT ITCRASESVSFLGINLIHWY QQKPGQPPKLLIYQASNK DTGVPARFSGSGSGTDFTL TINPVEANDTANYYCLQS KNFPWTFGQGTKVEIK |

TABLE 9-continued

Humanized sequences of heavy and
light variable regions numbered 5886-156

| VH | Sequence | VL | Sequence |
|---|---|---|---|
| 5886-156H-VH-HZ0 (SEQ ID NO. 2) | QVQLQESGPGLVKPSQTLSL TCTVSGYSITSDYAWNWIR QPPGKGLEWIGYIDYSGSTT YNPSLKSRVTISVDTSKNQF SLKLSSVTAADTAVYYCAR TVIDSMDYWGQGTLVTVSS | 5886-156L-VL-HZ0 (SEQ ID NO. 30) | DIVLTQSPASLAVSPGQRAT ITCRASKSVSTSGHSYMH WYQQKPGQPPKLLIYLAS NLESGVPARFSGSGSGTDF TLTINPVEANDTANYYCQH SREFPFTFGQGTKVEIK |
| 5886-156H-VH-HZ1 (SEQ ID NO. 3) | QVQLQESGPGLVKPSQTLSL TCTVSGYSITSDYAWNWIR QPPGKGLEWIGYIDYSGSTT YNPSLKSRVTISRDTSKNQF SLKLSSVTAADTAVYYCAS TVIDSMDYWGQGTLVTVSS | 5886-156L-VL-HZ1 (SEQ ID NO. 31) | DIVLTQSPASLAVSPGQRAT ITCRASKSVSTSGHSYMH WYQQKPGQPPKLLIYLAS NLESGVPARFSGSGSGTDF TLTINPVEANDAANYYCQ HSREFPFTFGQGTKVEIK |

TABLE 10

Humanized sequences of heavy and light variable regions numbered 5887-41

| VH | Sequence | VL | Sequence |
|---|---|---|---|
| 5887-41H-VH (SEQ ID NO. 4) | DVQLQQSGPGLVKPSQSLSL TCTVTGYSITSDYAWDWIR QFPGNKLEWMGYIRYSGDT YYNPSLKSRISITRDTSKNQF FLQLNSVTTEDTATYYCATT MMDTMDYWGQGTSVTVSS | 5887-41L-VL (SEQ ID NO. 32) | DIVLTQSPASLTVSLGQRA TISCRASKSVSTSGNSYMH WYQQKPGQPPKLLIYLAS NLESGVPARFSGSGSGTDF TLNIHPVEEDAATYYCQH SREFPLTFGAGTKLELK |
| IGHV4-30-4*01\|IGHJ4*01 | QVQLQESGPGLVKPSQTLSL TCTVSGGSISSGDYYWSWIR QPPGKGLEWIGYIYYSGSTY YNPSLKSRVTISVDTSKNQF SLKLSSVTAADTAVYYCAR YFDYWGQGTLVTVSS | IGKV7-3*01\|IGKJ2*01 | DIVLTQSPASLAVSPGQRAT ITCRASESVSFLGINLIHWY QQKPGQPPKLLIYQASNK DTGVPARFSGSGSGTDFTL TINPVEANDTANYYCLQS KNFPYTFGQGTKLEIK |
| 5887-41H-VH-HZ0 (SEQ ID NO. 5) | QVQLQESGPGLVKPSQTLSL TCTVSGYSITSDYAWDWIR QPPGKGLEWIGYIRYSGDTY YNPSLKSRVTISVDTSKNQF SLKLSSVTAADTAVYYCART MMDTMDYWGQGTLVTVSS | 5887-41L-VL-HZ0 (SEQ ID NO. 33) | DIVLTQSPASLAVSPGQRA TITCRASKSVSTSGNSYMH WYQQKPGQPPKLLIYLAS NLESGVPARFSGSGSGTDF TLTINPVEANDTANYYCQH SREFPLTFGQGTKLEIK |
| 5887-41H-VH-HZ1 (SEQ ID NO. 6) | QVQLQESGPGLVKPSQTLSL TCTVSGYSITSDYAWDWIR QPPGKGLEWIGYIRYSGDTY YNPSLKSRVTISRDTSKNQF SLKLSSVTAADTAVYYCATT MMDTMDYWGQGTLVTVSS | 5887-41L-VL-HZ1 (SEQ ID NO. 34) | DIVLTQSPASLAVSPGQRA TITCRASKSVSTSGNSYMH WYQQKPGQPPKLLIYLAS NLESGVPARFSGSGSGTDF TLTINPVEANDAANYYCQ HSREFPLTFGQGTKLEIK |
| | | 5887-41L-VL-HZ2 (SEQ ID NO. 35) | DIVLTQSPASLAVSPGQRA TITCRASKSVSTSGNTYMH WYQQKPGQPPKLLIYLAS NLESGVPARFSGSGSGTDF TLTINPVEANDAANYYCQ HSREFPLTFGQGTKLEIK |

TABLE 11

Humanized sequences of heavy and light variable regions numbered 5887-537

| VH | Sequence | VL | Sequence |
|---|---|---|---|
| 5887-537H3-VH (SEQ ID NO. 7) | QVTLKESGPGILQPSQTLSLT CSFSGFSLSTSGMGVGWIRQ PSGKGLEWLAHIWWDDVK QYNPALKSRLTISKDTSSSQ VFLKSASVDTADTATYYCA | 5887-537L1-VL (SEQ ID NO. 36) | DIVLTQSPASLAVSLGQRAT ISCRASESVEYSGTSLMQW YQQKPGQPPKLLIYVASNV ESGVPARFSGSGSGTDFSL NIHPVEEDDIAMYFCQQSR |

TABLE 11-continued

Humanized sequences of heavy and light variable regions numbered 5887-537

| VH | Sequence | VL | Sequence |
|---|---|---|---|
| | RIGGDYDYFDFWGQGTTLT VSS | | KVPWTFGGGTKLEIK |
| IGHV2-5*09\| IGHD3-16*01\| IGHJ6*02 | QVTLKESGPTLVKPTQTLTL TCTFSGFSLSTSGVGVGWIR QPPGKALEWLALIYWDDD KRYGPSLKSRLTITKDTSKN QVVLTMTNMDPVDTATYY CAHRYYYYYGMDVWGQG TTVTVSS | IGKV7-3*01\| IGKJ2*01 | DIVLTQSPASLAVSPGQRAT ITCRASESVSFLGINLIHWY QQKPGQPPKLLIYQASNK DTGVPARFSGSGSGTDFTL TINPVEANDTANYYCLQS KNFPYTFGQGTKLEIK |
| 5887-537H3-VH-HZ0 (SEQ ID NO. 8) | QVTLKESGPTLVKPTQTLTL TCTFSGFSLSTSGMGVGWIR QPPGKALEWLAHIWWDDV KQYNPALKSRLTITKDTSKN QVVLTMTNMDPVDTATYY CAHIGGDYDYFDFWGQGTT VTVSS | 5887-537L1-VL-HZ0 (SEQ ID NO. 37) | DIVLTQSPASLAVSPGQRAT ITCRASESVEYSGTSLMQW YQQKPGQPPKLLIYVASNV ESGVPARFSGSGSGTDFTL TINPVEANDTANYYCQQS RKVPWTFGQGTKLEIK |
| 5887-537H3-VH-HZ1 (SEQ ID NO. 9) | QVTLKESGPTLVKPTQTLTL TCTFSGFSLSTSGMGVGWIR QPPGKALEWLAHIWWDDV KQYNPALKSRLTITKDTSKS QVVLTMTNMDPVDTATYY CARIGGDYDYFDFWGQGTT VTVSS | 5887-537L1-VL-HZ1 (SEQ ID NO. 38) | DIVLTQSPASLAVSPGQRAT ITCRASESVEYSGTSLMQW YQQKPGQPPKLLIYVASNV ESGVPARFSGSGSGTDFTL TINPVEANDIANYFCQQSR KVPWTFGQGTKLEIK |

TABLE 12

Humanized sequences of heavy and light variable regions numbered 5888-116

| VH | Sequence | VL | Sequence |
|---|---|---|---|
| 5888-116H1-VH (SEQ ID NO. 10) | QVQLQQSGAELVRPGASVT LSCKASGYTFTDSEMYWV RLTPVHGLEWIGAIDPETG DTAFNQKFKGKATLTADKS SSTAYMELRSLTSEDSVVY YCTRAFDNDNDDGFAYWG QGTLVTVSA | 5888-116L1-VL (SEQ ID NO. 39) | QIVMTQSPAIMSASPGEKV TMTCSASSSVNYMHWYQ QKSGTSPKRWIYDTSKLAS GVPARFSGSGSGTSYSLTIS SMEAEDAATYYCQQWSSN PLTFGAGTKLELK |
| IGHV1-46*01\| IGHJ3*01 | QVQLVQSGAEVKKPGASV KVSCKASGYTFTSYYMHW VRQAPGQGLEWMGIINPSG GSTSYAQKFQGRVTMTRDT STSTVYMELSSLRSEDTAV YYCARDAFDVWGQGTMV TVSS | IGKV1-33*01\| IGKJ2*01 | DIQMTQSPSSLSASVGDRV TITCQASQDISNYLNWYQ QKPGKAPKLLIYDASNLET GVPSRFSGSGSGTDFTFTIS SLQPEDIATYYCQQYDNLP YTFGQGTKLEIK |
| 5888-116H1-VH-HZ0 (SEQ ID NO. 11) | QVQLVQSGAEVKKPGASV KVSCKASGYTFTDSEMYW VRQAPGQGLEWMGAIDPE TGDTAFNQKFKGRVTMTR DTSTSTVYMELSSLRSEDTA VYYCARAFDNDNDDGFAY WGQGTMVTVSS | 5888-116L1-VL-HZ0 (SEQ ID NO. 40) | DIQMTQSPSSLSASVGDRV TITCSASSSVNYMHWYQQ KPGKAPKLLIYDTSKLASG VPSRFSGSGSGTDFTFTISS LQPEDIATYYCQQWSSNPL TFGQGTKLEIK |
| 5888-116H1-VH-HZ1 (SEQ ID NO. 12) | QVQLVQSGAEVKKPGASV KVSCKASGYTFTDSEMYW VRQAPGQGLEWMGAIDPE TGDTAFNQKFKGRVTMTA DKSTSTAYMELSSLRSEDTA VYYCTRAFDNDNDDGFAY WGQGTMVTVSS | 5888-116L1-VL-HZ1 (SEQ ID NO. 41) | DIQMTQSPSSLSASVGDRV TITCSASSSVNYMHWYQQ KPGKAPKRLIYDTSKLASG VPSRFSGSGSGTDYTFTISS LQPEDAATYYCQQWSSNP LTFGQGTKLEIK |
| 5888-116H1-VH-HZ2 (SEQ ID NO. 13) | QVQLVQSGAEVKKPGASV KVSCKASGYTFTDSEMYW VRQAPGQGLEWMGAIDPE TGDTAFNQKFKGRVTMTA DKSTSTAYMELSSLRSEDTA VYYCTRAFDNDNDEGFAY WGQGTMVTVSS | | |

TABLE 12-continued

| Humanized sequences of heavy and light variable regions numbered 5888-116 | | | |
| --- | --- | --- | --- |
| VH | Sequence | VL | Sequence |
| 5888-116H1-<br>VH-HZ3<br>(SEQ ID<br>NO. 14) | QVQLVQSGAEVKKPGASV<br>KVSCKASGYTFTDSEMYW<br>VRQAPGQGLEWMGAIDPE<br>TGDTAFNQKFKGRVTMTA<br>DKSTSTAYMELSSLRSEDTA<br>VYYCTRAFDNDNDDAFAY<br>WGQGTMVTVSS | | |

TABLE 13

| Humanized sequences of heavy and light variable regions numbered 5888-153 | | | |
| --- | --- | --- | --- |
| VH | Sequence | VL | Sequence |
| 5888-153H1-<br>VH<br>(SEQ ID<br>NO. 15) | QVQLQQSGAELVRPGASVT<br>LSCKASGYTFTDYELHWV<br>KQTPVHGLEWIGTIDPETG<br>DTVYNQKFKAKAILTADKS<br>SSTAYMEFRSLTSEDSAVCY<br>CTRAFYNDYDDGFAYWGQ<br>GTLVTVSA | 5888-<br>153L2-VL<br>(SEQ ID<br>NO. 42) | QIVMTQTPAIMSASPGEKV<br>TMTCSVSSSVSYMHWYQ<br>QKSGTSPKRWIYDTSKLAS<br>GVPARFSGSGSGTSYSLTIN<br>NMEAEDAATYYCQQWNS<br>SPLTFGAGTKLELK |
| IGHV1-<br>46*01\|<br>IGHJI*01 | QVQLVQSGAEVKKPGASV<br>KVSCKASGYTFTSYYMHW<br>VRQAPGQGLEWMGIINPSG<br>GSTSYAQKFQGRVTMTRDT<br>STSTVYMELSSLRSEDTAV<br>YYCARAEYFQHWGQGTLV<br>TVSS | IGKV3-<br>11*01\|<br>IGKJ4*02 | EIVLTQSPATLSLSPGERAT<br>LSCRASQSVSSYLAWYQQ<br>KPGQAPRLLIYDASNRATG<br>IPARFSGSGSGTDFTLTISSL<br>EPEDFAVYYCQQRSNWPL<br>TFGGGTKVEIK |
| 5888-153H1-<br>VH-HZ0<br>(SEQ ID<br>NO. 16) | QVQLVQSGAEVKKPGASV<br>KVSCKASGYTFTDYELHW<br>VRQAPGQGLEWMGTIDPE<br>TGDTVYNQKFKARVTMTR<br>DTSTSTVYMELSSLRSEDTA<br>VYYCARAFYNDYDDGFAY<br>WGQGTLVTVSS | 5888-<br>153L2-VL-<br>HZ0<br>(SEQ ID<br>NO. 43) | EIVLTQSPATLSLSPGERAT<br>LSCSVSSSVSYMHWYQQK<br>PGQAPRLLIYDTSKLASGIP<br>ARFSGSGSGTDFTLTISSLE<br>PEDFAVYYCQQWNSSPLTF<br>GGGTKVEIK |
| 5888-153H1-<br>VH-HZ1<br>(SEQ ID<br>NO. 17) | QVQLVQSGAEVKKPGASV<br>KVSCKASGYTFTDYELHW<br>VRQAPGQGLEWMGTIDPE<br>TGDTVYNQKFKARVTMTA<br>DKSTSTAYMELSSLRSEDTA<br>VYYCTRAFYNDYDDGFAY<br>WGQGTLVTVSS | 5888-<br>153L2-VL-<br>HZ1<br>(SEQ ID<br>NO. 44) | EIVMTQSPATLSLSPGERAT<br>LSCSVSSSVSYMHWYQQK<br>PGQAPRLLIYDTSKLASGIP<br>ARFSGSGSGTDYTLTISSLE<br>PEDAAVYYCQQWNSSPLT<br>FGGGTKVEIK |
| 5888-153H1-<br>VH-HZ2<br>(SEQ ID<br>NO. 18) | QVQLVQSGAEVKKPGASV<br>KVSCKASGYTFTDYELHW<br>VRQAPGQGLEWMGTIDPE<br>TGDTVYNQKFKARVTMTA<br>DKSTSTAYMELSSLRSEDTA<br>VYYCTRAFYNDYDEGFAY<br>WGQGTLVTVSS | 5888-<br>153L2-VL-<br>HZ2<br>(SEQ ID<br>NO. 45) | EIVMTQSPATLSLSPGERAT<br>LSCSVSSSVSYMHWYQQK<br>PGQAPRRLIYDTSKLASGIP<br>ARFSGSGSGTDYTLTISSLE<br>PEDAAVYYCQQWNTSPLT<br>FGGGTKVEIK |
| 5888-153H1-<br>VH-HZ3<br>(SEQ ID<br>NO. 19) | QVQLVQSGAEVKKPGASV<br>KVSCKASGYTFTDYELHW<br>VRQAPGQGLEWMGTIDPE<br>TGDTVYNQKFKARVTMTA<br>DKSTSTAYMELSSLRSEDTA<br>VYYCTRAFYNDYDDAFAY<br>WGQGTLVTVSS | | |

TABLE 14

| Humanized sequences of heavy and light variable regions numbered 5888-357 | | | |
|---|---|---|---|
| VH | Sequence | VL | Sequence |
| 5888-357H-VH (SEQ ID NO. 20) | QVQLQQSVTELVRPGASVTL SCKASGYRFTDSEMHWVKQ TPVHGLEWIGTIDPETGGTV YNQKFKGKAKLTADRSSSTV SMELRSLTSEDSAVYYCTRA FYNDFDDGFAYWGQGTLVT VSA | 5888-357L-VL (SEQ ID NO. 46) | QIVMTQSPAIMSASPGEKV TLTCSASTSVSYMHWYQQ KSGTSPKRWIYDTSKLASG VPARFSGSGSGTSYSLTISS MEAEDAATYYCQQWSSNP LTFGAGTKLELK |
| IGHV1-46*01\|IGHJ3*01 | QVQLVQSGAEVKKPGASVK VSCKASGYTFTSYYMHWVR QAPGQGLEWMGIINPSGGST SYAQKFQGRVTMTRDTSTST VYMELSSLRSEDTAVYYCAR DAFDVWGQGTMVTVSS | IGKV3-11*01\|IG KJ4*02 | EIVLTQSPATLSLSPGERAT LSCRASQSVSSYLAWYQQ KPGQAPRLLIYDASNRATG IPARFSGSGSGTDFTLTISSL EPEDFAVYYCQQRSNWPL TFGGGTKVEIK |
| 5888-357H-VH-HZ0 (SEQ ID NO. 21) | QVQLVQSGAEVKKPGASVK VSCKASGYRFTDSEMHWVR QAPGQGLEWMGTIDPETGG TVYNQKFKGRVTMTRDTST STVYMELSSLRSEDTAVYC ARAFYNDFDDGFAYWGQGT MVTVSS | 5888-357L-VL-HZ0 (SEQ ID NO. 47) | EIVLTQSPATLSLSPGERAT LSCSASTSVSYMHWYQQK PGQAPRLLIYDTSKLASGIP ARFSGSGSGTDFTLTISSLE PEDFAVYYCQQWSSNPLTF GGGTKVEIK |
| 5888-357H-VH-HZ1 (SEQ ID NO. 22) | QVQLVQSGAEVKKPGASVK VSCKASGYRFTDSEMHWVR QAPGQGLEWMGTIDPETGG TVYNQKFKGRVTMTADRST STVYMELSSLRSEDTAVYC TRAFYNDFDDGFAYWGQGT MVTVSS | 5888-357L-VL-HZ1 (SEQ ID NO. 48) | EIVMTQSPATLSLSPGERAT LSCSASTSVSYMHWYQQK PGQAPRRLIYDTSKLASGIP ARFSGSGSGTDYTLTISSLE PEDAAVYYCQQWSSNPLT FGGGTKVEIK |
| 5888-357H-VH-HZ2 (SEQ ID NO. 23) | QVQLVQSGAEVKKPGASVK VSCKASGYRFTDSEMHWVR QAPGQGLEWMGTIDPETGG TVYNQKFKGRVTMTADRST STVYMELSSLRSEDTAVYC TRAFYNDFDEGFAYWGQGT MVTVSS | | |
| 5888-357H-VH-HZ3 (SEQ ID NO. 24) | QVQLVQSGAEVKKPGASVK VSCKASGYRFTDSEMHWVR QAPGQGLEWMGTIDPETGG TVYNQKFKGRVTMTADRST STVYMELSSLRSEDTAVYC TRAFYNDFDDAFAYWGQGT MVTVSS | | |

TABLE 15

| Humanized sequences of heavy and light variable regions numbered 5888-379 | | | |
|---|---|---|---|
| VH | Sequence | VL | Sequence |
| 5888-379H1-VH (SEQ ID NO. 25) | QIQLAQSGPELKKPGETVKI SCKASGYTFINYGMNWVK QAPGKDLKWMGWINTYIG EPTYGDNFKGRFAFSLETSA STVYLQINNLKNEDTATYF CAREGDGFAYWGQGTLVT VSA | 5888-379L2-VL (SEQ ID NO. 49) | DIVMTQSPPSLSVSVGEKV TMSCKSSQSLLYSGNQNN YLAWYQQKPGQPPKLLIY GASTRESGVPDRFTGSGSG TDFTLTISSVQAEDLAVYY CQNDHSYPYTFGGGTKLEI K |
| IGHV1-3*01\| IGHJ4*01 | QVQLVQSGAEVKKPGASV KVSCKASGYTFTSYAMHW VRQAPGQRLEWMGWINAG NGNTKYSQKFQGRVTITRD TSASTAYMELSSLRSEDTAV YYCARYFDYWGQGTLVTV SS | IGKV4-1*01\| IGKJ2*01 | DIVMTQSPDSLAVSLGERA TINCKSSQSVLYSSNNKNY LAWYQQKPGQPPKLLIYW ASTRESGVPDRFSGSGSGT DFTLTISSLQAEDVAVYYC QQYYSTPYTFGQGTKLEIK |
| 5888-379H1-HZ0 (SEQ ID NO. 26) | QVQLVQSGAEVKKPGASV KVSCKASGYTFINYGMNW VRQAPGQRLEWMGWINTY IGEPTYGDNFKGRVTITRDT | 5888-379L2-VK4-HZ0 (SEQ ID | DIVMTQSPDSLAVSLGERA TINCKSSQSLLYSGNQNNY LAWYQQKPGQPPKLLIYG ASTRESGVPDRFSGSGSGT |

TABLE 15-continued

| Humanized sequences of heavy and light variable regions numbered 5888-379 | | | |
|---|---|---|---|
| VH | Sequence | VL | Sequence |
| | SASTAYMELSSLRSEDTAVY YCAREGDGFAYWGQGTLV TVSS | NO. 50) | DFTLTISSLQAEDVAVYYC QNDHSYPYTFGGGTKVEI K |
| 5888-379H1-VH-HZ1 (SEQ ID NO. 27) | QVQLVQSGAEVKKPGASV KVSCKASGYTFINYGMNW VRQAPGQRLEWMGWINTY IGEPTYGDNFKGRVTITRDT SASTAYMELSSLRSEDTAVY YCAREGEGFAYWGQGTLV TVSS | 5888-379L2-VK4-HZ1 (SEQ ID NO. 51) | DIVMTQSPDSLAVSLGERA TINCKSSQSLLYSGNQNNY LAWYQQKPGQPPKLLIYG ASTRESGVPDRFSGSGSGT DFTLTISSLQAEDLAVYYC QNDHSYPYTFGGGTKVEI K |
| 5888-379H1-VH-HZ2 (SEQ ID NO. 28) | QVQLVQSGAEVKKPGASV KVSCKASGYTFINYGMNW VRQAPGQRLEWMGWINTY IGEPTYGDNFKGRVTITRDT SASTAYMELSSLRSEDTAVY YCAREGDAFAYWGQGTLV TVSS | IGKV1-27*01\| IGKJ2*01 | DIQMTQSPSSLSASVGDRV TITCRASQGISNYLAWYQQ KPGKVPKLLIYAASTLQSG VPSRFSGSGSGTDFTLTISS LQPEDVATYYCQKYNSAP YTFGQGTKLEIK |
| | | 5888-379L2-VK1-HZ0 (SEQ ID NO. 52) | DIQMTQSPSSLSASVGDRV TITCKSSQSLLYSGNQNNY LAWYQQKPGKVPKLLIYG ASTRESGVPSRFSGSGSGT DFTLTISSLQPEDVATYYCQ NDHSYPYTFGGGTKVEIK |
| | | 5888-379L2-VK1-HZ1 (SEQ ID NO. 53) | DIQMTQSPSSLSASVGDRV TITCKSSQSLLYSGNQNNY LAWYQQKPGKVPKLLIYG ASTRESGVPSRFSGSGSGT DFTLTISSLQPEDLATYYCQ NDHSYPYTFGGGTKVEIK |

2.4 Recombinant Expression and Screening of Humanized Antibodies

(1) Recombinant Expression of Humanized Antibodies

Humanized light and heavy chains derived from the same murine antibody were constructed using a heavy chain constant region as shown in SEQ ID NO. 54 and a light chain constant region as shown in SEQ ID NO. 55, and co-transfected in pairs into CHO-K1 cells. 24 h after the transfection, 10 µg/mL MSX was added for pressure screening. The cells, after cell density and viability recovered, were inoculated for Feed-batch expression, and supernatants when the expression was completed were centrifuged and purified by protein A. Antibodies obtained were used for quantitative screening after antibody concentrations were determined by BCA method.

Humanized antibodies and light and heavy chain variable regions in pairs contained by the antibodies are shown in Tables 16 to 22. An antibody having a name suffixed with "ix" is a chimeric antibody accordingly.

TABLE 16

| Light and heavy chain variable regions in pairs of humanized antibodies numbered 5886-156 | | | |
|---|---|---|---|
| | 5886-156L-VL (SEQ ID NO. 29) | 5886-156L-VL-HZ0 (SEQ ID NO. 30) | 5886-156L-VL-HZ1 (SEQ ID NO. 31) |
| 5886-156H-VH (SEQ ID NO. 1) | 5886-156-ix | | |
| 5886-156H-VH-HZ0 (SEQ ID NO. 2) | | 5886-156-H0L0 | 5886-156-H0L1 |

TABLE 16-continued

| Light and heavy chain variable regions in pairs of humanized antibodies numbered 5886-156 | | | |
|---|---|---|---|
| | 5886-156L-VL (SEQ ID NO. 29) | 5886-156L-VL-HZ0 (SEQ ID NO. 30) | 5886-156L-VL-HZ1 (SEQ ID NO. 31) |
| 5886-156H-VH-HZ1 (SEQ ID NO. 3) | | 5886-156-H1L0 | 5886-156-H1L1 |

TABLE 17

| Light and heavy chain variable regions in pairs of humanized antibodies numbered 5887-41 | | | | |
|---|---|---|---|---|
| | 5887-41L-VL (SEQ ID NO. 32) | 5887-41L-VL-HZ0 (SEQ ID NO. 33) | 5887-41L-VL-HZ1 (SEQ ID NO. 34) | 5887-41L-VL-HZ2 (SEQ ID NO. 35) |
| 5887-41H-VH (SEQ ID NO. 4) | 5887-41-ix | | | |
| 5887-41H-VH-HZ0 (SEQ ID NO. 5) | | 5887-41-H0L0 | 5887-41-H0L1 | 5887-41-H0L2 |
| 5887-41H-VH-HZ1 (SEQ ID NO. 6) | | 5887-41-H1L0 | 5887-41-H1L1 | 5887-41-H1L2 |

TABLE 18

Light and heavy chain variable regions
in pairs of humanized antibodies numbered 5887-537

| | 5887-537L1-VL (SEQ ID NO. 36) | 5887-537L1-VL-HZ0 (SEQ ID NO. 37) | 5887-537L1-VL-HZ1 (SEQ ID NO. 38) |
|---|---|---|---|
| 5887-537H3-VH (SEQ ID NO. 7) | 5887-537-ix | | |
| 5887-537H3-VH-HZ0 (SEQ ID NO. 8) | | 5887-537-H0L0 | 5887-537-H0L1 |
| 5887-537H3-VH-HZ1 (SEQ ID NO. 9) | | 5887-537-H1L0 | 5887-537-H1L1 |

TABLE 19

Light and heavy chain variable regions
in pairs of humanized antibodies numbered 5888-116

| | 5888-116L1-VL (SEQ ID NO. 39) | 5888-116L1-VL-HZ0 (SEQ ID NO. 40) | 5888-116L1-VL-HZ1 (SEQ ID NO. 41) |
|---|---|---|---|
| 5888-116H1-VH (SEQ ID NO. 10) | 5888-116-ix | | |
| 5888-116H1-VH-HZ0 (SEQ ID NO. 11) | | 5888-116-H0L0 | 5888-116-H0L1 |
| 5888-116H1-VH-HZ1 (SEQ ID NO. 12) | | 5888-116-H1L0 | 5888-116-H1L1 |
| 5888-116H1-VH-HZ2 (SEQ ID NO. 13) | | 5888-116-H2L0 | 5888-116-H2L1 |
| 5888-116H1-VH-HZ3 (SEQ ID NO. 14) | | 5888-116-H3L0 | 5888-116-H3L1 |

TABLE 20

Light and heavy chain variable regions
in pairs of humanized antibodies numbered 5888-153

| | 5888-153L2-VL (SEQ ID NO. 42) | 5888-153L2-VL-HZ0 (SEQ ID NO. 43) | 5888-153L2-VL-HZ1 (SEQ ID NO. 44) | 5888-153L2-VL-HZ2 (SEQ ID NO. 45) |
|---|---|---|---|---|
| 5888-153H1-VH (SEQ ID NO. 15) | 5888-153-ix | | | |
| 5888-153H1-VH-HZ0 (SEQ ID NO. 16) | | 5888-153-H0L0 | 5888-153-H0L1 | 5888-153-H0L2 |
| 5888-153H1-VH-HZ1 (SEQ ID NO. 17) | | 5888-153-H1L0 | 5888-153-H1L1 | 5888-153-H1L2 |
| 5888-153H1-VH-HZ2 (SEQ ID NO. 18) | | 5888-153-H2L0 | 5888-153-H2L1 | 5888-153-H2L2 |
| 5888-153H1-VH-HZ3 (SEQ ID NO. 19) | | 5888-153-H3L0 | 5888-153-H3L1 | 5888-153-H3L2 |

TABLE 21

Light and heavy chain variable regions
in pairs of humanized antibodies numbered 5888-357

| | 5888-357L-VL (SEQ ID NO. 46) | 5888-357L-VL-HZ0 (SEQ ID NO. 47) | 5888-357L-VL-HZ1 (SEQ ID NO. 48) |
|---|---|---|---|
| 5888-357H-VH (SEQ ID NO. 20) | 5888-357-ix | | |

TABLE 21-continued

Light and heavy chain variable regions
in pairs of humanized antibodies numbered 5888-357

| | 5888-357L-VL (SEQ ID NO. 46) | 5888-357L-VL-HZ0 (SEQ ID NO. 47) | 5888-357L-VL-HZ1 (SEQ ID NO. 48) |
|---|---|---|---|
| 5888-357H-VH-HZ0 (SEQ ID NO. 21) | | 5888-357-H0L0 | 5888-357-H0L1 |
| 5888-357H-VH-HZ1 (SEQ ID NO. 22) | | 5888-357-H1L0 | 5888-357-H1L1 |
| 5888-357H-VH-HZ2 (SEQ ID NO. 23) | | 5888-357-H2L0 | 5888-357-H2L1 |
| 5888-357H-VH-HZ3 (SEQ ID NO. 24) | | 5888-357-H3L0 | 5888-357-H3L1 |

TABLE 22

Light and heavy chain variable regions in pairs of humanized
antibodies numbered 5888-379

| | 5888-379L2-VL (SEQ ID NO. 49) | 5888-379L2-VK1-HZ0 (SEQ ID NO. 52) | 5888-379L2-VK1-HZ1 (SEQ ID NO. 53) | 5888-379L2-VK4-HZ0 (SEQ ID NO. 50) | 5888-379L2-VK4-HZ1 (SEQ ID NO. 51) |
|---|---|---|---|---|---|
| 5888-379H1-VH (SEQ ID NO. 25) | 5888-379-ix | | | | |
| 5888-379H1-VH-HZ0 (SEQ ID NO. 26) | | 5888-379-H0L0 | 5888-379-H0L1 | 5888-379-H0L2 | 5888-379-H0L3 |
| 5888-379H1-VH-HZ1 (SEQ ID NO. 27) | | 5888-379-H1L0 | 5888-379-H1L1 | 5888-379-H1L2 | 5888-379-H1L3 |
| 5888-379H1-VH-HZ2 (SEQ ID NO. 28) | | 5888-379-H2L0 | 5888-379-H2L1 | 5888-379-H2L2 | 5888-379-H2L3 |

Figure 9:
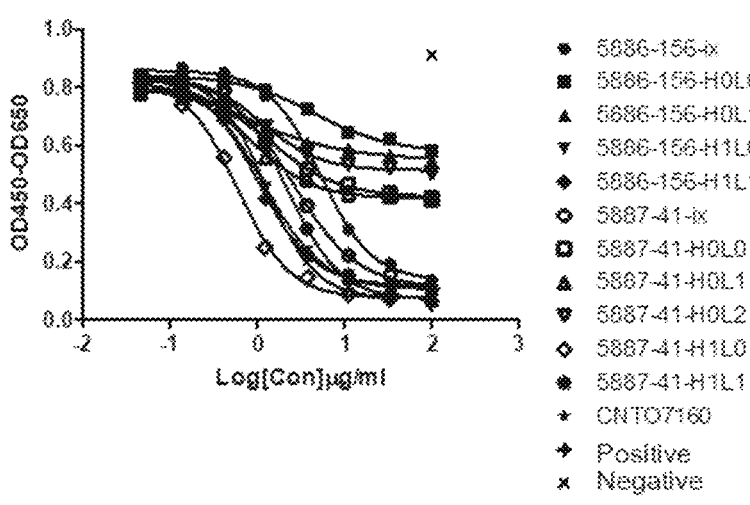
FIG. 9 shows blocking assay screening of humanized antibodies on the binding of IL33 to human ST2.
Figure 9:
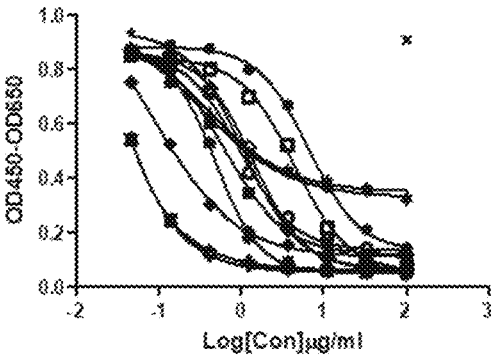
Figure 9:
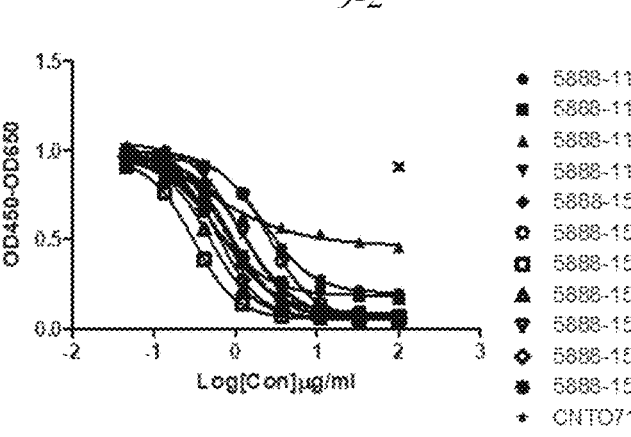
Figure 9:
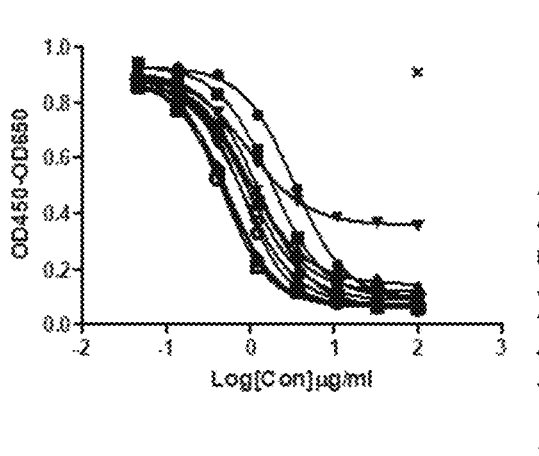
Figure 9:
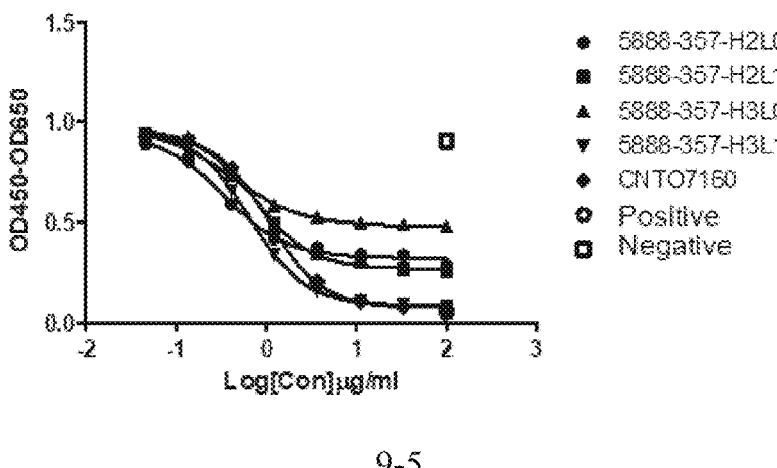
Figure 9:
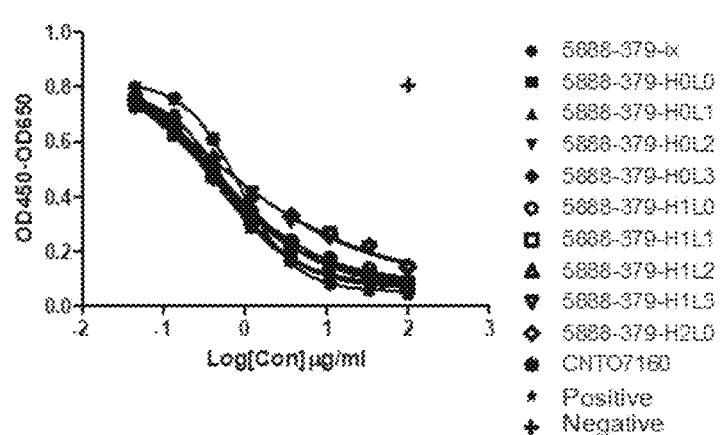
Figure 9:
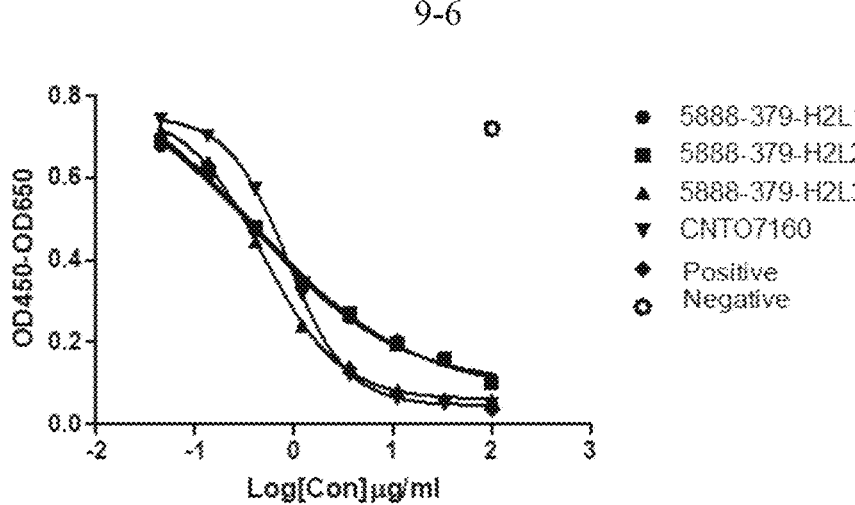

(2) Blocking Assay Screening of Humanized Antibodies on the Binding of IL33 to Human ST2 Detection was performed according to the experiment procedure described in section 2.2, "(3) Blocking assay screening of murine antibodies on the binding of IL33 to human ST2" above. Results are shown in FIG. 9 and Table 23. In FIG. 9, the negative control is a mixture of blank medium and diluted human IL33-his at a 1:1 ratio, and the positive control is blank medium.

TABLE 23

Blocking assay screening of humanized
antibodies on the binding of IL33 to human ST2
and relative activity of the antibodies compared with CNTO7160

| Antibody | IC$_{50}$ (µg/mL) | Relative activity | Maximum inhibition rate |
|---|---|---|---|
| 5886-156-H1L0 | 1.217 | 103.12% | 89.24% |
| 5886-156-H1L1 | 1.004 | 125.00% | 88.05% |
| 5887-41-H1L0 | 0.5802 | 216.30% | 92.76% |
| 5887-41-H1L1 | 2.231 | 56.25% | 92.41% |
| 5887-537-H1L0 | 0.08819 | 1205.35% | 88.29% |
| 5888-116-H0L1 | 0.02045 | 5198.04% | 94.09% |
| 5888-116-H1L1 | 0.4863 | 218.59% | 94.89% |
| 5888-116-H3L1 | 0.6112 | 186.52% | 90.65% |
| 5888-153-H0L0 | 2.571 | 44.34% | 92.89% |
| 5888-153-H0L1 | 0.3003 | 379.62% | 94.33% |

TABLE 23-continued

Blocking assay screening of humanized
antibodies on the binding of IL33 to human ST2
and relative activity of the antibodies compared with CNTO7160

| Antibody | IC$_{50}$ (μg/mL) | Relative activity | Maximum inhibition rate |
|---|---|---|---|
| 5888-153-H0L2 | 0.4742 | 240.40% | 93.53% |
| 5888-153-H1L0 | 1.322 | 86.23% | 92.52% |
| 5888-153-H1L1 | 0.6241 | 182.66% | 93.75% |
| 5888-153-H1L2 | 0.852 | 133.80% | 93.95% |
| 5888-153-H3L1 | 0.5531 | 227.81% | 93.67% |
| 5888-153-H3L2 | 0.8284 | 152.10% | 93.67% |
| 5888-357-H1L1 | 0.4896 | 257.35% | 93.24% |
| 5888-379-H0L0 | 0.4878 | 179.56% | 90.55% |
| 5888-379-H1L0 | 0.4653 | 188.24% | 89.14% |
| 5888-379-H1L1 | 0.3173 | 276.05% | 89.48% |
| 5888-379-H2L1 | 0.4273 | 206.06% | 84.83% |
| 5888-379-H2L2 | 0.4022 | 218.92% | 86.05% |
| CNTO7160 | | | 92.55% |

(3) Inhibitory Activity of Humanized Antibodies on the Promotion of KU812-IL5 Production by IL-33

Figure 10:
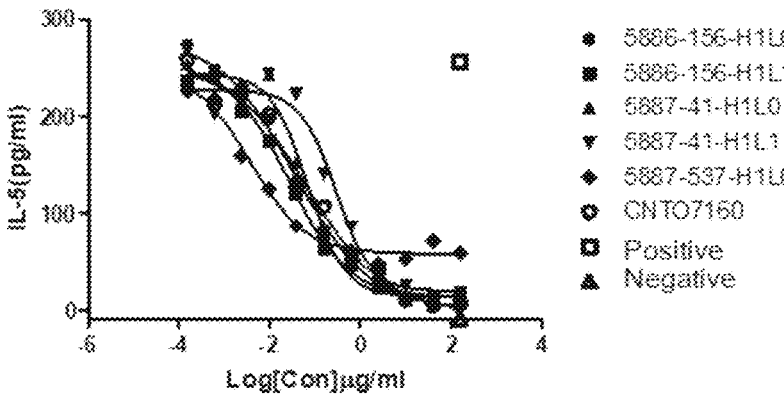
FIG. 10 shows inhibitory activity of humanized antibodies on the promotion of KU812-IL5 production by IL-33.
Figure 10:
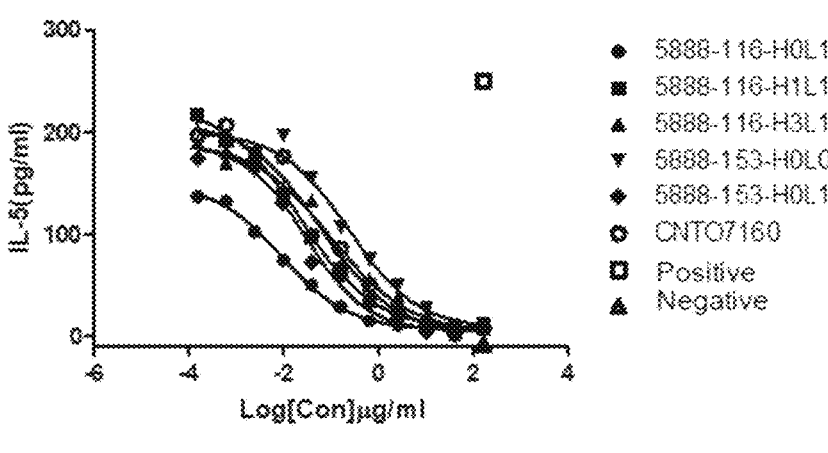
Figure 10:
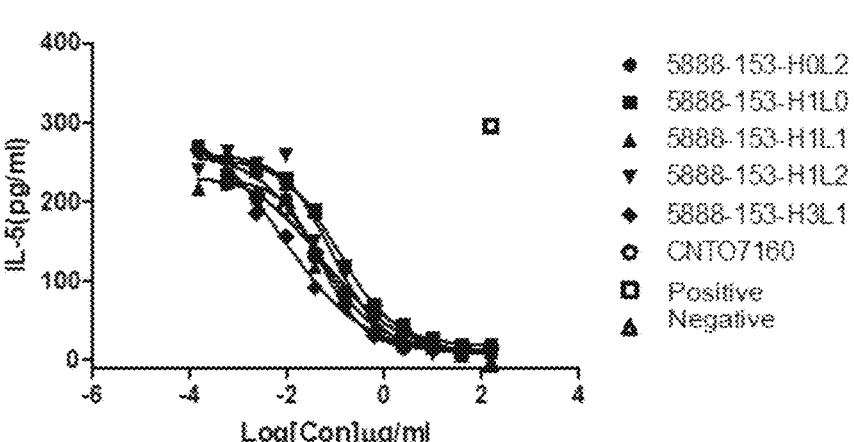
Figure 10:
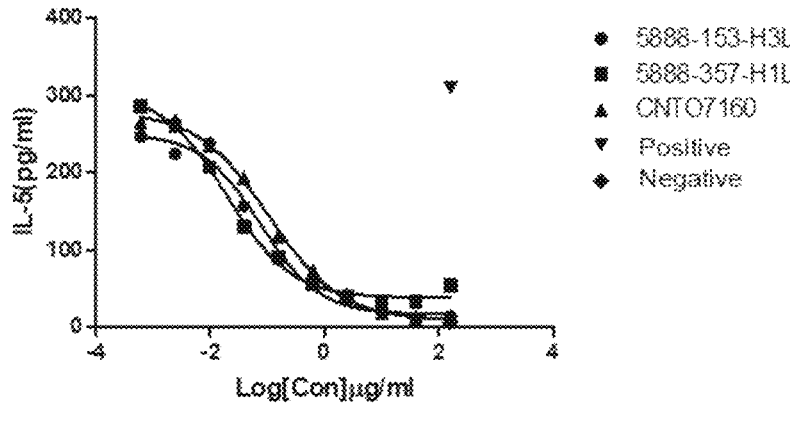
Figure 10:
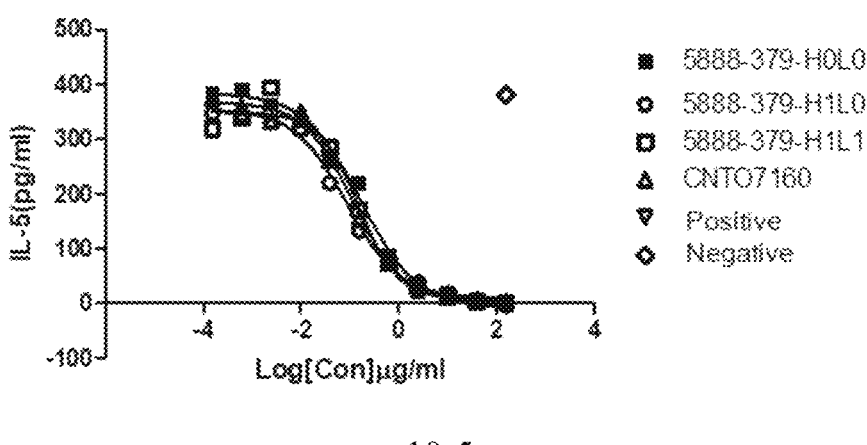
Figure 10:
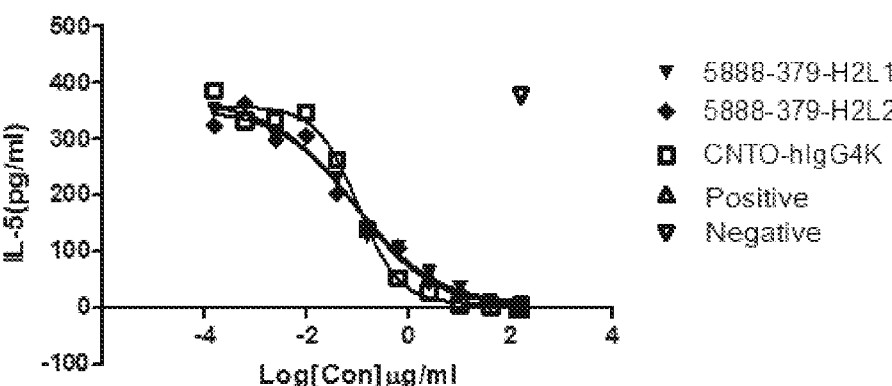

Human IL33-his was diluted with culture medium to 80 ng/mL. Each humanized antibody was diluted with culture medium to 640 μg/mL and then was diluted 4-fold to obtain serial dilutions of 11 concentrations in total. The diluted antibodies were mixed with the diluted human IL33-his at a 1:1 ratio, and the mixtures obtained were added into 96-well plates at 50 μL/well. Subsequent experiment procedure was the same as that described in section 2.2, "(6) In vitro pharmacological study of murine antibodies" above. Results are shown in FIG. 10 and Table 24. In FIG. 10, the negative control is a mixture of blank medium and diluted human IL33-his at a 1:1 ratio, and the positive control is blank medium.

TABLE 24

Inhibitory activity of humanized antibodies on the
promotion of KU812-IL5 production by IL-33 and relative
activity of the antibodies compared with CNTO7160

| Antibody | IC$_{50}$ (μg/mL) | Relative activity | Maximum inhibition rate |
|---|---|---|---|
| 5886-156-H1L0 | 0.03539 | 181.12% | 98.07% |
| 5886-156-H1L1 | 0.02893 | 221.57% | 94.95% |
| 5887-41-H1L0 | 0.0699 | 91.70% | 97.27% |
| 5888-116-H0L1 | 0.009289 | 656.37% | 98.31% |
| 5888-153-H0L1 | 0.03033 | 201.02% | 99.11% |
| 5888-153-H3L1 | 0.008149 | 741.93% | 97.02% |
| 5888-153-H3L2 | 0.07554 | 142.04% | 94.24% |
| 5888-379-H1L0 | 0.0874 | 131.01% | 99.40% |
| 5888-379-H2L1 | 0.08393 | 121.17% | 97.95% |
| 5888-379-H2L2 | 0.09478 | 107.30% | 97.88% |
| CNTO7160 | | | 97.55% |

(4) Screening of Humanized Antibodies on the Activation of KU82-NF-κB Reporter Gene by L33

Detection was performed according to the experiment procedure described in section 2.2, "(4) Screening of murine antibodies on the activation of KU812-NF-κB reporter gene by IL33" above. Results are shown Table 25.

TABLE 25

Screening of humanized antibodies on the activation
of KU812-NF-κB reporter gene by IL33 and relative
activity of the antibodies compared with CNTO7160

| Antibody | IC$_{50}$ (ng/mL) | Relative activity | Maximum inhibition rate |
|---|---|---|---|
| 5886-156-H1L0 | 477.9 | 41.91% | 92.49% |
| 5887-41-H1L0 | 55.35 | 361.88% | 89.24% |
| 5888-116-H0L1 | 13.03 | 1537.22% | 95.74% |
| 5888-153-H0L1 | 43.78 | 457.51% | 88.24% |
| 5888-153-H1L1 | 12.36 | 1620.55% | 91.36% |
| 5888-153-H1L2 | 44.07 | 454.50% | 84.98% |
| 5888-153-H3L1 | 39.42 | 508.12% | 86.11% |
| 5888-153-H3L2 | 55.28 | 362.34% | 88.11% |
| CNTO7160 | 200.3 | | 88.24% |

(5) Inhibitory Activity of Humanized Antibodies on the Promotion of KU812-IL5 Production by Oxidized IL-33

Figure 11:
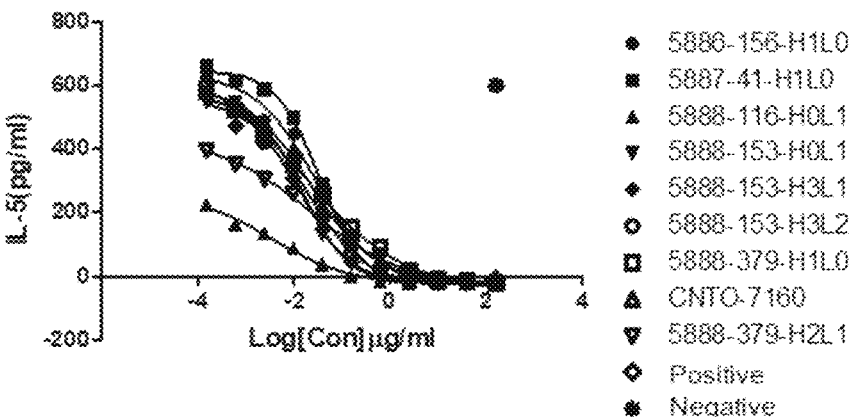
FIG. 11 shows inhibitory activity of humanized antibodies on the promotion of KU812-IL5 production by oxidized IL-33.

Oxidized human IL33-his was diluted with culture medium to 200 ng/mL. Each humanized antibody was diluted with culture medium to 640 μg/mL and then was diluted 4-fold to obtain serial dilutions of 11 concentrations in total. The diluted antibodies were mixed with the diluted human IL33-his at a 1:1 ratio, and the mixtures obtained were added into 96-well plates at 50 μL/well. Subsequent experiment procedure was the same as that described in section 2.2, "(6) In vitro pharmacological study of murine antibodies" above. Results are shown in FIG. 11 and Table 26. In FIG. 11, the negative control is a mixture of blank medium and diluted human IL33-his at a 1:1 ratio, and the positive control is blank medium.

TABLE 26

Inhibitory activity of humanized antibodies on the promotion
of KU812-IL5 production by oxidized IL33

| Antibody | IC$_{50}$ (μg/mL) | Relative activity | Maximum inhibition rate |
|---|---|---|---|
| 5886-156-H1L0 | 0.0285 | 77.49% | 101.11% |
| 5887-41-H1L0 | 0.0337 | 65.40% | 101.12% |
| 5888-116-H0L1 | 0.0036 | 614.14% | 101.56% |
| 5888-153-H0L1 | 0.0147 | 150.07% | 101.47% |
| 5888-153-H3L1 | 0.0136 | 161.97% | 101.38% |
| 5888-153-H3L2 | 0.0173 | 127.44% | 101.37% |
| 5888-379-H1L0 | 0.0161 | 137.27% | 101.34% |
| 5888-379-H2L1 | 0.0228 | 96.84% | 101.14% |
| CNTO7160 | 0.0221 | 100.00% | 98.90% |

(6) Inhibitory Activity of Humanized Antibodies on the Promotion of KU812-IL5 Production by Reduced IL-33

Figure 12:
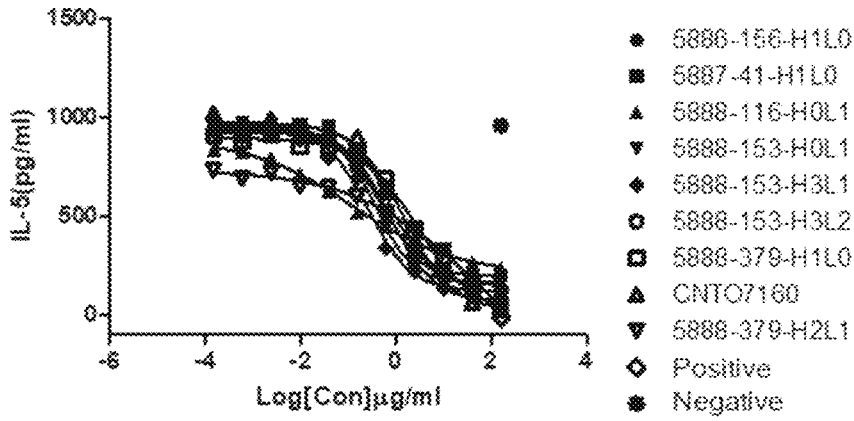
FIG. 12 shows inhibitory activity of humanized antibodies on the promotion of KU812-IL5 production by reduced IL-33.

Reduced human IL33-his was diluted with culture medium to 6 ng/mL. Each humanized antibody was diluted with culture medium to 640 μg/mL and then was diluted 4-fold to obtain serial dilutions of 11 concentrations in total. The diluted antibodies were mixed with the diluted human IL33-his at a 1:1 ratio, and the mixtures obtained were added into 96-well plates at 50 μL/well. Subsequent experiment procedure was the same as that described in section 2.2, "(6) In vitro pharmacological study of murine antibodies" above. Results are shown in FIG. 12 and Table 27. In FIG. 12, the negative control is a mixture of blank medium and diluted human IL33-his at a 1:1 ratio, and the positive control is blank medium.

TABLE 27

Inhibitory activity of humanized antibodies on the promotion
of KU812-IL5 production by reduced IL33

| Antibody | IC$_{50}$ (µg/mL) | Relative activity | Maximum inhibition rate |
|---|---|---|---|
| 5886-156-H1L0 | 0.7524 | 194.71% | 93.38% |
| 5887-41-H1L0 | 0.7056 | 207.62% | 78.62% |
| 5888-116-H0L1 | 0.1245 | 1176.71% | 75.06% |
| 5888-153-H0L1 | 0.3891 | 376.51% | 83.56% |
| 5888-153-H3L1 | 0.2646 | 553.67% | 86.93% |
| 5888-153-H3L2 | 0.5218 | 280.76% | 87.24% |
| 5888-379-H1L0 | 2.8650 | 51.13% | 96.68% |
| 5888-379-H2L1 | 2.8650 | 51.13% | 96.68% |
| CNTO7160 | 1.4650 | 100.00% | 97.30% |

(7) Inhibitory Activity of Humanized Antibodies on the Promotion of HUVEC-IL6 Production by 1L33

In 96-well plates, HUVEC cells were incubated at 10000/well and 100 µL/well at 37° C., 5% CO$_2$ for 18-24 hrs. Human IL33-his was diluted with culture medium to 10 ng/mL. Each humanized antibody was diluted with culture medium to 400 µg/mL and then was diluted 4-fold to obtain serial dilutions of 11 concentrations in total. The diluted antibodies were mixed with the diluted human IL33-his at a 1:1 ratio, and the mixtures obtained were added into the 96-well plates above at 50 µL/well, which were then incubated at 37° C., 5% CO$_2$ for 18-24 hrs.

Figure 13:
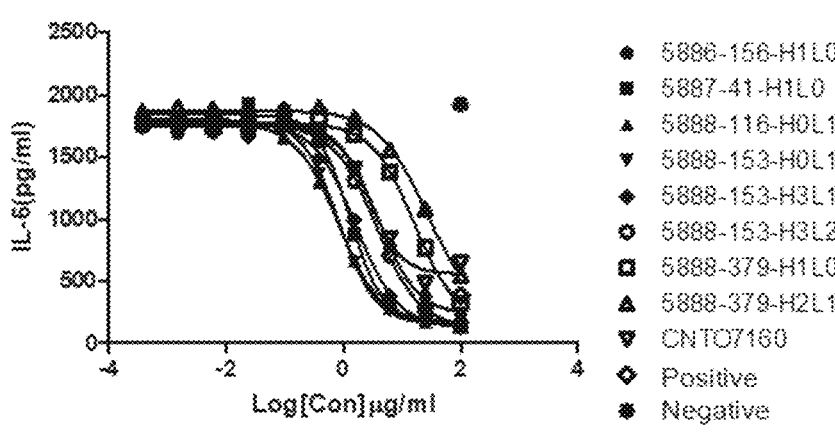
FIG. 13 shows inhibitory activity of humanized antibodies on the promotion of HUVEC-IL6 production by IL33.

As a 2 µg/mL working solution obtained by 120-fold diluting a stock solution of 240 µg/mL with PBS, the capture antibody contained in Human IL-6 DuoSet ELISA kit was coated at 50 µL/well in ELISA plates at 4° C. overnight, according to the instructions one day in advance. Then the plates were blocked using a blocking buffer for 1 hr, and then washed for 3 times. A 180 ng/mL standard was diluted 300-fold to 600 pg/mL and then diluted 2-fold to obtain serial dilutions of 7 concentrations in total. Culture supernatant of the cells above and one of the diluted standards, 50 µL each, were pipetted into the ELISA plates, and incubated for 2 hrs. The plates were washed for 3 times, and a 50 ng/mL working solution obtained by 60-fold diluting a detection antibody (in a stock solution of 3 µg/mL) was added at 50 µL/well into the plates which were then incubated for 2 hrs. The plates were washed for 3 times again, and a 125 ng/mL working solution obtained by 40-fold diluting SA-HRP was added at 50 µL/well into the plates which were then incubated for 20-30 min. Substrate solution was added into the plates at 50 µL/well to develop color in dark for 5-10 min. Afterwards, 2 M sulfuric acid was added at 100 µL/well to stop reaction; and OD values at 450 nm and 650 nm were read by a microplate reader. Results are shown in Table 28 and FIG. 13. In FIG. 13, the negative control is a mixture of blank medium and diluted human IL33-his at a 1:1 ratio, and the positive control is blank medium.

TABLE 28

Inhibitory activity of humanized antibodies on the promotion
of HUVEC-IL6 production by IL33

| Antibody | IC50 (µg/mL) | Relative activity | Maximum inhibition rate |
|---|---|---|---|
| 5886-156-H1L0 | 4.051 | 67.29% | 87.89% |
| 5887-41-H1L0 | 1.308 | 208.41% | 93.20% |
| 5888-116-H0L1 | 0.8321 | 327.60% | 92.61% |
| 5888-153-H0L1 | 0.8435 | 323.18% | 92.99% |
| 5888-153-H3L1 | 1.636 | 166.63% | 93.05% |

TABLE 28-continued

Inhibitory activity of humanized antibodies on the promotion
of HUVEC-IL6 production by IL33

| Antibody | IC50 (µg/mL) | Relative activity | Maximum inhibition rate |
|---|---|---|---|
| 5888-153-H3L2 | 3.688 | 73.92% | 91.85% |
| 5888-379-H1L0 | 16.1 | 16.93% | 83.05% |
| 5888-379-H2L1 | 26.14 | 10.43% | 71.60% |
| CNTO7160 | 2.726 | 100.00% | 66.59% |

(8) Inhibitory Activity of Humanized Antibodies on the Promotion of HMC-1 IL8 Production by IL33

Human IL33-his was diluted to a final concentration of 1000 ng/mL. Starting at 640 µg/mL, each of humanized antibodies was diluted 4-fold to obtain serial dilutions of 11 concentrations in total. The diluted antibodies were mixed with the diluted human IL33-his at a 1:1 ratio, and the mixtures obtained were added into 96-well plates at 50 µL/well. HMC-1 cells in logarithmic growth phase were taken, added into the 96-well plates at 50000/well and 50 µL/well, and incubated at 37° C., 5% CO$_2$ for 18-24 hrs.

Figure 14:
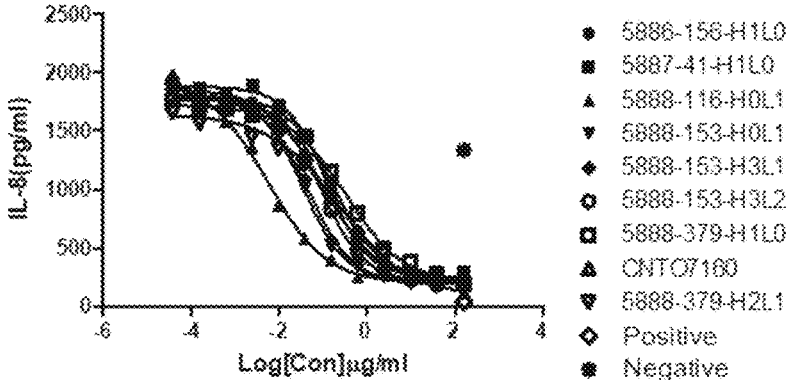
FIG. 14 shows inhibitory activity of humanized antibodies on the promotion of HMC-1-IL8 production by IL33.

As a working solution obtained by 120-fold diluting with PBS, the capture antibody contained in Human IL-8 DuoSet ELISA kit was coated at 50 µL/well in ELISA plates at 4° C. overnight, according to the instructions one day in advance. Then the plates were blocked using a blocking buffer for 1 hr, and then washed for 3 times. A standard was diluted 40-fold to 2000 µg/mL and then diluted 2-fold to obtain serial dilutions of 7 concentrations in total. Culture supernatant of the cells above and one of the diluted standards, 50 µL each, were pipetted into the ELISA plates, and incubated for 2 hrs. The plates were washed for 3 times, and a working solution obtained by 60-fold diluting a detection antibody was added at 50 µL/well into the plates which were then incubated for 2 hrs. The plates were washed for 3 times again, and a 125 ng/mL working solution obtained by 40-fold diluting SA-HRP was added at 50 µL/well into the plates which were then incubated for 20-30 min. Substrate solution was added into the plates at 50 µL/well to develop color in dark for 5-10 min. Afterwards, 2 M sulfuric acid was added at 100 µL/well to stop reaction; and OD values at 450 nm and 650 nm were read by a microplate reader. Results are shown in Table 29 and FIG. 14. In FIG. 14, the negative control is a mixture of blank medium and diluted human IL33-his at a 1:1 ratio, and the positive control is blank medium.

TABLE 29

Inhibitory activity of humanized antibodies on the promotion
of HMC-1 IL8 production by IL33

| Antibody | IC50 (µg/mL) | Relative activity | Maximum inhibition rate |
|---|---|---|---|
| 5886-156-H1L0 | 0.1771 | 56.86% | 81.01% |
| 5887-41-H1L0 | 0.1234 | 81.60% | 77.81% |
| 5888-116-H0L1 | 0.005512 | 1826.92% | 90.57% |
| 5888-153-H0L1 | 0.03592 | 280.35% | 87.17% |
| 5888-153-H3L1 | 0.04719 | 213.39% | 86.75% |
| 5888-153-H3L2 | 0.09443 | 106.64% | 83.30% |
| 5888-379-H1L0 | 0.334 | 30.15% | 85.60% |
| 5888-379-H2L1 | 0.2298 | 43.82% | 90.15% |
| CNTO7160 | 0.1007 | | 82.34% |

(9) Determination of Affinity of Humanized Antibodies

The experiment on the interaction between the anti-human ST2 antibodies and human ST2-his was performed using Biacore X100.

(9-1) Affinity Experiment of Dissociation Kinetics of Human ST2 from Humanized Antibodies at pH 7.4: The Experiment was Carried Out at 25° C. In HBS-EP (1×) Buffer (pH 7.4).

Each anti-human ST2 antibody was diluted to 2 µg/mL and captured on the surface of a protein A chip for a capture time of 60 s. Following the antibody capture, a solution of human ST2-his (2-fold gradient dilution from a starting concentration of 20 nM, to obtain 6 concentrations in total) was injected. Association was monitored for 180 s and dissociation was monitored for 700 s, and the sensor surface was regenerated by injecting a solution of glycine at pH 2.0. Kinetic data were analyzed using a simple 1:1 binding model.

(9-2) Affinity Experiment of Dissociation Kinetics of Human ST2 from Humanized Antibodies at pH 5.5:

The experiment was performed according to the experiment procedure described in (9-1), with differences that the dissociation was performed in HBS-EP (1×) buffer, pH 5.5 and the dissociation was monitored for 600 s.

Results are shown in Table 30.

(1) Coating: human ST2-his was diluted to 1 µg/mL with PBS (pH 7.2-7.4), added to 96-well ELSIA plates at 50 µL/well, which were then sealed with film. The plates were stewing at 2-8° C. for 15-20 hrs, and then washed with PBST (containing 0.05% (v/v) Tween-20, pH 7.2-7.4) for 3 times.

(2) Blocking and drying: the plates were blocked with N502 at 200 µL/well at room temperature for 1-2 hrs. After the blocking solution was aspirated off, the plates were dried in an incubator at 25° C. for >1 h, and then used immediately, or sealed with film and stored at 2-8° C.

(3) Preparing standards used for plotting standard curve and quality controls: an antibody sample was diluted to 1000 ng/mL using mouse plasma (EDTA-K), followed by 2-fold gradient dilution to 15 ng/mL (7 concentrations including 1000 ng/mL). Besides, the same antibody sample used for plotting standard curve was quantitatively diluted to a concentration within a concentration range for quantitative analysis, and used as

TABLE 30

| | Affinity of humanized antibodies at pH 7.4 and pH 5.5 | | | | | | |
| | Affinity (pH 7.4) | | | Affinity (pH 5.5) | | | kd ratio of |
| Antibody | ka (1/Ms) | kd (1/s) | KD (M) | ka (1/Ms) | kd (1/s) | KD (M) | pH 5.5/pH 7.4 |
|---|---|---|---|---|---|---|---|
| 5886-156-H1L0 | 9.90E+05 | 2.72E−04 | 2.75E−10 | 1.01E+06 | 2.79E−04 | 2.76E−10 | 1.03 |
| 5887-41-H1L0 | 4.67E+05 | 9.98E−05 | 2.14E−10 | 6.22E+05 | 1.00E−04 | 1.61E−10 | 1.00 |
| 5888-116-H0L1 | 1.79E+06 | 4.64E−04 | 2.59E−10 | 2.95E+06 | 1.40E−03 | 4.74E−10 | 3.02 |
| 5888-153-H0L1 | 1.76E+06 | 1.76E−04 | 9.97E−11 | 2.15E+06 | 1.52E−04 | 7.06E−11 | 0.86 |
| 5888-153-H3L1 | 1.53E+06 | 1.48E−04 | 9.70E−11 | 1.90E+06 | 2.32E−04 | 1.22E−10 | 1.57 |
| 5888-153-H3L2 | 1.65E+06 | 1.71E−04 | 1.04E−10 | 1.87E+06 | 2.45E−04 | 1.31E−10 | 1.43 |
| 5888-379-H1L0 | 7.77E+05 | 3.51E−04 | 4.52E−10 | 1.79E+06 | 2.55E−03 | 1.43E−09 | 7.26 |
| 5888-379-H2L1 | 9.79E+05 | 4.85E−04 | 4.95E−10 | 3.46E+06 | 5.75E−03 | 1.67E−09 | 11.86 |
| CNTO7160 | 7.63E+05 | 1.75E−04 | 2.29E−10 | 6.76E+05 | 2.67E−04 | 3.95E−10 | 1.53 |
| Ab2* | 7.58E+05 | 8.64E−05 | 1.14E−10 | 7.45E+05 | 3.93E−04 | 5.28E−10 | 4.55 |
| 5888-379-H2L2 | 1.36E+06 | 7.02E−04 | 5.15E−10 | 1.01E+07 | 2.69E−02 | 2.67E−09 | 38.38 |
| 5886-156-H1L1 | 1.45E+06 | 3.77E−04 | 2.61E−10 | | | | |

*Antibody Ab2 in CN104334582B

Example 3: Pharmacokinetics of Antibodies in Mice

After an acclimation period, 20 mice were randomly divided into 4 groups, 5 mice in each. Administration information is shown in Table 31.

TABLE 31

| | Administration information for each group of mice | | |
| | Antibody | Mode of administration | Volume of administration |
|---|---|---|---|
| A | 5888-116-H0L1 | 5 mg/kg, i.p. | 0.1 mL/10 g |
| B | 5888-153-H0L1 | 5 mg/kg, i.p. | 0.1 mL/10 g |
| C | CNTO7160 | 5 mg/kg, i.p. | 0.1 mL/10 g |
| D | 5886-156-H1L0 | 5 mg/kg, i.p. | 0.1 mL/10 g |

The mice were administrated according to the grouping, and time of administration was recorded. Blood of the mice in each group was sampled before administration (0 h), and 4 hrs, 8 hrs, 24 hrs (1 d), 72 hrs (3 d), 120 hrs (5 d), 168 hrs (7 d), 240 hrs (10 d), 288 hrs (12 d), and 336 hrs (14 d) after administration, and sera were collected and stored at −60 to −80° C.

Blood drug concentration for PK study in mouse was detected as follows:

a quality control (QC). Specifically, the antibody sample was diluted to 1000 ng/mL, 100 ng/mL and 20 ng/mL respectively.

(4) Preparing samples to be detected: samples at different blood sampling time points were obtained and diluted to a concentration within the concentration range used for plotting standard curve.

(5) Diluting standards, quality controls and samples: the standards, quality controls and samples were diluted 10-fold with 0.1% casein (pH 6.2, obtained by diluting a stock solution of casein with PBS, pH 6.2) (for example, 10 L diluted with 90 L) and added to the dried plates at 50 µL/well, 2 replicates per sample. The plates were sealed with film and incubated at room temperature for 2 hrs, and then washed with PBST (containing 0.05% (v/v) Tween-20, pH 7.2-7.4) for 3 times.

(6) Incubating with a secondary antibody: a goat anti-Human IgG Fc-HRP was diluted 50000-fold with 10% goat serum, added to the plates at 50 µL/well, which were then sealed and incubated at room temperature for 1 hr. Afterwards, the plates were washed with PBST (containing 0.05% (v/v) Tween-20, pH 7.2-7.4) for 3 times.

(7) Color developing: TMB which had been warmed to room temperature was added to the plates at 50 μL/well to develop color in dark for 20 min.

(8) Stopping reaction and reading OD values: 2 M sulfuric acid was added at 100 μL/well into the plates, which were then tapped to mix the sulfuric acid homogenously. The concentration of each sample tested was calculated using OD readings at 450 nm, with 650 nm as reference.

Figure 15:
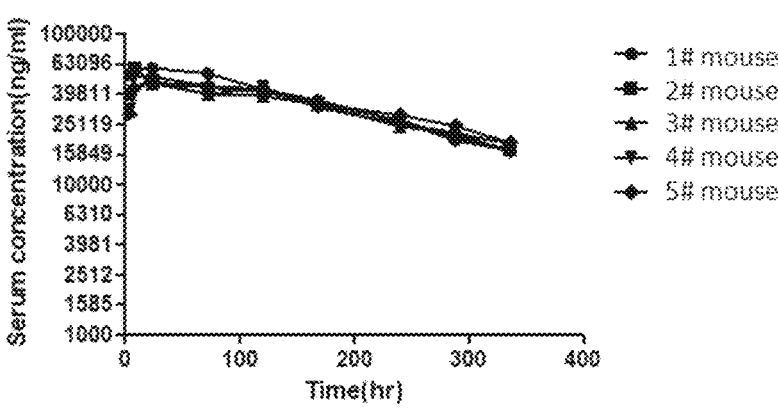
FIG. 15 shows PK curves of the humanized antibodies in mice, in which panel 15-1: 5888-116-H0L1; panel 15-2: 5888-153-H0L1; panel 15-3: CNTO7160; panel 15-4: 5886-156-H1L0.
Figure 15:
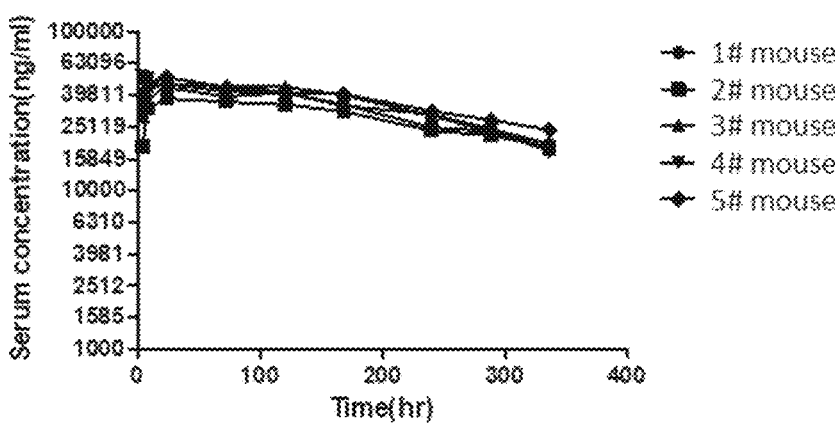
Figure 15:
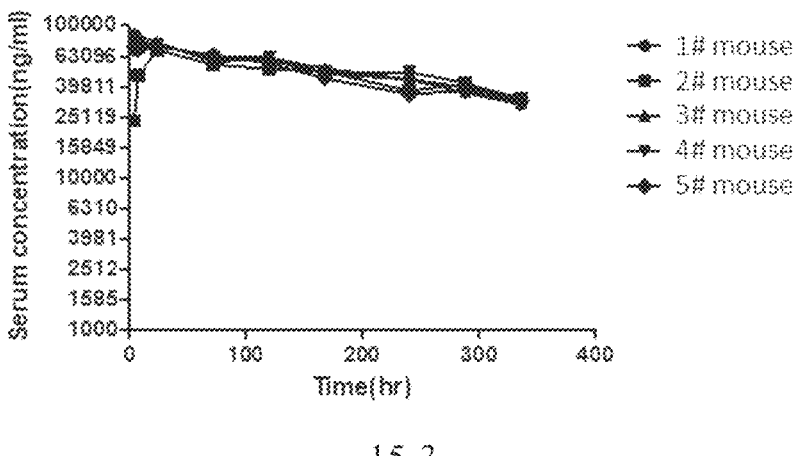
Figure 15:
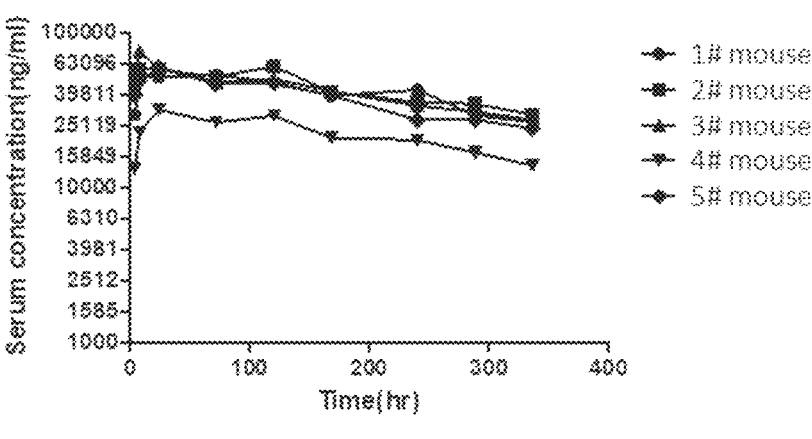

Experiment results showed that three antibodies had a half-life longer than 100 hrs, specifically ordered as 5886-156-H1L0>5888-153-H0L1>5888-116-H0L1. Among the three antibodies, antibody 5886-156H1L0 had a half-life reaching 10 days, equivalent to that of CNTO7160. The results are shown in FIG. 15 and Table 32.

TABLE 32

| | PK parameters of antibodies in mice | | | |
|---|---|---|---|---|
| Parameter | 5888-116-H0L1 | 5888-153-H0L1 | CNTO7160 | 5886-156-H1L0 |
| $t_{1/2}$ (h) | 174.78 | 191.46 | 241.97 | 241.18 |
| Cmax (kg * ng/ml/mg) | 10972.58 | 9380.59 | 15733.80 | 11319.84 |
| AUC (h * ng/ml) | 11509209.16 | 11404571.90 | 17097590.16 | 12860587.84 |
| CL (ml/h/kg) | 0.31 | 0.30 | 0.18 | 0.26 |
| MRT (h) | 139.03 | 146.65 | 146.40 | 147.33 |

The above description of the embodiments of the present invention is not intended to limit the present invention, and those skilled in the art may make various changes and modifications to the present invention without departing from the spirit of the present invention, which should fall within the scope of the appended claim

What is claimed is:

1. An antibody or fragment thereof comprising a heavy chain variable region (VH) and a light chain variable region (VL), wherein the heavy chain variable region and the light chain variable region comprise heavy chain CDRs and light chain CDRs shown in any one selected from the following combinations:

(1) H-CDR1, H-CDR2, H-CDR3 as shown in SEQ ID NOs. 56, 63, 70 sequentially; and, L-CDR1, L-CDR2, L-CDR3 as shown in SEQ ID NOs. 85, 93, 97 sequentially;

(II-1): H-CDR1, H-CDR2, H-CDR3 as shown in SEQ ID NOs. 57, 64, 71 sequentially; and, L-CDR1, L-CDR2, L-CDR3 as shown in SEQ ID NOs. 86, 93, 98 sequentially;

(II-2): H-CDR1, H-CDR2, H-CDR3 as shown in SEQ ID NOs. 57, 64, 71 sequentially; and, L-CDR1, L-CDR2, L-CDR3 as shown in SEQ ID NOs. 87, 93, 98 sequentially;

(III): H-CDR1, H-CDR2, H-CDR3 as shown in SEQ ID NOs. 58, 65, 72 sequentially; and, L-CDR1, L-CDR2, L-CDR3 as shown in SEQ ID NOs. 88, 94, 99 sequentially;

(IV-1): H-CDR1, H-CDR2, H-CDR3 as shown in SEQ ID NOs. 59, 66, 73 sequentially; and, L-CDR1, L-CDR2, L-CDR3 as shown in SEQ ID NOs. 89, 95, 100 sequentially;

(IV-2): H-CDR1, H-CDR2, H-CDR3 as shown in SEQ ID NOs. 59, 66, 74 sequentially; and, L-CDR1, L-CDR2, L-CDR3 as shown in SEQ ID NOs. 89, 95, 100 sequentially;

(IV-3): H-CDR1, H-CDR2, H-CDR3 as shown in SEQ ID NOs. 59, 66, 75 sequentially; and, L-CDR1, L-CDR2, L-CDR3 as shown in SEQ ID NOs. 89, 95, 100 sequentially;

(V-1): H-CDR1, H-CDR2, H-CDR3 as shown in SEQ ID NOs. 60, 67, 76 sequentially; and, L-CDR1, L-CDR2, L-CDR3 as shown in SEQ ID NOs. 90, 95, 101 sequentially;

(V-2): H-CDR1, H-CDR2, H-CDR3 as shown in SEQ ID NOs. 60, 67, 76 sequentially; and, L-CDR1, L-CDR2, L-CDR3 as shown in SEQ ID NOs. 90, 95, 102 sequentially;

(V-3): H-CDR1, H-CDR2, H-CDR3 as shown in SEQ ID NOs. 60, 67, 77 sequentially; and, L-CDR1, L-CDR2, L-CDR3 as shown in SEQ ID NOs. 90, 95, 101 sequentially;

(V-4): H-CDR1, H-CDR2, H-CDR3 as shown in SEQ ID NOs. 60, 67, 77 sequentially; and, L-CDR1, L-CDR2, L-CDR3 as shown in SEQ ID NOs. 90, 95, 102 sequentially;

(V-5): H-CDR1, H-CDR2, H-CDR3 as shown in SEQ ID NOs. 60, 67, 78 sequentially; and, L-CDR1, L-CDR2, L-CDR3 as shown in SEQ ID NOs. 90, 95, 101 sequentially;

(V-6): H-CDR1, H-CDR2, H-CDR3 as shown in SEQ ID NOs. 60, 67, 78 sequentially; and, L-CDR1, L-CDR2, L-CDR3 as shown in SEQ ID NOs. 90, 95, 102 sequentially;

(VI-1): H-CDR1, H-CDR2, H-CDR3 as shown in SEQ ID NOs. 61, 68, 79 sequentially; and, L-CDR1, L-CDR2, L-CDR3 as shown in SEQ ID NOs. 91, 95, 100 sequentially;

(VI-2): H-CDR1, H-CDR2, H-CDR3 as shown in SEQ ID NOs. 61, 68, 80 sequentially; and, L-CDR1, L-CDR2, L-CDR3 as shown in SEQ ID NOs. 91, 95, 100 sequentially;

(VI-3): H-CDR1, H-CDR2, H-CDR3 as shown in SEQ ID NOs. 61, 68, 81 sequentially; and, L-CDR1, L-CDR2, L-CDR3 as shown in SEQ ID NOs. 91, 95, 100 sequentially;

(VII-1): H-CDR1, H-CDR2, H-CDR3 as shown in SEQ ID NOs. 62, 69, 82 sequentially; and, L-CDR1, L-CDR2, L-CDR3 as shown in SEQ ID NOs. 92, 96, 103 sequentially;

(VII-2): H-CDR1, H-CDR2, H-CDR3 as shown in SEQ ID NOs. 62, 69, 83 sequentially; and, L-CDR1, L-CDR2, L-CDR3 as shown in SEQ ID NOs. 92, 96, 103 sequentially; and (VII-3): H-CDR1, H-CDR2, H-CDR3 as shown in SEQ ID NOs. 62, 69, 84 sequentially; and, L-CDR1, L-CDR2, L-CDR3) as shown in SEQ ID NOs. 92, 96, 103 sequentially.

2. The antibody or fragment thereof according to claim 1, wherein the heavy chain variable region comprises an amino acid sequence as shown in any one of SEQ ID NO. 1 to SEQ ID NO. 28 or an amino acid sequence having at least 75% identity to the amino acid sequence as shown; and/or, the light chain variable region comprises an amino acid sequence as shown in any one of SEQ ID NO. 29 to SEQ ID NO. 53 or an amino acid sequence having at least 75% identity to the amino acid sequence as shown.

3. The antibody or fragment thereof according to claim 1, wherein the antibody or fragment thereof comprises a heavy chain variable region and a light chain variable region as shown in any one selected from the following combinations:

(I-1): the heavy chain variable region as shown in SEQ ID NO. 1 and the light chain variable region as shown in SEQ ID NO. 29;

(I-2): the heavy chain variable region as shown in SEQ ID NO. 2 and the light chain variable region as shown in SEQ ID NO. 30;

(I-3): the heavy chain variable region as shown in SEQ ID NO. 2 and the light chain variable region as shown in SEQ ID NO. 31;

(I-4): the heavy chain variable region as shown in SEQ ID NO. 3 and the light chain variable region as shown in SEQ ID NO. 30;

(I-5): the heavy chain variable region as shown in SEQ ID NO. 3 and the light chain variable region as shown in SEQ ID NO. 31;

(II-1): the heavy chain variable region as shown in SEQ ID NO. 4 and the light chain variable region as shown in SEQ ID NO. 32;

(II-2): the heavy chain variable region as shown in SEQ ID NO. 5 and the light chain variable region as shown in SEQ ID NO. 33;

(II-3): the heavy chain variable region as shown in SEQ ID NO. 5 and the light chain variable region as shown in SEQ ID NO. 34;

(II-4): the heavy chain variable region as shown in SEQ ID NO. 5 and the light chain variable region as shown in SEQ ID NO. 35;

(II-5): the heavy chain variable region as shown in SEQ ID NO. 6 and the light chain variable region as shown in SEQ ID NO. 33;

(II-6): the heavy chain variable region as shown in SEQ ID NO. 6 and the light chain variable region as shown in SEQ ID NO. 34;

(II-7): the heavy chain variable region as shown in SEQ ID NO. 6 and the light chain variable region as shown in SEQ ID NO. 35;

(III-1): the heavy chain variable region as shown in SEQ ID NO. 7 and the light chain variable region as shown in SEQ ID NO. 36;

(III-2): the heavy chain variable region as shown in SEQ ID NO. 8 and the light chain variable region as shown in SEQ ID NO. 37;

(III-3): the heavy chain variable region as shown in SEQ ID NO. 8 and the light chain variable region as shown in SEQ ID NO. 38;

(III-4): the heavy chain variable region as shown in SEQ ID NO. 9 and the light chain variable region as shown in SEQ ID NO. 37;

(III-5): the heavy chain variable region as shown in SEQ ID NO. 9 and the light chain variable region as shown in SEQ ID NO. 38;

(IV-1): the heavy chain variable region as shown in SEQ ID NO. 10 and the light chain variable region as shown in SEQ ID NO. 39;

(IV-2): the heavy chain variable region as shown in SEQ ID NO. 11 and the light chain variable region as shown in SEQ ID NO. 40;

(IV-3): the heavy chain variable region as shown in SEQ ID NO. 11 and the light chain variable region as shown in SEQ ID NO. 41;

(IV-4): the heavy chain variable region as shown in SEQ ID NO. 12 and the light chain variable region as shown in SEQ ID NO. 40;

(IV-5): the heavy chain variable region as shown in SEQ ID NO. 12 and the light chain variable region as shown in SEQ ID NO. 41;

(IV-6): the heavy chain variable region as shown in SEQ ID NO. 13 and the light chain variable region as shown in SEQ ID NO. 40;

(IV-7): the heavy chain variable region as shown in SEQ ID NO. 13 and the light chain variable region as shown in SEQ ID NO. 41;

(IV-8): the heavy chain variable region as shown in SEQ ID NO. 14 and the light chain variable region as shown in SEQ ID NO. 40;

(IV-9): the heavy chain variable region as shown in SEQ ID NO. 14 and the light chain variable region as shown in SEQ ID NO. 41;

(V-1): the heavy chain variable region as shown in SEQ ID NO. 15 and the light chain variable region as shown in SEQ ID NO. 42;

(V-2): the heavy chain variable region as shown in SEQ ID NO. 16 and the light chain variable region as shown in SEQ ID NO. 43;

(V-3): the heavy chain variable region as shown in SEQ ID NO. 16 and the light chain variable region as shown in SEQ ID NO. 44;

(V-4): the heavy chain variable region as shown in SEQ ID NO. 16 and the light chain variable region as shown in SEQ ID NO. 45;

(V-5): the heavy chain variable region as shown in SEQ ID NO. 17 and the light chain variable region as shown in SEQ ID NO. 43;

(V-6): the heavy chain variable region as shown in SEQ ID NO. 17 and the light chain variable region as shown in SEQ ID NO. 44;

(V-7): the heavy chain variable region as shown in SEQ ID NO. 17 and the light chain variable region as shown in SEQ ID NO. 45;

(V-8): the heavy chain variable region as shown in SEQ ID NO. 18 and the light chain variable region as shown in SEQ ID NO. 43;

(V-9): the heavy chain variable region as shown in SEQ ID NO. 18 and the light chain variable region as shown in SEQ ID NO. 44;

(V-10): the heavy chain variable region as shown in SEQ ID NO. 18 and the light chain variable region as shown in SEQ ID NO. 45;

(V-11): the heavy chain variable region as shown in SEQ ID NO. 19 and the light chain variable region as shown in SEQ ID NO. 43;

(V-12): the heavy chain variable region as shown in SEQ ID NO. 19 and the light chain variable region as shown in SEQ ID NO. 44;

(V-13): the heavy chain variable region as shown in SEQ ID NO. 19 and the light chain variable region as shown in SEQ ID NO. 45;

(VI-1): the heavy chain variable region as shown in SEQ ID NO. 20 and the light chain variable region as shown in SEQ ID NO. 46;

(VI-2): the heavy chain variable region shown as SEQ ID NO. 21 and the light chain variable region shown as SEQ ID NO. 47;

(VI-3): the heavy chain variable region as shown in SEQ ID NO. 21 and the light chain variable region as shown in SEQ ID NO. 48;

(VI-4): the heavy chain variable region as shown in SEQ ID NO. 22 and the light chain variable region as shown in SEQ ID NO. 47;

(VI-5): the heavy chain variable region as shown in SEQ ID NO. 22 and the light chain variable region as shown in SEQ ID NO. 48;

(VI-6): the heavy chain variable region as shown in SEQ ID NO. 23 and the light chain variable region as shown in SEQ ID NO. 47;

(VI-7): the heavy chain variable region as shown in SEQ ID NO. 23 and the light chain variable region as shown in SEQ ID NO. 48;

(VI-8): the heavy chain variable region as shown in SEQ ID NO. 24 and the light chain variable region as shown in SEQ ID NO. 47;

(VI-9): the heavy chain variable region as shown in SEQ ID NO. 24 and the light chain variable region as shown in SEQ ID NO. 48;

(VII-1): the heavy chain variable region as shown in SEQ ID NO. 25 and the light chain variable region as shown in SEQ ID NO. 49;

(VII-2): the heavy chain variable region as shown in SEQ ID NO. 26 and the light chain variable region as shown in SEQ ID NO. 52;

(VII-3): the heavy chain variable region shown as SEQ ID NO. 26 and the light chain variable region shown as SEQ ID NO. 53;

(VII-4): the heavy chain variable region as shown in SEQ ID NO. 26 and the light chain variable region as shown in SEQ ID NO. 50;

(VII-5): the heavy chain variable region shown as SEQ ID NO. 26 and the light chain variable region shown as SEQ ID NO. 51;

(VII-6): the heavy chain variable region shown as SEQ ID NO. 27 and the light chain variable region shown as SEQ ID NO. 52;

(VII-7): the heavy chain variable region shown as SEQ ID NO. 27 and the light chain variable region shown as SEQ ID NO. 53;

(VII-8): the heavy chain variable region shown as SEQ ID NO. 27 and the light chain variable region shown as SEQ ID NO. 50;

(VII-9): the heavy chain variable region shown as SEQ ID NO. 27 and the light chain variable region shown as SEQ ID NO. 51;

(VII-10): the heavy chain variable region as shown in SEQ ID NO. 28 and the light chain variable region as shown in SEQ ID NO. 52;

(VII-11): the heavy chain variable region as shown in SEQ ID NO. 28 and the light chain variable region as shown in SEQ ID NO. 53;

(VII-12): the heavy chain variable region as shown in SEQ ID NO. 28 and the light chain variable region as shown in SEQ ID NO. 50; and (VII-13): the heavy chain variable region as shown in SEQ ID NO. 28 and the light chain variable region as shown in SEQ ID NO. 51.

4. The antibody or fragment thereof according to claim 1, wherein the antibody or fragment thereof binds to human ST2.

5. The antibody or fragment thereof according to claim 1, wherein the antibody is a monoclonal antibody, a single chain antibody, a diabody, a single domain antibody, a nanobody, a fully or partially humanized antibody, or a chimeric antibody; and the fragment is a functionally active fragment of the antibody which is capable of specifically binding to ST2 or any portion thereof.

6. A conjugate or fusion protein comprising the antibody or fragment thereof according to claim 1.

7. A composition comprising the antibody or fragment thereof according to claim 1, a conjugate or fusion protein comprising the antibody or fragment thereof, a nucleic acid molecule comprising a nucleotide sequence encoding a heavy chain CDR, a light chain CDR, a heavy chain variable region, a light chain variable region, a heavy chain or a light chain comprised in the antibody or fragment thereof, a vector comprising the nucleic acid molecule, and/or a host cell comprising the nucleic acid molecule and/or the vector, or transformed or transfected with the nucleic acid molecule and/or the vector.

8. The composition according to claim 7 manufactured to be a medicament for reducing the likelihood of treating, or ameliorating a disease associated with expression of ST2 or dysregulation of IL-33/ST2 pathway.

9. The composition according to claim 7 wherein the composition is a pharmaceutical composition.

10. The composition according to claim 8, wherein the disease is an inflammatory disease or an autoimmune disease.

11. The composition according to claim 8, wherein the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea.

12. A pharmaceutical combination comprising the antibody or fragment thereof according to claim 1, a conjugate or fusion protein comprising the antibody or fragment thereof, and/or a composition comprising the antibody or fragment thereof or the conjugate or fusion protein, and optionally an additional drug.

13. A kit comprising the antibody or fragment thereof according to claim 1, a conjugate or fusion protein comprising the antibody or fragment thereof, a nucleic acid molecule comprising a nucleotide sequence encoding a heavy chain CDR, a light chain CDR, a heavy chain variable region, a light chain variable region, a heavy chain or a light chain comprised in the antibody or fragment thereof, a vector comprising the nucleic acid molecule, and/or a host cell comprising the nucleic acid molecule and/or the vector, or transformed or transfected with the nucleic acid molecule and/or the vector, and/or a composition comprising the antibody or fragment thereof, the conjugate or fusion protein, the nucleic acid molecule, the vector, and/or the host cell.

14. A nucleic acid molecule comprising a nucleotide sequence encoding a heavy chain CDR, a light chain CDR, a heavy chain variable region, a light chain variable region, a heavy chain or a light chain comprised in the antibody or fragment thereof according to claim 1.

15. A vector comprising the nucleic acid molecule according to claim 14.

16. An isolated host cell comprising the nucleic acid molecule according to claim 14 and/or a vector comprising the nucleic acid molecule, or transformed or transfected with the nucleic acid molecule and/or the vector.

17. A method for detecting a disease associated with expression of ST2 or dysregulation of IL-33/ST2 pathway, including contacting the antibody or fragment thereof according to claim 1, a conjugate or fusion protein comprising the antibody or fragment thereof, and/or a composition comprising the antibody or fragment thereof or the conjugate or fusion protein with a sample from a subject.

18. The method according to claim 17, wherein the disease is an inflammatory disease or an autoimmune disease.

19. The method according to claim 17, wherein the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea.

20. A method for reducing the likelihood of, treating or ameliorating a disease associated with expression of ST2 or dysregulation of IL-33/ST2 pathway, including administering to a subject in need thereof the antibody or fragment thereof according to claim 1, a conjugate or fusion protein comprising the antibody or fragment thereof, and/or a composition comprising the antibody or fragment thereof or the conjugate or fusion protein, and optionally an additional drug.

21. The method according to claim 20, wherein the disease is an inflammatory disease or an autoimmune disease.

22. The method according to claim 20, wherein the disease is heart failure, allergic rhinitis, nasal polyps, atopic dermatitis, chronic obstructive pulmonary disease, asthma, pulmonary fibrosis, sepsis, inflammatory bowel disease, systemic lupus erythematosus, rheumatoid arthritis, systemic sclerosis, wegener's granulomatosis, or chemotherapy-associated diarrhea.

* * * * *

SEQUENCE LISTING

<160> NUMBER OF SEQ ID NOS: 105

<210> SEQ ID NO 1
<211> LENGTH: 117
<212> TYPE: PRT
<213> ORGANISM: Artificial Sequence
<220> FEATURE:
<223> OTHER INFORMATION: 5886-156H-VH

<400> SEQUENCE: 1

Asp Val Gln Leu Gln Gln Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asp Tyr Ser Gly Ser Thr Thr Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Thr Val Ile Asp Ser Met Asp Tyr Trp Gly Gln Gly Thr Ser
            100                 105                 110

Val Thr Val Ser Ser
            115

<210> SEQ ID NO 2
<211> LENGTH: 117
<212> TYPE: PRT
<213> ORGANISM: Artificial Sequence
<220> FEATURE:
<223> OTHER INFORMATION: 5886-156H-VH-HZ0

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

-continued

```
Ile Gly Tyr Ile Asp Tyr Ser Gly Ser Thr Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Thr Val Ile Asp Ser Met Asp Tyr Trp Gly Gln Gly Thr Leu
                100                 105                 110

Val Thr Val Ser Ser
                115
```

<210> SEQ ID NO 3
<211> LENGTH: 117
<212> TYPE: PRT
<213> ORGANISM: Artificial Sequence
<220> FEATURE:
<223> OTHER INFORMATION: 5886-156H-VH-HZ1

<400> SEQUENCE: 3

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
                20                  25                  30

Tyr Ala Trp Asn Trp Ile Arg Gln Pro Pro Gly Lys Gly Leu Glu Trp
            35                  40                  45

Ile Gly Tyr Ile Asp Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Thr Val Ile Asp Ser Met Asp Tyr Trp Gly Gln Gly Thr Leu
                100                 105                 110

Val Thr Val Ser Ser
                115
```

<210> SEQ ID NO 4
<211> LENGTH: 117
<212> TYPE: PRT
<213> ORGANISM: Artificial Sequence
<220> FEATURE:
<223> OTHER INFORMATION: 5887-41H-VH

<400> SEQUENCE: 4

```
Asp Val Gln Leu Gln Gln Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asp Trp Ile Arg Gln Phe Pro Gly Asn Lys Leu Glu Trp
            35                  40                  45

Met Gly Tyr Ile Arg Tyr Ser Gly Asp Thr Tyr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Thr Thr Met Met Asp Thr Met Asp Tyr Trp Gly Gln Gly Thr Ser
```

```
                100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: 5887-41H-VH-HZ0

<400> SEQUENCE: 5

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asp Trp Ile Arg Gln Pro Pro Gly Lys Gly Leu Glu Trp
        35                  40                  45

Ile Gly Tyr Ile Arg Tyr Ser Gly Asp Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Thr Met Met Asp Thr Met Asp Tyr Trp Gly Gln Gly Thr Leu
            100                 105                 110

Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: 5887-41H-VH-HZ1

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asp Trp Ile Arg Gln Pro Pro Gly Lys Gly Leu Glu Trp
        35                  40                  45

Ile Gly Tyr Ile Arg Tyr Ser Gly Asp Thr Tyr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Thr Thr Met Met Asp Thr Met Asp Tyr Trp Gly Gln Gly Thr Leu
            100                 105                 110

Val Thr Val Ser Ser
        115

<210> SEQ ID NO 7
<211> LENGTH: 120
<212> TYPE: PRT
<213> ORGANISM: Artificial Sequence
<220> FEATURE:
```

<223> OTHER INFORMATION: 5887-537H3-VH

<400> SEQUENCE: 7

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Gln Tyr Asn Pro Ala
    50                  55                  60

Leu Lys Ser Arg Leu Thr Ile Ser Lys Asp Thr Ser Ser Ser Gln Val
65                  70                  75                  80

Phe Leu Lys Ser Ala Ser Val Asp Thr Ala Asp Thr Ala Thr Tyr Tyr
                85                  90                  95

Cys Ala Arg Ile Gly Gly Asp Tyr Asp Tyr Phe Asp Phe Trp Gly Gln
            100                 105                 110

Gly Thr Thr Leu Thr Val Ser Ser
        115                 120
```

<210> SEQ ID NO 8
<211> LENGTH: 120
<212> TYPE: PRT
<213> ORGANISM: Artificial Sequence
<220> FEATURE:
<223> OTHER INFORMATION: 5887-537H3-VH-HZ0

<400> SEQUENCE: 8

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Gln Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ile Gly Gly Asp Tyr Asp Tyr Phe Asp Phe Trp Gly Gln
            100                 105                 110

Gly Thr Thr Val Thr Val Ser Ser
        115                 120
```

<210> SEQ ID NO 9
<211> LENGTH: 120
<212> TYPE: PRT
<213> ORGANISM: Artificial Sequence
<220> FEATURE:
<223> OTHER INFORMATION: 5887-537H3-VH-HZ1

<400> SEQUENCE: 9

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
```

-continued

```
                35                  40                  45

Trp Leu Ala His Ile Trp Trp Asp Asp Val Lys Gln Tyr Asn Pro Ala
    50                  55                  60

Leu Lys Ser Arg Leu Thr Ile Thr Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Gly Gly Asp Tyr Asp Tyr Phe Asp Phe Trp Gly Gln
                100                 105                 110

Gly Thr Thr Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: 5888-116H1-VH

<400> SEQUENCE: 10

Gln Val Gln Leu Gln Gln Ser Gly Ala Glu Leu Val Arg Pro Gly Ala
1                   5                   10                  15

Ser Val Thr Leu Ser Cys Lys Ala Ser Gly Tyr Thr Phe Thr Asp Ser
                20                  25                  30

Glu Met Tyr Trp Val Arg Leu Thr Pro Val His Gly Leu Glu Trp Ile
            35                  40                  45

Gly Ala Ile Asp Pro Glu Thr Gly Asp Thr Ala Phe Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Val Val Tyr Tyr Cys
                85                  90                  95

Thr Arg Ala Phe Asp Asn Asp Asn Asp Asp Gly Phe Ala Tyr Trp Gly
            100                 105                 110

Gln Gly Thr Leu Val Thr Val Ser Ala
            115                 120

<210> SEQ ID NO 11
<211> LENGTH: 121
<212> TYPE: PRT
<213> ORGANISM: Artificial Sequence
<220> FEATURE:
<223> OTHER INFORMATION: 5888-116H1-VH-HZ0

<400> SEQUENCE: 11

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asp Ser
                20                  25                  30

Glu Met Tyr Trp Val Arg Gln Ala Pro Gly Gln Gly Leu Glu Trp Met
            35                  40                  45

Gly Ala Ile Asp Pro Glu Thr Gly Asp Thr Ala Phe Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Ala Phe Asp Asn Asp Asn Asp Asp Gly Phe Ala Tyr Trp Gly
            100                 105                 110

Gln Gly Thr Met Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: 5888-116H1-VH-HZ1

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met Tyr Trp Val Arg Gln Ala Pro Gly Gln Gly Leu Glu Trp Met
        35                  40                  45

Gly Ala Ile Asp Pro Glu Thr Gly Asp Thr Ala Phe Asn Gln Lys Phe
    50                  55                  60

Lys Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Phe Asp Asn Asp Asn Asp Asp Gly Phe Ala Tyr Trp Gly
            100                 105                 110

Gln Gly Thr Met Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: 5888-116H1-VH-HZ2

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met Tyr Trp Val Arg Gln Ala Pro Gly Gln Gly Leu Glu Trp Met
        35                  40                  45

Gly Ala Ile Asp Pro Glu Thr Gly Asp Thr Ala Phe Asn Gln Lys Phe
    50                  55                  60

Lys Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Phe Asp Asn Asp Asn Asp Glu Gly Phe Ala Tyr Trp Gly
            100                 105                 110

Gln Gly Thr Met Val Thr Val Ser Ser
        115                 120

<210> SEQ ID NO 14
<211> LENGTH: 121
<212> TYPE: PRT
<213> ORGANISM: Artificial Sequence
```

```
<220> FEATURE:
<223> OTHER INFORMATION: 5888-116H1-VH-HZ3

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met Tyr Trp Val Arg Gln Ala Pro Gly Gln Gly Leu Glu Trp Met
        35                  40                  45

Gly Ala Ile Asp Pro Glu Thr Gly Asp Thr Ala Phe Asn Gln Lys Phe
    50                  55                  60

Lys Gly Arg Val Thr Met Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Thr Arg Ala Phe Asp Asn Asp Asn Asp Asp Ala Phe Ala Tyr Trp Gly
            100                 105                 110

Gln Gly Thr Met Val Thr Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: 5888-153H1-VH

<400> SEQUENCE: 15

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Leu His Trp Val Lys Gln Thr Pro Val His Gly Leu Glu Trp Ile
        35                  40                  45

Gly Thr Ile Asp Pro Glu Thr Gly Asp Thr Val Tyr Asn Gln Lys Phe
    50                  55                  60

Lys Ala Lys Ala Ile Leu Thr Ala Asp Lys Ser Ser Ser Thr Ala Tyr
65              70                  75                  80

Met Glu Phe Arg Ser Leu Thr Ser Glu Asp Ser Ala Val Cys Tyr Cys
                85                  90                  95

Thr Arg Ala Phe Tyr Asn Asp Tyr Asp Asp Gly Phe Ala Tyr Trp Gly
            100                 105                 110

Gln Gly Thr Leu Val Thr Val Ser Ala
        115                 120

<210> SEQ ID NO 16
<211> LENGTH: 121
<212> TYPE: PRT
<213> ORGANISM: Artificial Sequence
<220> FEATURE:
<223> OTHER INFORMATION: 5888-153H1-VH-HZ0

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Glu Leu His Trp Val Arg Gln Ala Pro Gly Gln Gly Leu Glu Trp Met
        35                  40                  45

Gly Thr Ile Asp Pro Glu Thr Gly Asp Thr Val Tyr Asn Gln Lys Phe
        50                  55                  60

Lys Ala Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Phe Tyr Asn Asp Tyr Asp Asp Gly Phe Ala Tyr Trp Gly
            100                 105                 110

Gln Gly Thr Leu Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: 5888-153H1-VH-HZ1

<400> SEQUENCE: 17

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asp Tyr
                20                  25                  30

Glu Leu His Trp Val Arg Gln Ala Pro Gly Gln Gly Leu Glu Trp Met
        35                  40                  45

Gly Thr Ile Asp Pro Glu Thr Gly Asp Thr Val Tyr Asn Gln Lys Phe
        50                  55                  60

Lys Ala Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Phe Tyr Asn Asp Tyr Asp Asp Gly Phe Ala Tyr Trp Gly
            100                 105                 110

Gln Gly Thr Leu Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: 5888-153H1-VH-HZ2

<400> SEQUENCE: 18

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asp Tyr
                20                  25                  30

Glu Leu His Trp Val Arg Gln Ala Pro Gly Gln Gly Leu Glu Trp Met
        35                  40                  45

Gly Thr Ile Asp Pro Glu Thr Gly Asp Thr Val Tyr Asn Gln Lys Phe
        50                  55                  60

Lys Ala Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Ala Phe Tyr Asn Asp Tyr Asp Glu Gly Phe Ala Tyr Trp Gly
        100                 105                 110

Gln Gly Thr Leu Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: 5888-153H1-VH-HZ3

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Leu His Trp Val Arg Gln Ala Pro Gly Gln Gly Leu Glu Trp Met
        35                  40                  45

Gly Thr Ile Asp Pro Glu Thr Gly Asp Thr Val Tyr Asn Gln Lys Phe
    50                  55                  60

Lys Ala Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Phe Tyr Asn Asp Tyr Asp Asp Ala Phe Ala Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: 5888-357H-VH

<400> SEQUENCE: 20

Gln Val Gln Leu Gln Gln Ser Val Thr Glu Leu Val Arg Pro Gly Ala
1               5                   10                  15

Ser Val Thr Leu Ser Cys Lys Ala Ser Gly Tyr Arg Phe Thr Asp Ser
            20                  25                  30

Glu Met His Trp Val Lys Gln Thr Pro Val His Gly Leu Glu Trp Ile
        35                  40                  45

Gly Thr Ile Asp Pro Glu Thr Gly Gly Thr Val Tyr Asn Gln Lys Phe
    50                  55                  60

Lys Gly Lys Ala Lys Leu Thr Ala Asp Arg Ser Ser Ser Thr Val Ser
65                  70                  75                  80

Met Glu Leu Arg Ser Leu Thr Ser Glu Asp Ser Ala Val Tyr Tyr Cys
                85                  90                  95

Thr Arg Ala Phe Tyr Asn Asp Phe Asp Asp Gly Phe Ala Tyr Trp Gly
            100                 105                 110

Gln Gly Thr Leu Val Thr Val Ser Ala
        115                 120

<210> SEQ ID NO 21
<211> LENGTH: 121
<212> TYPE: PRT
```

<213> ORGANISM: Artificial Sequence
<220> FEATURE:
<223> OTHER INFORMATION: 5888-357H-VH-HZ0

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Ser
            20                  25                  30

Glu Met His Trp Val Arg Gln Ala Pro Gly Gln Gly Leu Glu Trp Met
        35                  40                  45

Gly Thr Ile Asp Pro Glu Thr Gly Gly Thr Val Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Phe Tyr Asn Asp Phe Asp Asp Gly Phe Ala Tyr Trp Gly
            100                 105                 110

Gln Gly Thr Met Val Thr Val Ser Ser
        115                 120
```

<210> SEQ ID NO 22
<211> LENGTH: 121
<212> TYPE: PRT
<213> ORGANISM: Artificial Sequence
<220> FEATURE:
<223> OTHER INFORMATION: 5888-357H-VH-HZ1

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Ser
            20                  25                  30

Glu Met His Trp Val Arg Gln Ala Pro Gly Gln Gly Leu Glu Trp Met
        35                  40                  45

Gly Thr Ile Asp Pro Glu Thr Gly Gly Thr Val Tyr Asn Gln Lys Phe
    50                  55                  60

Lys Gly Arg Val Thr Met Thr Ala Asp Arg Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ala Phe Tyr Asn Asp Phe Asp Asp Gly Phe Ala Tyr Trp Gly
            100                 105                 110

Gln Gly Thr Met Val Thr Val Ser Ser
        115                 120
```

<210> SEQ ID NO 23
<211> LENGTH: 121
<212> TYPE: PRT
<213> ORGANISM: Artificial Sequence
<220> FEATURE:
<223> OTHER INFORMATION: 5888-357H-VH-HZ2

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Ser
            20                  25                  30
```

-continued

```
Glu Met His Trp Val Arg Gln Ala Pro Gly Gln Gly Leu Glu Trp Met
        35                  40                  45

Gly Thr Ile Asp Pro Glu Thr Gly Gly Thr Val Tyr Asn Gln Lys Phe
    50                  55                  60

Lys Gly Arg Val Thr Met Thr Ala Asp Arg Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ala Phe Tyr Asn Asp Phe Asp Glu Gly Phe Ala Tyr Trp Gly
            100                 105                 110

Gln Gly Thr Met Val Thr Val Ser Ser
        115                 120
```

```
<210> SEQ ID NO 24
<211> LENGTH: 121
<212> TYPE: PRT
<213> ORGANISM: Artificial Sequence
<220> FEATURE:
<223> OTHER INFORMATION: 5888-357H-VH-HZ3

<400> SEQUENCE: 24
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Ser
            20                  25                  30

Glu Met His Trp Val Arg Gln Ala Pro Gly Gln Gly Leu Glu Trp Met
        35                  40                  45

Gly Thr Ile Asp Pro Glu Thr Gly Gly Thr Val Tyr Asn Gln Lys Phe
    50                  55                  60

Lys Gly Arg Val Thr Met Thr Ala Asp Arg Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ala Phe Tyr Asn Asp Phe Asp Asp Ala Phe Ala Tyr Trp Gly
            100                 105                 110

Gln Gly Thr Met Val Thr Val Ser Ser
        115                 120
```

```
<210> SEQ ID NO 25
<211> LENGTH: 116
<212> TYPE: PRT
<213> ORGANISM: Artificial Sequence
<220> FEATURE:
<223> OTHER INFORMATION: 5888-379H1-VH

<400> SEQUENCE: 25
```

```
Gln Ile Gln Leu Ala Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Asp Leu Lys Trp Met
        35                  40                  45

Gly Trp Ile Asn Thr Tyr Ile Gly Glu Pro Thr Tyr Gly Asp Asn Phe
    50                  55                  60

Lys Gly Arg Phe Ala Phe Ser Leu Glu Thr Ser Ala Ser Thr Val Tyr
65                  70                  75                  80

Leu Gln Ile Asn Asn Leu Lys Asn Glu Asp Thr Ala Thr Tyr Phe Cys
```

```
                    85                  90                  95

Ala Arg Glu Gly Asp Gly Phe Ala Tyr Trp Gly Gln Gly Thr Leu Val
            100                 105                 110

Thr Val Ser Ala
        115

<210> SEQ ID NO 26
<211> LENGTH: 116
<212> TYPE: PRT
<213> ORGANISM: Artificial Sequence
<220> FEATURE:
<223> OTHER INFORMATION: 5888-379H1-HZ0

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Ile Gly Glu Pro Thr Tyr Gly Asp Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Gly Phe Ala Tyr Trp Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: 5888-379H1-VH-HZ1

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Ile Gly Glu Pro Thr Tyr Gly Asp Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Gly Phe Ala Tyr Trp Gly Gln Gly Thr Leu Val
            100                 105                 110

Thr Val Ser Ser
        115

<210> SEQ ID NO 28
<211> LENGTH: 116
```

```
<212> TYPE: PRT
<213> ORGANISM: Artificial Sequence
<220> FEATURE:
<223> OTHER INFORMATION: 5888-379H1-VH-HZ2

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Ile Gly Glu Pro Thr Tyr Gly Asp Asn Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Ala Phe Ala Tyr Trp Gly Gln Gly Thr Leu Val
                100                 105                 110

Thr Val Ser Ser
        115

<210> SEQ ID NO 29
<211> LENGTH: 111
<212> TYPE: PRT
<213> ORGANISM: Artificial Sequence
<220> FEATURE:
<223> OTHER INFORMATION: 5886-156L-VL

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly His Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Glu Asp Ala Ala Thr Tyr Tyr Cys Gln His Ser Arg
                85                  90                  95

Glu Phe Pro Phe Thr Phe Gly Ser Gly Thr Lys Leu Glu Ile Lys
                100                 105                 110

<210> SEQ ID NO 30
<211> LENGTH: 111
<212> TYPE: PRT
<213> ORGANISM: Artificial Sequence
<220> FEATURE:
<223> OTHER INFORMATION: 5886-156L-VL-HZ0

<400> SEQUENCE: 30

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly His Ser Tyr Met His Trp Tyr Gln Gln Lys Pro Gly Gln Pro Pro
```

```
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Phe Thr Phe Gly Gln Gly Thr Lys Val Glu Ile Lys
                100                 105                 110

<210> SEQ ID NO 31
<211> LENGTH: 111
<212> TYPE: PRT
<213> ORGANISM: Artificial Sequence
<220> FEATURE:
<223> OTHER INFORMATION: 5886-156L-VL-HZ1

<400> SEQUENCE: 31

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
                20                  25                  30

Gly His Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Arg
                85                  90                  95

Glu Phe Pro Phe Thr Phe Gly Gln Gly Thr Lys Val Glu Ile Lys
                100                 105                 110

<210> SEQ ID NO 32
<211> LENGTH: 111
<212> TYPE: PRT
<213> ORGANISM: Artificial Sequence
<220> FEATURE:
<223> OTHER INFORMATION: 5887-41L-VL

<400> SEQUENCE: 32

Asp Ile Val Leu Thr Gln Ser Pro Ala Ser Leu Thr Val Ser Leu Gly
1               5                   10                  15

Gln Arg Ala Thr Ile Ser Cys Arg Ala Ser Lys Ser Val Ser Thr Ser
                20                  25                  30

Gly Asn Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Leu Thr Phe Gly Ala Gly Thr Lys Leu Glu Leu Lys
                100                 105                 110

<210> SEQ ID NO 33
<211> LENGTH: 111
```

```
<212> TYPE: PRT
<213> ORGANISM: Artificial Sequence
<220> FEATURE:
<223> OTHER INFORMATION: 5887-41L-VL-HZ0

<400> SEQUENCE: 33

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Leu Thr Phe Gly Gln Gly Thr Lys Leu Glu Ile Lys
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: 5887-41L-VL-HZ1

<400> SEQUENCE: 34

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Arg
                85                  90                  95

Glu Phe Pro Leu Thr Phe Gly Gln Gly Thr Lys Leu Glu Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: 5887-41L-VL-HZ2

<400> SEQUENCE: 35

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Asn Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
```

```
                50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Arg
                85                  90                  95

Glu Phe Pro Leu Thr Phe Gly Gln Gly Thr Lys Leu Glu Ile Lys
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: 5887-537L1-VL

<400> SEQUENCE: 36

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Ser
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Ala
        50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: 5887-537L1-VL-HZ0

<400> SEQUENCE: 37

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Tyr Ser
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 38
<211> LENGTH: 111
<212> TYPE: PRT
<213> ORGANISM: Artificial Sequence
<220> FEATURE:
```

<223> OTHER INFORMATION: 5887-537L1-VL-HZ1

<400> SEQUENCE: 38

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Tyr Ser
            20                  25                  30

Gly Thr Ser Leu Met Gln Trp Tyr Gln Gln Lys Pro Gly Gln Pro Pro
        35                  40                  45

Lys Leu Leu Ile Tyr Val Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Ile Ala Asn Tyr Phe Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 39
<211> LENGTH: 106
<212> TYPE: PRT
<213> ORGANISM: Artificial Sequence
<220> FEATURE:
<223> OTHER INFORMATION: 5888-116L1-VL

<400> SEQUENCE: 39

Gln Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: 5888-116L1-VL-HZ0

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu

```
65                   70                   75                   80

Asp Ile Ala Thr Tyr Tyr Cys Gln Gln Trp Ser Ser Asn Pro Leu Thr
                85                   90                   95

Phe Gly Gln Gly Thr Lys Leu Glu Ile Lys
            100                   105

<210> SEQ ID NO 41
<211> LENGTH: 106
<212> TYPE: PRT
<213> ORGANISM: Artificial Sequence
<220> FEATURE:
<223> OTHER INFORMATION: 5888-116L1-VL-HZ1

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Met
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: 5888-153L2-VL

<400> SEQUENCE: 42

Gln Ile Val Met Thr Gln Thr Pro Ala Ile Met Ser Ala Ser Pro Gly
1               5                   10                  15

Glu Lys Val Thr Met Thr Cys Ser Val Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Asn Asn Met Glu Ala Glu
65                  70                  75                  80

Asp Ala Ala Thr Tyr Tyr Cys Gln Gln Trp Asn Ser Ser Pro Leu Thr
                85                  90                  95

Phe Gly Ala Gly Thr Lys Leu Glu Leu Lys
            100                 105

<210> SEQ ID NO 43
<211> LENGTH: 106
<212> TYPE: PRT
<213> ORGANISM: Artificial Sequence
<220> FEATURE:
<223> OTHER INFORMATION: 5888-153L2-VL-HZ0

<400> SEQUENCE: 43
```

-continued

```
Glu Ile Val Leu Thr Gln Ser Pro Ala Thr Leu Ser Leu Ser Pro Gly
1               5                   10                  15

Glu Arg Ala Thr Leu Ser Cys Ser Val Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Asn Ser Ser Pro Leu Thr
                85                  90                  95

Phe Gly Gly Gly Thr Lys Val Glu Ile Lys
            100                 105
```

```
<210> SEQ ID NO 44
<211> LENGTH: 106
<212> TYPE: PRT
<213> ORGANISM: Artificial Sequence
<220> FEATURE:
<223> OTHER INFORMATION: 5888-153L2-VL-HZ1

<400> SEQUENCE: 44
```

```
Glu Ile Val Met Thr Gln Ser Pro Ala Thr Leu Ser Leu Ser Pro Gly
1               5                   10                  15

Glu Arg Ala Thr Leu Ser Cys Ser Val Ser Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Ala Ala Val Tyr Tyr Cys Gln Gln Trp Asn Ser Ser Pro Leu Thr
                85                  90                  95

Phe Gly Gly Gly Thr Lys Val Glu Ile Lys
            100                 105
```

```
<210> SEQ ID NO 45
<211> LENGTH: 106
<212> TYPE: PRT
<213> ORGANISM: Artificial Sequence
<220> FEATURE:
<223> OTHER INFORMATION: 5888-153L2-VL-HZ2

<400> SEQUENCE: 45
```

```
Glu Ile Val Met Thr Gln Ser Pro Ala Thr Leu Ser Leu Ser Pro Gly
1               5                   10                  15

Glu Arg Ala Thr Leu Ser Cys Ser Val Ser Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Ala Ala Val Tyr Tyr Cys Gln Gln Trp Asn Thr Ser Pro Leu Thr
```

-continued

```
                         85                   90                   95

Phe Gly Gly Gly Thr Lys Val Glu Ile Lys
            100               105

<210> SEQ ID NO 46
<211> LENGTH: 106
<212> TYPE: PRT
<213> ORGANISM: Artificial Sequence
<220> FEATURE:
<223> OTHER INFORMATION: 5888-357L-VL

<400> SEQUENCE: 46

Gln Ile Val Met Thr Gln Ser Pro Ala Ile Met Ser Ala Ser Pro Gly
1               5                   10                  15

Glu Lys Val Thr Leu Thr Cys Ser Ala Ser Thr Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys
            100               105

<210> SEQ ID NO 47
<211> LENGTH: 106
<212> TYPE: PRT
<213> ORGANISM: Artificial Sequence
<220> FEATURE:
<223> OTHER INFORMATION: 5888-357L-VL-HZ0

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Thr Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
            85                  90                  95

Phe Gly Gly Gly Thr Lys Val Glu Ile Lys
            100               105

<210> SEQ ID NO 48
<211> LENGTH: 106
<212> TYPE: PRT
<213> ORGANISM: Artificial Sequence
<220> FEATURE:
<223> OTHER INFORMATION: 5888-357L-VL-HZ1

<400> SEQUENCE: 48

Glu Ile Val Met Thr Gln Ser Pro Ala Thr Leu Ser Leu Ser Pro Gly
1               5                   10                  15
```

-continued

Glu Arg Ala Thr Leu Ser Cys Ser Ala Ser Thr Ser Val Ser Tyr Met
            20                  25                  30

His Trp Tyr Gln Gln Lys Pro Gly Gln Ala Pro Arg Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Ala Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 49
<211> LENGTH: 113
<212> TYPE: PRT
<213> ORGANISM: Artificial Sequence
<220> FEATURE:
<223> OTHER INFORMATION: 5888-379L2-VL

<400> SEQUENCE: 49

Asp Ile Val Met Thr Gln Ser Pro Pro Ser Leu Ser Val Ser Val Gly
1               5                   10                  15

Glu Lys Val Thr Met Ser Cys Lys Ser Ser Gln Ser Leu Leu Tyr Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys

<210> SEQ ID NO 50
<211> LENGTH: 113
<212> TYPE: PRT
<213> ORGANISM: Artificial Sequence
<220> FEATURE:
<223> OTHER INFORMATION: 5888-379L2-VK4-HZ0

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

```
Asp His Ser Tyr Pro Tyr Thr Phe Gly Gly Gly Thr Lys Val Glu Ile
            100             105             110

Lys

<210> SEQ ID NO 51
<211> LENGTH: 113
<212> TYPE: PRT
<213> ORGANISM: Artificial Sequence
<220> FEATURE:
<223> OTHER INFORMATION: 5888-379L2-VK4-HZ1

<400> SEQUENCE: 51

Asp Ile Val Met Thr Gln Ser Pro Asp Ser Leu Ala Val Ser Leu Gly
1               5               10              15

Glu Arg Ala Thr Ile Asn Cys Lys Ser Ser Gln Ser Leu Leu Tyr Ser
            20              25              30

Gly Asn Gln Asn Asn Tyr Leu Ala Trp Tyr Gln Gln Lys Pro Gly Gln
        35              40              45

Pro Pro Lys Leu Leu Ile Tyr Gly Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Leu Ala Val Tyr Tyr Cys Gln Asn
            85              90              95

Asp His Ser Tyr Pro Tyr Thr Phe Gly Gly Gly Thr Lys Val Glu Ile
            100             105             110

Lys

<210> SEQ ID NO 52
<211> LENGTH: 113
<212> TYPE: PRT
<213> ORGANISM: Artificial Sequence
<220> FEATURE:
<223> OTHER INFORMATION: 5888-379L2-VK1-HZ0

<400> SEQUENCE: 52

Asp Ile Gln Met Thr Gln Ser Pro Ser Ser Leu Ser Ala Ser Val Gly
1               5               10              15

Asp Arg Val Thr Ile Thr Cys Lys Ser Ser Gln Ser Leu Leu Tyr Ser
            20              25              30

Gly Asn Gln Asn Asn Tyr Leu Ala Trp Tyr Gln Gln Lys Pro Gly Lys
        35              40              45

Val Pro Lys Leu Leu Ile Tyr Gly Ala Ser Thr Arg Glu Ser Gly Val
    50              55              60

Pro Ser Arg Phe Ser Gly Ser Gly Ser Gly Thr Asp Phe Thr Leu Thr
65              70              75              80

Ile Ser Ser Leu Gln Pro Glu Asp Val Ala Thr Tyr Tyr Cys Gln Asn
            85              90              95

Asp His Ser Tyr Pro Tyr Thr Phe Gly Gly Gly Thr Lys Val Glu Ile
            100             105             110

Lys

<210> SEQ ID NO 53
<211> LENGTH: 113
<212> TYPE: PRT
<213> ORGANISM: Artificial Sequence
<220> FEATURE:
<223> OTHER INFORMATION: 5888-379L2-VK1-HZ1
```

-continued

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Gly Asn Gln Asn Asn Tyr Leu Ala Trp Tyr Gln Gln Lys Pro Gly Lys
        35                  40                  45

Val Pro Lys Leu Leu Ile Tyr Gly Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Asn
                85                  90                  95

Asp His Ser Tyr Pro Tyr Thr Phe Gly Gly Gly Thr Lys Val Glu Ile
            100                 105                 110

Lys
```

<210> SEQ ID NO 54
<211> LENGTH: 327
<212> TYPE: PRT
<213> ORGANISM: Artificial Sequence
<220> FEATURE:
<223> OTHER INFORMATION: Human IgG4

<400> SEQUENCE: 54

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
```

```
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 55
<211> LENGTH: 107
<212> TYPE: PRT
<213> ORGANISM: Artificial Sequence
<220> FEATURE:
<223> OTHER INFORMATION: Human kappa

<400> SEQUENCE: 55

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

```
<210> SEQ ID NO 56
<211> LENGTH: 11
<212> TYPE: PRT
<213> ORGANISM: Artificial Sequence
<220> FEATURE:
<223> OTHER INFORMATION: H-CDR1

<400> SEQUENCE: 56

Gly Tyr Ser Ile Thr Ser Asp Tyr Ala Trp Asn
1                   5                   10
```

```
<210> SEQ ID NO 57
<211> LENGTH: 11
<212> TYPE: PRT
<213> ORGANISM: Artificial Sequence
<220> FEATURE:
<223> OTHER INFORMATION: H-CDR1

<400> SEQUENCE: 57

Gly Tyr Ser Ile Thr Ser Asp Tyr Ala Trp Asp
1                   5                   10
```

```
<210> SEQ ID NO 58
```

-continued

```
<211> LENGTH: 12
<212> TYPE: PRT
<213> ORGANISM: Artificial Sequence
<220> FEATURE:
<223> OTHER INFORMATION: H-CDR1

<400> SEQUENCE: 58

Gly Phe Ser Leu Ser Thr Ser Gly Met Gly Val Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: H-CDR1

<400> SEQUENCE: 59

Gly Tyr Thr Phe Thr Asp Ser Glu Met Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: H-CDR1

<400> SEQUENCE: 60

Gly Tyr Thr Phe Thr Asp Tyr Glu Leu His
1               5                   10

<210> SEQ ID NO 61
<211> LENGTH: 10
<212> TYPE: PRT
<213> ORGANISM: Artificial Sequence
<220> FEATURE:
<223> OTHER INFORMATION: H-CDR1

<400> SEQUENCE: 61

Gly Tyr Arg Phe Thr Asp Ser Glu Met His
1               5                   10

<210> SEQ ID NO 62
<211> LENGTH: 10
<212> TYPE: PRT
<213> ORGANISM: Artificial Sequence
<220> FEATURE:
<223> OTHER INFORMATION: H-CDR1

<400> SEQUENCE: 62

Gly Tyr Thr Phe Ile Asn Tyr Gly Met Asn
1               5                   10

<210> SEQ ID NO 63
<211> LENGTH: 16
<212> TYPE: PRT
<213> ORGANISM: Artificial Sequence
<220> FEATURE:
<223> OTHER INFORMATION: H-CDR2

<400> SEQUENCE: 63

Tyr Ile Asp Tyr Ser Gly Ser Thr Thr Tyr Asn Pro Ser Leu Lys Ser
1               5                   10                  15

<210> SEQ ID NO 64
<211> LENGTH: 16
```

-continued

```
<212> TYPE: PRT
<213> ORGANISM: Artificial Sequence
<220> FEATURE:
<223> OTHER INFORMATION: H-CDR2

<400> SEQUENCE: 64

Tyr Ile Arg Tyr Ser Gly Asp Thr Tyr Tyr Asn Pro Ser Leu Lys Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: H-CDR2

<400> SEQUENCE: 65

His Ile Trp Trp Asp Asp Val Lys Gln Tyr Asn Pro Ala Leu Lys Ser
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: H-CDR2

<400> SEQUENCE: 66

Ala Ile Asp Pro Glu Thr Gly Asp Thr Ala Phe Asn Gln Lys Phe Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: H-CDR2

<400> SEQUENCE: 67

Thr Ile Asp Pro Glu Thr Gly Asp Thr Val Tyr Asn Gln Lys Phe Lys
1               5                   10                  15

Ala

<210> SEQ ID NO 68
<211> LENGTH: 17
<212> TYPE: PRT
<213> ORGANISM: Artificial Sequence
<220> FEATURE:
<223> OTHER INFORMATION: H-CDR2

<400> SEQUENCE: 68

Thr Ile Asp Pro Glu Thr Gly Gly Thr Val Tyr Asn Gln Lys Phe Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: H-CDR2

<400> SEQUENCE: 69

Trp Ile Asn Thr Tyr Ile Gly Glu Pro Thr Tyr Gly Asp Asn Phe Lys
```

-continued

```
1               5               10              15

Gly

<210> SEQ ID NO 70
<211> LENGTH: 8
<212> TYPE: PRT
<213> ORGANISM: Artificial Sequence
<220> FEATURE:
<223> OTHER INFORMATION: H-CDR3

<400> SEQUENCE: 70

Thr Val Ile Asp Ser Met Asp Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: H-CDR3

<400> SEQUENCE: 71

Thr Met Met Asp Thr Met Asp Tyr
1               5

<210> SEQ ID NO 72
<211> LENGTH: 10
<212> TYPE: PRT
<213> ORGANISM: Artificial Sequence
<220> FEATURE:
<223> OTHER INFORMATION: H-CDR3

<400> SEQUENCE: 72

Ile Gly Gly Asp Tyr Asp Tyr Phe Asp Phe
1               5               10

<210> SEQ ID NO 73
<211> LENGTH: 12
<212> TYPE: PRT
<213> ORGANISM: Artificial Sequence
<220> FEATURE:
<223> OTHER INFORMATION: H-CDR3

<400> SEQUENCE: 73

Ala Phe Asp Asn Asp Asn Asp Asp Gly Phe Ala Tyr
1               5               10

<210> SEQ ID NO 74
<211> LENGTH: 12
<212> TYPE: PRT
<213> ORGANISM: Artificial Sequence
<220> FEATURE:
<223> OTHER INFORMATION: H-CDR3

<400> SEQUENCE: 74

Ala Phe Asp Asn Asp Asn Asp Glu Gly Phe Ala Tyr
1               5               10

<210> SEQ ID NO 75
<211> LENGTH: 12
<212> TYPE: PRT
<213> ORGANISM: Artificial Sequence
<220> FEATURE:
<223> OTHER INFORMATION: H-CDR3

<400> SEQUENCE: 75
```

```
Ala Phe Asp Asn Asp Asn Asp Asp Ala Phe Ala Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: H-CDR3

<400> SEQUENCE: 76

Ala Phe Tyr Asn Asp Tyr Asp Asp Gly Phe Ala Tyr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: H-CDR3

<400> SEQUENCE: 77

Ala Phe Tyr Asn Asp Tyr Asp Glu Gly Phe Ala Tyr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: H-CDR3

<400> SEQUENCE: 78

Ala Phe Tyr Asn Asp Tyr Asp Asp Ala Phe Ala Tyr
1               5                   10

<210> SEQ ID NO 79
<211> LENGTH: 12
<212> TYPE: PRT
<213> ORGANISM: Artificial Sequence
<220> FEATURE:
<223> OTHER INFORMATION: H-CDR3

<400> SEQUENCE: 79

Ala Phe Tyr Asn Asp Phe Asp Asp Gly Phe Ala Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: H-CDR3

<400> SEQUENCE: 80

Ala Phe Tyr Asn Asp Phe Asp Glu Gly Phe Ala Tyr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: H-CDR3

<400> SEQUENCE: 81

Ala Phe Tyr Asn Asp Phe Asp Asp Ala Phe Ala Tyr
```

1                5                    10

```
<210> SEQ ID NO 82
<211> LENGTH: 7
<212> TYPE: PRT
<213> ORGANISM: Artificial Sequence
<220> FEATURE:
<223> OTHER INFORMATION: H-CDR3

<400> SEQUENCE: 82

Glu Gly Asp Gly Phe Ala Tyr
1                5

<210> SEQ ID NO 83
<211> LENGTH: 7
<212> TYPE: PRT
<213> ORGANISM: Artificial Sequence
<220> FEATURE:
<223> OTHER INFORMATION: H-CDR3

<400> SEQUENCE: 83

Glu Gly Glu Gly Phe Ala Tyr
1                5

<210> SEQ ID NO 84
<211> LENGTH: 7
<212> TYPE: PRT
<213> ORGANISM: Artificial Sequence
<220> FEATURE:
<223> OTHER INFORMATION: H-CDR3

<400> SEQUENCE: 84

Glu Gly Asp Ala Phe Ala Tyr
1                5

<210> SEQ ID NO 85
<211> LENGTH: 15
<212> TYPE: PRT
<213> ORGANISM: Artificial Sequence
<220> FEATURE:
<223> OTHER INFORMATION: L-CDR1

<400> SEQUENCE: 85

Arg Ala Ser Lys Ser Val Ser Thr Ser Gly His Ser Tyr Met His
1                5                    10                   15

<210> SEQ ID NO 86
<211> LENGTH: 15
<212> TYPE: PRT
<213> ORGANISM: Artificial Sequence
<220> FEATURE:
<223> OTHER INFORMATION: L-CDR1

<400> SEQUENCE: 86

Arg Ala Ser Lys Ser Val Ser Thr Ser Gly Asn Ser Tyr Met His
1                5                    10                   15

<210> SEQ ID NO 87
<211> LENGTH: 15
<212> TYPE: PRT
<213> ORGANISM: Artificial Sequence
<220> FEATURE:
<223> OTHER INFORMATION: L-CDR1

<400> SEQUENCE: 87

Arg Ala Ser Lys Ser Val Ser Thr Ser Gly Asn Thr Tyr Met His
1                5                    10                   15
```

-continued

```
<210> SEQ ID NO 88
<211> LENGTH: 15
<212> TYPE: PRT
<213> ORGANISM: Artificial Sequence
<220> FEATURE:
<223> OTHER INFORMATION: L-CDR1

<400> SEQUENCE: 88

Arg Ala Ser Glu Ser Val Glu Tyr Ser Gly Thr Ser Leu Met Gln
1               5                   10                  15

<210> SEQ ID NO 89
<211> LENGTH: 10
<212> TYPE: PRT
<213> ORGANISM: Artificial Sequence
<220> FEATURE:
<223> OTHER INFORMATION: L-CDR1

<400> SEQUENCE: 89

Ser Ala Ser Ser Ser Val Asn Tyr Met His
1               5                   10

<210> SEQ ID NO 90
<211> LENGTH: 10
<212> TYPE: PRT
<213> ORGANISM: Artificial Sequence
<220> FEATURE:
<223> OTHER INFORMATION: L-CDR1

<400> SEQUENCE: 90

Ser Val Ser Ser Ser Val Ser Tyr Met His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: L-CDR1

<400> SEQUENCE: 91

Ser Ala Ser Thr Ser Val Ser Tyr Met His
1               5                   10

<210> SEQ ID NO 92
<211> LENGTH: 17
<212> TYPE: PRT
<213> ORGANISM: Artificial Sequence
<220> FEATURE:
<223> OTHER INFORMATION: L-CDR1

<400> SEQUENCE: 92

Lys Ser Ser Gln Ser Leu Leu Tyr Ser Gly Asn Gln Asn Asn Tyr Leu
1               5                   10                  15

Ala

<210> SEQ ID NO 93
<211> LENGTH: 7
<212> TYPE: PRT
<213> ORGANISM: Artificial Sequence
<220> FEATURE:
<223> OTHER INFORMATION: L-CDR2

<400> SEQUENCE: 93

Leu Ala Ser Asn Leu Glu Ser
```

-continued

```
1               5

<210> SEQ ID NO 94
<211> LENGTH: 7
<212> TYPE: PRT
<213> ORGANISM: Artificial Sequence
<220> FEATURE:
<223> OTHER INFORMATION: L-CDR2

<400> SEQUENCE: 94

Val Ala Ser Asn Val Glu Ser
1               5

<210> SEQ ID NO 95
<211> LENGTH: 7
<212> TYPE: PRT
<213> ORGANISM: Artificial Sequence
<220> FEATURE:
<223> OTHER INFORMATION: L-CDR2

<400> SEQUENCE: 95

Asp Thr Ser Lys Leu Ala Ser
1               5

<210> SEQ ID NO 96
<211> LENGTH: 7
<212> TYPE: PRT
<213> ORGANISM: Artificial Sequence
<220> FEATURE:
<223> OTHER INFORMATION: L-CDR2

<400> SEQUENCE: 96

Gly Ala Ser Thr Arg Glu Ser
1               5

<210> SEQ ID NO 97
<211> LENGTH: 9
<212> TYPE: PRT
<213> ORGANISM: Artificial Sequence
<220> FEATURE:
<223> OTHER INFORMATION: L-CDR3

<400> SEQUENCE: 97

Gln His Ser Arg Glu Phe Pro Phe Thr
1               5

<210> SEQ ID NO 98
<211> LENGTH: 9
<212> TYPE: PRT
<213> ORGANISM: Artificial Sequence
<220> FEATURE:
<223> OTHER INFORMATION: L-CDR3

<400> SEQUENCE: 98

Gln His Ser Arg Glu Phe Pro Leu Thr
1               5

<210> SEQ ID NO 99
<211> LENGTH: 9
<212> TYPE: PRT
<213> ORGANISM: Artificial Sequence
<220> FEATURE:
<223> OTHER INFORMATION: L-CDR3

<400> SEQUENCE: 99

Gln Gln Ser Arg Lys Val Pro Trp Thr
1               5
```

-continued

```
<210> SEQ ID NO 100
<211> LENGTH: 9
<212> TYPE: PRT
<213> ORGANISM: Artificial Sequence
<220> FEATURE:
<223> OTHER INFORMATION: L-CDR3

<400> SEQUENCE: 100

Gln Gln Trp Ser Ser Asn Pro Leu Thr
1               5

<210> SEQ ID NO 101
<211> LENGTH: 9
<212> TYPE: PRT
<213> ORGANISM: Artificial Sequence
<220> FEATURE:
<223> OTHER INFORMATION: L-CDR3

<400> SEQUENCE: 101

Gln Gln Trp Asn Ser Ser Pro Leu Thr
1               5

<210> SEQ ID NO 102
<211> LENGTH: 9
<212> TYPE: PRT
<213> ORGANISM: Artificial Sequence
<220> FEATURE:
<223> OTHER INFORMATION: L-CDR3

<400> SEQUENCE: 102

Gln Gln Trp Asn Thr Ser Pro Leu Thr
1               5

<210> SEQ ID NO 103
<211> LENGTH: 9
<212> TYPE: PRT
<213> ORGANISM: Artificial Sequence
<220> FEATURE:
<223> OTHER INFORMATION: L-CDR3

<400> SEQUENCE: 103

Gln Asn Asp His Ser Tyr Pro Tyr Thr
1               5

<210> SEQ ID NO 104
<211> LENGTH: 450
<212> TYPE: PRT
<213> ORGANISM: Artificial Sequence
<220> FEATURE:
<223> OTHER INFORMATION: CNTO7160H

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ile Trp Val Arg Gln Ala Pro Gly Lys Gly Leu Glu Trp Val
        35                  40                  45

Ser Ser Ile Arg Gly Glu Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
              85                    90                    95

Ala Arg Asp Pro Trp Ser Thr Glu Gly Ser Phe Phe Val Leu Asp Tyr
            100                   105                   110

Trp Gly Gln Gly Thr Leu Val Thr Val Ser Ser Ala Ser Thr Lys Gly
            115                   120                   125

Pro Ser Val Phe Pro Leu Ala Pro Cys Ser Arg Ser Thr Ser Glu Ser
            130                   135                   140

Thr Ala Ala Leu Gly Cys Leu Val Lys Asp Tyr Phe Pro Glu Pro Val
145                   150                   155                   160

Thr Val Ser Trp Asn Ser Gly Ala Leu Thr Ser Gly Val His Thr Phe
                  165                   170                   175

Pro Ala Val Leu Gln Ser Ser Gly Leu Tyr Ser Leu Ser Ser Val Val
                  180                   185                   190

Thr Val Pro Ser Ser Ser Leu Gly Thr Lys Thr Tyr Thr Cys Asn Val
                  195                   200                   205

Asp His Lys Pro Ser Asn Thr Lys Val Asp Lys Arg Val Glu Ser Lys
            210                   215                   220

Tyr Gly Pro Pro Cys Pro Pro Cys Pro Ala Pro Glu Phe Leu Gly Gly
225                   230                   235                   240

Pro Ser Val Phe Leu Phe Pro Pro Lys Pro Lys Asp Thr Leu Met Ile
                  245                   250                   255

Ser Arg Thr Pro Glu Val Thr Cys Val Val Val Asp Val Ser Gln Glu
                  260                   265                   270

Asp Pro Glu Val Gln Phe Asn Trp Tyr Val Asp Gly Val Glu Val His
            275                   280                   285

Asn Ala Lys Thr Lys Pro Arg Glu Glu Gln Phe Asn Ser Thr Tyr Arg
            290                   295                   300

Val Val Ser Val Leu Thr Val Leu His Gln Asp Trp Leu Asn Gly Lys
305                   310                   315                   320

Glu Tyr Lys Cys Lys Val Ser Asn Lys Gly Leu Pro Ser Ser Ile Glu
                  325                   330                   335

Lys Thr Ile Ser Lys Ala Lys Gly Gln Pro Arg Glu Pro Gln Val Tyr
                  340                   345                   350

Thr Leu Pro Pro Ser Gln Glu Glu Met Thr Lys Asn Gln Val Ser Leu
            355                   360                   365

Thr Cys Leu Val Lys Gly Phe Tyr Pro Ser Asp Ile Ala Val Glu Trp
            370                   375                   380

Glu Ser Asn Gly Gln Pro Glu Asn Asn Tyr Lys Thr Thr Pro Pro Val
385                   390                   395                   400

Leu Asp Ser Asp Gly Ser Phe Phe Leu Tyr Ser Arg Leu Thr Val Asp
                  405                   410                   415

Lys Ser Arg Trp Gln Glu Gly Asn Val Phe Ser Cys Ser Val Met His
                  420                   425                   430

Glu Ala Leu His Asn His Tyr Thr Gln Lys Ser Leu Ser Leu Ser Leu
            435                   440                   445

Gly Lys
    450
```

<210> SEQ ID NO 105
<211> LENGTH: 214
<212> TYPE: PRT
<213> ORGANISM: Artificial Sequence
<220> FEATURE:
<223> OTHER INFORMATION: CNTO7160L -continued

```
<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Thr Ala Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```